US011434292B2

(12) United States Patent
Apgar et al.

(10) Patent No.: US 11,434,292 B2
(45) Date of Patent: *Sep. 6, 2022

(54) ANTIBODIES SPECIFIC FOR CD3 AND USES THEREOF

(71) Applicant: Pfizer Inc., New York, NY (US)

(72) Inventors: James Reasoner Apgar, Newton, MA (US); Fang Jin, Waban, MA (US); Madan Katragadda, Acton, MA (US); Divya Mathur, Scarsdale, NY (US); Lioudmila Gennadievna Tchistiakova, Stoneham, MA (US)

(73) Assignee: PFIZER INC., New York, NY (US)

( * ) Notice: Subject to any disclaimer, the term of this patent is extended or adjusted under 35 U.S.C. 154(b) by 380 days.

This patent is subject to a terminal disclaimer.

(21) Appl. No.: 16/417,859

(22) Filed: May 21, 2019

(65) Prior Publication Data

US 2019/0382486 A1 Dec. 19, 2019

Related U.S. Application Data

(60) Provisional application No. 62/847,460, filed on May 14, 2019, provisional application No. 62/675,562, filed on May 23, 2018.

(51) Int. Cl.
*C07K 16/28* (2006.01)
*A61P 35/00* (2006.01)
*C07K 16/30* (2006.01)
*C07K 16/40* (2006.01)
*C07K 16/46* (2006.01)
*A61K 39/00* (2006.01)

(52) U.S. Cl.
CPC .......... *C07K 16/2809* (2013.01); *A61P 35/00* (2018.01); *C07K 16/2863* (2013.01); *C07K 16/30* (2013.01); *C07K 16/40* (2013.01); *C07K 16/468* (2013.01); *A61K 2039/505* (2013.01); *C07K 2317/21* (2013.01); *C07K 2317/24* (2013.01); *C07K 2317/31* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Regen |
| 4,544,545 A | 10/1985 | Ryan et al. |
| 4,683,195 A | 7/1987 | Mullis et al. |
| 4,683,202 A | 7/1987 | Mullis et al. |
| 4,689,338 A | 8/1987 | Gerster |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 4,929,624 A | 5/1990 | Gerster et al. |
| 5,013,556 A | 5/1991 | Woodie et al. |
| 5,047,335 A | 9/1991 | Paulson et al. |
| 5,219,740 A | 6/1993 | Miller et al. |
| 5,266,575 A | 11/1993 | Gerster et al. |
| 5,268,376 A | 12/1993 | Gerster |
| 5,278,299 A | 1/1994 | Wong et al. |
| 5,346,905 A | 9/1994 | Gerster |
| 5,352,784 A | 10/1994 | Nikolaides et al. |
| 5,389,640 A | 2/1995 | Gerster et al. |
| 5,422,120 A | 6/1995 | Kim |
| 5,446,153 A | 8/1995 | Lindstrom et al. |
| 5,482,936 A | 1/1996 | Lindstrom |
| 5,500,362 A | 3/1996 | Robinson et al. |
| 5,510,261 A | 4/1996 | Goochee et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Feigner et al. |
| 5,585,089 A | 12/1996 | Queen et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,733,743 A | 3/1998 | Johnson et al. |
| 5,750,373 A | 5/1998 | Garrard et al. |

(Continued)

FOREIGN PATENT DOCUMENTS

| | | |
|---|---|---|
| EP | 0 345 242 A2 | 12/1989 |
| EP | 0 404 097 A2 | 6/1990 |

(Continued)

OTHER PUBLICATIONS

Mariuzza (Annu. Rev. Biophys. Biophys. Chem., 16: 139-159, 1987).*
Woffendin et al, "Nonviral and viral delivery of a human immunodeficiency virus protective gene into primary human T cells", Proceedings of the National Academy of Sciences of the United States of America 91:11581-11585 (1994).
Wright et al, "Effect of glycosylation on antibody function: implications for genetic engineering", Trends in Biotechnology (TibTECH) 15:26-32 (1997).
Wu et al, "Receptor-mediated Gene Delivery and Expression in Vivo", The Journal of Biological Chemistry 263 (29):14621-14624 (1988).

(Continued)

*Primary Examiner* — Nelson B Moseley, II
(74) *Attorney, Agent, or Firm* — Ye Hua; Bryan C. Zielinski

(57) ABSTRACT

The present invention provides novel antibodies that specifically bind to CD3 and uses thereof. The invention also provides therapeutic and diagnostic methods utilizing the antibodies and antigen-binding fragments provided herein.

20 Claims, 22 Drawing Sheets

Specification includes a Sequence Listing.

(56) References Cited

U.S. PATENT DOCUMENTS

| | | | |
|---|---|---|---|
| 5,756,747 A | 5/1998 | Gerster | |
| 5,807,715 A | 9/1998 | Morrison et al. | |
| 5,814,482 A | 9/1998 | Dubensky et al. | |
| 5,821,337 A | 10/1998 | Carter et al. | |
| 5,866,692 A | 2/1999 | Shitara et al. | |
| 5,997,867 A | 12/1999 | Waldmann et al. | |
| 6,028,076 A | 2/2000 | Hirota et al. | |
| 6,054,297 A | 4/2000 | Carter et al. | |
| 6,069,149 A | 5/2000 | Nanba et al. | |
| 6,110,929 A | 8/2000 | Gerster et al. | |
| 6,113,918 A | 9/2000 | Johnson et al. | |
| 6,180,370 B1 | 1/2001 | Queen et al. | |
| 6,180,377 B1 | 1/2001 | Morgan et al. | |
| 6,194,388 B1 | 2/2001 | Krieg et al. | |
| 6,194,425 B1 | 2/2001 | Gerster et al. | |
| 6,207,646 B1 | 3/2001 | Krieg et al. | |
| 6,210,671 B1 | 4/2001 | Co | |
| 6,239,116 B1 | 5/2001 | Krieg et al. | |
| 6,265,150 B1 | 7/2001 | Terstappen et al. | |
| 6,303,347 B1 | 10/2001 | Johnson et al. | |
| 6,329,381 B1 | 12/2001 | Kurimoto et al. | |
| 6,331,415 B1 | 12/2001 | Cabilly et al. | |
| 6,331,539 B1 | 12/2001 | Crooks et al. | |
| 6,339,068 B1 | 1/2002 | Krieg et al. | |
| 6,350,861 B1 | 2/2002 | Co et al. | |
| 6,376,471 B1 | 4/2002 | Lawrence et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,413,942 B1 | 7/2002 | Feigner et al. | |
| 6,426,334 B1 | 7/2002 | Agrawal et al. | |
| 6,436,908 B1 | 8/2002 | Koch et al. | |
| 6,451,810 B1 | 9/2002 | Coleman et al. | |
| 6,476,000 B1 | 11/2002 | Agrawal | |
| 6,518,265 B1 | 2/2003 | Kato et al. | |
| 6,525,028 B1 | 2/2003 | Johnson et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,573,273 B1 | 6/2003 | Crooks et al. | |
| 6,649,172 B2 | 11/2003 | Johnson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,756,382 B2 | 6/2004 | Coleman et al. | |
| 6,797,718 B2 | 9/2004 | Dellaria et al. | |
| 6,818,650 B2 | 11/2004 | Griesgraber | |
| 7,091,214 B2 | 8/2006 | Hays et al. | |
| 7,314,622 B2 | 1/2008 | Arlen et al. | |
| 7,326,414 B2 | 2/2008 | Bedian et al. | |
| 7,960,515 B2 | 6/2011 | Min et al. | |
| 8,552,165 B2 | 10/2013 | Davis et al. | |
| 8,828,401 B2 | 9/2014 | Doroski et al. | |
| 9,409,995 B2 | 8/2016 | Foord et al. | |
| 9,969,809 B2 | 5/2018 | Kuo et al. | |
| 2003/0199461 A1 | 10/2003 | Averett et al. | |
| 2004/0091491 A1 | 5/2004 | Kedl et al. | |
| 2004/0176367 A1 | 9/2004 | Griesgraber et al. | |
| 2005/0136065 A1 | 6/2005 | Valiante | |
| 2006/0100229 A1 | 5/2006 | Hays et al. | |

FOREIGN PATENT DOCUMENTS

| | | |
|---|---|---|
| EP | 0 524 968 B1 | 6/1995 |
| EP | 0 519 596 B1 | 2/2005 |
| GB | 2 200 651 B | 6/1991 |
| WO | 87/04462 A1 | 7/1987 |
| WO | 90/07936 A1 | 7/1990 |
| WO | 90/11092 A1 | 10/1990 |
| WO | 91/00904 A1 | 1/1991 |
| WO | 91/02805 A2 | 3/1991 |
| WO | 91/14445 A1 | 10/1991 |
| WO | 92/22653 A1 | 12/1992 |
| WO | 93/03769 A1 | 3/1993 |
| WO | 93/06213 A1 | 4/1993 |
| WO | 93/10218 A1 | 5/1993 |
| WO | 93/11161 A1 | 6/1993 |
| WO | 93/11230 A1 | 6/1993 |
| WO | 93/19191 A1 | 9/1993 |
| WO | 93/25234 A1 | 12/1993 |
| WO | 93/25698 A1 | 12/1993 |
| WO | 94/03622 A1 | 2/1994 |
| WO | 94/04690 A1 | 3/1994 |
| WO | 94/12649 A2 | 6/1994 |
| WO | 94/23697 A1 | 10/1994 |
| WO | 94/28938 A1 | 12/1994 |
| WO | 95/00655 A1 | 1/1995 |
| WO | 95/07994 A2 | 3/1995 |
| WO | 95/11984 A2 | 5/1995 |
| WO | 95/13796 A1 | 5/1995 |
| WO | 95/30763 A2 | 11/1995 |
| WO | 96/02555 A1 | 2/1996 |
| WO | 96/17072 A2 | 6/1996 |
| WO | 97/42338 A1 | 11/1997 |
| WO | 98/18810 A1 | 5/1998 |
| WO | 99/58572 A1 | 11/1999 |
| WO | 00/75304 A1 | 12/2000 |
| WO | 01/27160 A1 | 4/2001 |
| WO | 03/015711 A2 | 2/2003 |
| WO | 2004/016805 A2 | 2/2004 |
| WO | 2004/058184 A2 | 7/2004 |
| WO | 2005/018551 A2 | 3/2005 |
| WO | 2005/018556 A2 | 3/2005 |
| WO | 2005/020999 A1 | 3/2005 |
| WO | 2005/032484 A2 | 4/2005 |
| WO | 2005/048933 A2 | 6/2005 |
| WO | 2005/048945 A2 | 6/2005 |
| WO | 2005/051317 A2 | 6/2005 |
| WO | 2005/051324 A2 | 6/2005 |
| WO | 2005/066169 A2 | 7/2005 |
| WO | 2005/066170 A1 | 7/2005 |
| WO | 2005/066172 A1 | 7/2005 |
| WO | 2005/076783 A2 | 8/2005 |
| WO | 2005/079195 A2 | 9/2005 |
| WO | 2005/094531 A2 | 10/2005 |
| WO | 2005/123079 A2 | 12/2005 |
| WO | 2005/123080 A2 | 12/2005 |
| WO | 2006/009826 A1 | 1/2006 |
| WO | 2006/009832 A1 | 1/2006 |
| WO | 2006/026760 A2 | 3/2006 |
| WO | 2006/028451 A1 | 3/2006 |
| WO | 2006/028545 A2 | 3/2006 |
| WO | 2006/028962 A2 | 3/2006 |
| WO | 2006/029115 A2 | 3/2006 |
| WO | 2006/038923 A2 | 4/2006 |
| WO | 2006/065280 A2 | 6/2006 |
| WO | 2006/074003 A2 | 7/2006 |
| WO | 2006/083440 A2 | 8/2006 |
| WO | 2006/086449 A2 | 8/2006 |
| WO | 2006/086633 A2 | 8/2006 |
| WO | 2006/086634 A2 | 8/2006 |
| WO | 2006/091394 A2 | 8/2006 |
| WO | 2006/091567 A2 | 8/2006 |
| WO | 2006/091568 A2 | 8/2006 |
| WO | 2006/091647 A2 | 8/2006 |
| WO | 2006/093514 A2 | 9/2006 |
| WO | 2006/098852 A2 | 9/2006 |
| WO | 2009/022215 A1 | 2/2009 |
| WO | 2011/143545 A1 | 11/2011 |
| WO | 2012/059882 A2 | 5/2012 |

(56) References Cited

FOREIGN PATENT DOCUMENTS

| | | |
|---|---|---|
| WO | 2015/015448 A2 | 2/2015 |
| WO | 2016/001810 A1 | 1/2016 |
| WO | 2016/092419 A1 | 6/2016 |
| WO | 2016/166629 A1 | 10/2016 |
| WO | 2018/220584 A1 | 12/2018 |
| WO | 2018/222689 A1 | 12/2018 |

OTHER PUBLICATIONS

Wu et al, "Targeting Genes: Delivery and Persistent Expression of a Foreign Gene Driven by Mammalian Regulatory Elements in Vivo", The Journal of Biological Chemistry 264(29):16985-16987 (1989).

Wu et al, "Receptor-mediated Gene Delivery in Vivo: Partial Correction of Genetic Analbuminemia in Nagase Rats", The Journal of Biological Chemistry 266(22):14338-14342 (1991).

Wu et al,"Incorporation of Adenovirus into a Ligand-based DNA Carrier System Results in Retention of Original Receptor Specificity and Enhances Targeted Gene Expression", The Journal of Biological Chemistry 269 (15):11542-11546 (1994).

Wyss et al, "The structural role of sugars in glycoproteins", Current Opinion in Biotechnology 7:409-416 (1996).

Yelton et al, "Affinity Maturation of the BR96 Anti-Carcinoma Antibody by Codon-Based Mutagenesis", The Journal of Immunology 155:1994-2004 (1995).

Yun et al, "In Vivo Antitumor Activity of Anti-CD3-induced Activated Killer Cells", Cancer Research 49:4770-4774 (1989).

Zen Ke et al, "Receptor-mediated endocytosis of transferrin-polycation conjugates: An efficient way to introduce DNA into hematopoietic cells", Proceedings of the National Academy of Sciences of the United States of America 87:3655-3659 (1990).

Zhang et al, "Recombinase-Mediated Cassette Exchange (RMCE) for Monoclonal Antibody Expression in the Commercially Relevant CHOK1SV Cell Line", Biotechnology Progress 31(6):1645-1656 (2015).

Accession No. BAB71849, CD3 epsilon FN18+ [Macaca fascicularis]; [cited Nov. 9, 2001]. Protein [Internet]. Bethesda (MD): National Library of Medicine (US), National Center for Biotechnology Information; [1988]-[2020]. https://www.ncbi.nlm.nih.gov/protein/16874540?report=GenPept.

Accession No. NP_000724.1, T-cell surface glycoprotein CD3 epsilon chain precursor [Homo sapiens]; [cited Feb. 3, 2020]. Protein [Internet]. Bethesda (MD): National Library of Medicine (US), National Center for Biotechnology Information; [1988]-[2020]. https://www.ncbi.nlm.nih.gov/protein/NP_000724.1.

Nicolaou et al, "Calicheamicin θI(sup)1(sub): A Rationally Designed Molecule with Extremely Potent and Selective DNA Cleaving Properties and Apoptosis Inducing Activity", Angew. Chem. Int. Ed. Engl. 33(2):183-186 (1994).

UniProtKB—Q15399 (TLR1_HUMAN) Toll-like receptor 1 (Jan. 31, 2002). https://www.uniprot.org/uniprot/Q15399.

UniProtKB—O60603 (TLR2_HUMAN) Toll-like receptor 2 (Jan. 31, 2002). https://www.uniprot.org/uniprot/O60603.

UniProtKB—O15455 (TLR3_HUMAN) Toll-like receptor 3 (Jan. 31, 2002). https://www.uniprot.org/uniprot/O15455.

UniProtKB—O00206 (TLR4_HUMAN) Toll-like receptor 4 (Feb. 11, 2002). https://www.uniprot.org/uniprot/O00206.

UniProtKB—O60602 (TLR5_HUMAN) Toll-like receptor 5 (Jan. 31, 2002). https://www.uniprot.org/uniprot/O60602.

UniProtKB—Q9Y2C9 (TLR6_HUMAN) Toll-like receptor 6 (Jan. 31, 2002). https://www.uniprot.org/uniprot/Q9Y2C9.

UniProtKB—Q9NYK1 (TLR7_HUMAN) Toll-like receptor 7 (Jan. 31, 2002). https://www.uniprot.org/uniprot/Q9NYK1.

UniProtKB—Q9NR97 (TLR8_HUMAN) Toll-like receptor 8 (Jan. 31, 2002). https://www.uniprot.org/uniprot/Q9NR97.

UniProtKB—Q9NR96 (TLR9_HUMAN) Toll-like receptor 9 (Jan. 31, 2002). https://www.uniprot.org/uniprot/Q9NR96.

UniProtKB—P07766 (CD3E_HUMAN) T-cell surface glycoprotein CD3 epsilon chain (Aug. 1, 1988). https://www.uniprot.org/uniprot/P07766.

UniProtKB—Q86WV6 (STING_HUMAN) Stimulator of interferon genes protein (Jan. 9, 2007). https://www.uniprot.org/uniprot/Q86WV6.

Kaufman, "Overview of Vector Design for Mammalian Gene Expression", Molecular Biotechnology 16:151-160 (2000).

Kimura et al, "Retroviral Delivery of DNA into the Livers of Transgenic Mice Bearing Premalignant Hepatocellular Carcinomas", Human Gene Therapy 5:845-852 (1994).

Kohler et al, "Continuous cultures of fused cells secreting antibody of predefined specificity", Nature 256:495-497 (1975).

Kufer et al, "A revival of bispecific antibodies", TRENDS in Biotechnology 22(5):238-244 (2004).

Kuhn et al, "Therapeutic anti-CD3 monoclonal antibodies: from bench to bedside", Immunotherapy 8(8):889-906 (2016).

Lawrence et al, "Mutational heterogeneity in cancer and the search for new cancer-associated genes", Nature 499:214-218 (2013).

Leong et al, "An anti-CD3/CLL-1 bispecific antibody for the treatment of acute myeloid leukemia", Blood 129 (5):609-618 (2017).

Levy et al, "A Modified Polyriboinosinic-Polyribocytidylic Acid Complex That Induces Interferon in Primates", The Journal of Infectious Disease 132(4):434-439 (1975).

Lobuglio et al, "Mouse/human chimeric monoclonal antibody in man: Kinetics and immune response", Proceedings of the National Academy of Sciences of the United States of America 86:4220-4224 (1989).

Lonberg et al, "Human Antibodies from Transgenic Mice", Intern. Rev. Immunol. 13:65-93 (1995).

Lund et al, "Multiple Interactions of IgG with Its Core Oligosaccharide Can Modulate Recognition by Complement and Human Fcγ Receptor I and Influence the Synthesis of Its Oligosaccharide Chains", The Journal of Immunology 157:4963-4969 (1996).

Mac Callum et al, "Antibody-antigen Interactions: Contact Analysis and Binding Site Topography", Journal of Molecular Biology 262:732-745 (1996).

Makabe et al, "Thermodynamic Consequences of Mutations in Vernier Zone Residues of a Humanized Anti-human Epidermal Growth Factor Receptor Murine Antibody, 528", The Journal of Biological Chemistry 283(2):1156-1166 (2008).

Makrides, "Components of Vectors for Gene Transfer and Expression in Mammalian Cells", Protein Expression and Purification 17:183-202 (1999).

Marks et al, "By-passing Immunization: Human Antibodies from V-gene Libraries Displayed on Phage", J. Mol. Biol. 222:581-597 (1991).

Marks et al, "By-passing Immunization: Building High Affinity Human Antibodies by Chain Shuffling", Bio/Technology 10:779-783 (1992).

Martin et al, "Modeling antibody hypervariable loops: A combined algorithm", Proceedings of the National Academy of Sciences of the United States of America 86:9268-9272 (1989).

Mc Cafferty et al, "Phage antibodies: filamentous phage displaying antibody variable domains", Nature 348:552-554 (1990).

Milstein et al, "Hybrid hybridomas and their use in immunohistochemistry", Nature 305:537-539 (1983).

Morgan et al, "The N-terminal end of the CH2 domain of chimeric human IgG1 anti-HLA-DR is necessary for C1q, FcγRI and FcγRIII binding", Immunology 86:319-324 (1995).

Morrison et al, "Chimeric human antibody molecules: Mouse antigen-binding domains with human constant region domains", Proceedings of the National Academy of Sciences of the United States of America 81:6851-6855 (1984).

Naumann et al, "Activation of Dendritic Cells by the Novel Toll-Like Receptor 3 Agonist RGC100", Clinical and Developmental Immunology vol. 2013, Article ID 283649 (2013).

NCBI GenBank Accession No. NM_000733 Homo sapiens CD3e molecule (CD3E), mRNA (May 31, 2018).

North et al, "A New Clustering of Antibody CDR Loop Conformations", Journal of Molecular Biology 406:228-256 (2011).

(56) References Cited

OTHER PUBLICATIONS

Padlan et al, "Identification of specificity-determining residues in antibodies", FASEB Journal 9:133-139 (1995).
PCT International Search Report and Written Opinion for International Patent Application No. PCT/IB2019/054186 dated Sep. 11, 2019.
Peeters et al, "Production of antibodies and antibody fragments in plants", Vaccine 19:2756-2761 (2001).
Philip et al, "Efficient and Sustained Gene Expression in Primary T Lymphocytes and Primary and Cultured Tumor Dells Mediated by Adeno-Associated Virus Plasmid DNA Complexed to Cationic Liposomes", Molecular and Cellular Biology 14(4):2411-2418 (1994).
Pollock et al, "Transgenic milk as a method for the production of recombinant antibodies", Journal of Immunological Methods 231:147-157 (1999).
Ravetch et al, "Fc Receptors", Annu. Rev. Immunol. 9:457-492 (1991).
Riechmann et al, "Reshaping human antibodies for therapy", Nature 332:323-327 (1988).
Schier et al, "Identification of functional and structural amino-acid residues by parsimonious mutagenesis", Gene 169:147-155 (1996).
Shaw et al, "Characterization of a Mouse/Human Chimeric Monoclonal Antibody (17-1A) to a Colon Cancer Tumor-associated Antigen", The Journal of Immunology 138(12):4534-4538 (1987).
Sheets et al, "Efficient construction of a large nonimmune phage antibody library: The production of high-affinity human single-chain antibodies to protein antigens", Proceedings of the National Academy of Sciences of the United States of America 95:6157-6162 (1998).
Shields et al, "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276 (9):6591-6604 (2001).
Suresh et al, "Bispecific Monoclonal Antibodies from Hybrid Hybridomas", Methods in Enzymology 121:210-228 (1986).
Tanaka et al, "N-terminal glycine-specific protein conjugation catalyzed by microbial transglutominase", FEBS Letters 679:2092-2096 (2005).
Tao et al, "Studies of Aglycosylated Chimeric Mouse-Human IgG: Role of Carbohydrate in the Structure and Effector Functions Mediated by the Human IgG Constant Region", The Journal of Immunology 143(8):2595-2601 (1989).
Taylor et al, "A transgenic mouse that expresses a diversity of human sequence heavy and light chain immunoglobulins", Nucleic Acids Research 20(23):6287-6295 (1992).
Tiller et al, "Efficient generation of monoclonal antibodies from single human B cells by single cell RT-PCR and axpression vector cloning", Journal of Immunological Methods 329:112-124 (2008).
Tutt et al, "Trispecific F(ab')3 Derivatives That Use Cooperative Signaling Via The TCR/CD3 Complex and CD2 To Activate and Redirect Resting Cytotoxic T Cells", The Journal of Immunology 147(1):60-69 (1991).
Umana et al, "Engineered glycoforms of an antineuroblastoma IgG1 with optimized antibody-dependent cellular cytotoxic aclivily", Nature Biotechnology 17:176-180 (1999).
Vaughan et al, "Human Antibodies with Sub-nanomolar Affinities Isolated from a Large Non-immunized Phage Display Library", Nature Biotechnology 14:309-314 (1996).
Verhoeyen et al, "Reshaping Human Antibodies: Grafting an Antilysozyme Activity", Science 239:1534-1536 (1988).
Vogelstein et al, "Cancer Genome Landscapes", Science 339:1546-1558 (2013).
Ward et al, "Binding activities of a repertoire of single immunoglobulin variable domains secreted from *Escherichia coli*", Nature 341:544-546 (1989).
Waterhouse et al, "Combinatorial infection and in vivo recombination: a strategy for making large phage antibody repertoires", Nucleic Acids Research 21(9):2265-2266 (1993).

Winter et al, "Man-made antibodies", Nature 349:293-299 (1991).
Winter et al, "Making Antibodies by Phage Display Technology", Ann. Rev. Immunol. 12:433-455 (1994).
Wittwer et al, "Glycosylation at Asn-184 Inhibits the Conversion of Single-Chain to Two-Chain Tissue-Type Plasminogen Activator by Plasmin", Biochemistry 29:4175-4180 (1990).
Al-Lazikani et al, "Standard Conformations for the Canonical Structures of Immunoglobulins", J. Mol Biol. 273:927-948 (1997).
Alexandrov et al,"Signatures of mutational processes in human cancer", Nature 500:415-421 (2013).
Armour et al, "Recombinant human IgG molecules lacking Fcgamma receptor I binding and monocyte triggering activities", Eur. J. Immunol. 29:2613-2624 (1999).
Balint et al, "Antibody engineering by parsimonious mutagenesis", Gene 137:109-118 (1993).
Barbas et al, "In vitro evolution of a neutralizing human antibody to human immunodeficiency virus type 1 to enhance affinity and broaden strain cross-reactivity", Proceedings of the National Academy of Sciences of the United States of America 91:3809-3813 (1994).
Bird et al, "Single-Chain Antigen-Binding Proteins", Science 242:423-426 (1988).
Bloom et al, "Intrachain disulfide bond in the core hinge region of human IgG4", Protein Science 6:407-415 (1997).
Boerner et al, "Production of Antigen-Specific Human Monoclonal Antibodies from In Vitro-Primed Human Splenocytes", The Journal of Immunology 147:86-95 (1991).
Bowie et al, "Deciphering the Message in Protein Sequences: Tolerance to Amino Acid Substitutions", Science 247:1306-1310(1990).
Boyd et al, "The Effect of the Removal of Sialic Acid, Galactose and Total Carbohydrate on the Functional Activity of Dampath-1H", Molecular Immunology 32(17/18):1311-1318 (1995).
Brinkmann et al, "Phage display of disulfide-stabilized Fv fragments", Journal of Immunological Methods 182:41-50 (1995).
Brown et al, "Tumor-specific Genetically Engineered Murine/Human Chimeric Monoclonal Antibody", Cancer Research 47:3577-3583 (1987).
Buck et al, "Monoclonal Antibodies Specific for Cell Culture Mycoplasmas", In Vitro 18(4):377-381 (1982).
Canfield et al, "The Binding Affinity of Human IgG for its High Affinity Fc Receptor is Determined by Multiple Amino Acids in the CH2 Domain and is Modulated by the Hinge Region", J. Exp. Med. 173:1483-1491 (1991).
Capel et al, "Heterogeneity of Human IgG Fc Receptors", Immunomethods 4:25-34 (1994).
Chothia et al, "Conformations of immunoglobulin hypervariable regions", Nature 342:877-883 (1989).
Clackson et al, "Making antibody fragments using phage display libraries", Nature 352:624-628 (1991).
Clynes et al, "Fc receptors are required in passive and active immunity to melanoma", Proceedings of the National Academy of Sciences of the United States of America 95:652-656 (1998).
Connelly et al, "In Vivo Gene Delivery and Expression of Physiological Levels of Functional Human Factor VIII in Mice", Human Gene Therapy 6:185-193 (1995).
Curiel et al, "High-Efficiency Gene Transfer Mediated by Adenovirus Coupled to DNA-Polylysine Complexes", Human Gene Therapy 3:147-154 (1992).
Daugherty et al, "Polymerase chain reaction facilitates the cloning, CDR-grafting, and rapid expression of a murine monoclonal antibody directed against the CD18 component of leukocyte integrins", Nucleic Acids Research 19 (9):2471-2476 (1991).
De Haas et al, "Fcγ receptors of phagocytes", J Lab Clin Med 126:330-341 (1995).
Ellman et al, "Biosynthetic Method for Introducing Unnatural Amino Acids Site-Specifically into Proteins", Methods in Enzymology 202:301-336 (1991).
Eppstein et al, "Biological activity of liposome-encapsulated murine interferon γ is mediated by a cell membrane Yeceptor", Proceedings of the National Academy of Sciences of the United States of America 82:3688-3692 (1985).
Findeis et al, "Targeted delivery of DNA for gene therapy via receptors", Trends in Biotechnology 11(5):202-205 (1993).

(56) References Cited

OTHER PUBLICATIONS

Gazzano-Santoro et al, "A non-radioactive complement-dependent cytotoxicity assay for anti-CD20 monoclonal antibody", Journal of Immunological Methods 202:163-171 (1997).
Geisse et al, "Eukaryotic Expression Systems: A Comparison", Protein Expression and Purification 8:271-282 (1996).
Gentle et al, "Direct Production of Proteins with N-Terminal Cysteine for Site-Specific Conjugation", Bioconjugate Chem. 15:658-663 (2004).
Griffiths et al, "Human anti-self antibodies with high specificity from phage display libraries", The EMBO Journal 12 (2):725-734 (1993).
Guyer et al, "Immunoglobulin Binding by Mouse Intestinal Epithelial Cell Receptors", The Journal of Immunology 117 (2):587-593 (1976).
Hawkins et al, "Selection of Phage Antibodies by Binding Affinity: Mimicking Affinity Maturation", J. Mol. Biol. 226:889-896 (1992).
Heil et al, "Species-Specific Recognition of Single-Stranded RNA via Toll-like Receptor 7 and 8", Science 303 (5663):1526-1529 (2004).
Holliger et al, ""Diabodies": Small bivalent and bispecific antibody fragments", Proceedings of the National Academy of Sciences of the United States of America 90:6444-6448 (1993).
Hoogenboom et al, "By-passing Immunisation: Human Antibodies from Synthetic Repertoires of Germline VH Gene Segments Rearranged in Vitro", J. Mol. Biol. 227:381-388 (1992).
Hsu et al, "Differential N-Glycan Patterns of Secreted and Intracellular IgG Produced in Trichoplusia ni Cells", The Journal of Biological Chemistry 272(14):9062-9070 (1997).
Humphreys et al, "Formation of dimeric Fabs in *Escherichia coli*: effect of hinge size and isotype, presence of nterchain disulphide bond, Fab' expression levels, tail piece sequences and growth conditions", Journal of mmunological Methods 209:193-202 (1997).
Huston et al, "Protein engineering of antibody binding sites: Recovery of specific activity in an anti-digoxin singlechain Fv analogue produced in *Escherichia coli*", Proceedings of the National Academy of Sciences of the United States of America 85:5879-5883 (1988).
Hwang et al, "Hepatic uptake and degradation of unilamellar sphingomyelin/cholesterol liposomes: A kinetic study", Proceedings of the National Academy of Sciences of the United States of America 77(7):4030-4034 (1980).
Dusogie et al, "Mapping of the C1q Binding Site on Rituxan, a Chimeric Antibody with a Human IgG1 Fc", The Journal of Immunology 164:4178-4184 (2000).
Jackson et al, "In Vitro Antibody Maturation", The Journal of Immunology 154:3310-3319 (1995).
Jakobovits et al, "Germ-line transmission and expression of a human-derived yeast artificial chromosome", Nature 362:255-258 (1993).
Jakobovits et al, "Analysis of homozygous mutant chimeric mice: Deletion of the immunoglobulin heavy-chain oining region blocks B-cell development and antibody production", Proceedings of the National Academy of Sciences of the United States of America 90:2551-2555 (1993).
Jasani et al, "Ampligen: A potential toll-like 3 receptor adjuvant for immunotherapy of cancer", Vaccine 27 (25-26):3401-3404 (2009).
Jefferis et al, "Glycosylation of Antibody Molecules: Structural and Functional Significance", Chem. Immunol. 65:111-128 (1997).
Jefferis et al, "IgG-Fc-mediated effector functions: molecular definition of interaction sites for effector ligands and the role of glycosylation", Immunological Reviews 163:59-76 (1998).
Jin et al, "Synthesis and immunostimulatory activity of 8-substituted amino 9-benzyladenines as potent Toll-like receptor 7 agonists", Bioorganic& Medicinal Chemistry Letters 16(17):4559-4563 (2006).
Jolly, "Viral vector systems for gene therapy", Cancer Gene Therapy 1(1):51-64 (1994).
Jones et al, "Replacing the complementarity-determining regions in a human antibody with those from a mouse", Nature 321:522-525 (1986).
Junutula et al, "Site-specific conjugation of a cytotoxic drug to an antibody improves the therapeutic index", Nature Biotechnology 26(8):925-932 (2008).
Kaplitt et al, "Long-term gene expression and phenotypic correction using adeno-associated virus vectors in the mammalian brain", Nature Genetics 8:148-154 (1994).

\* cited by examiner

Binding to naive human T cells

GUCY2c-1608 binding to naive human T cells

PDX-CRX-11201

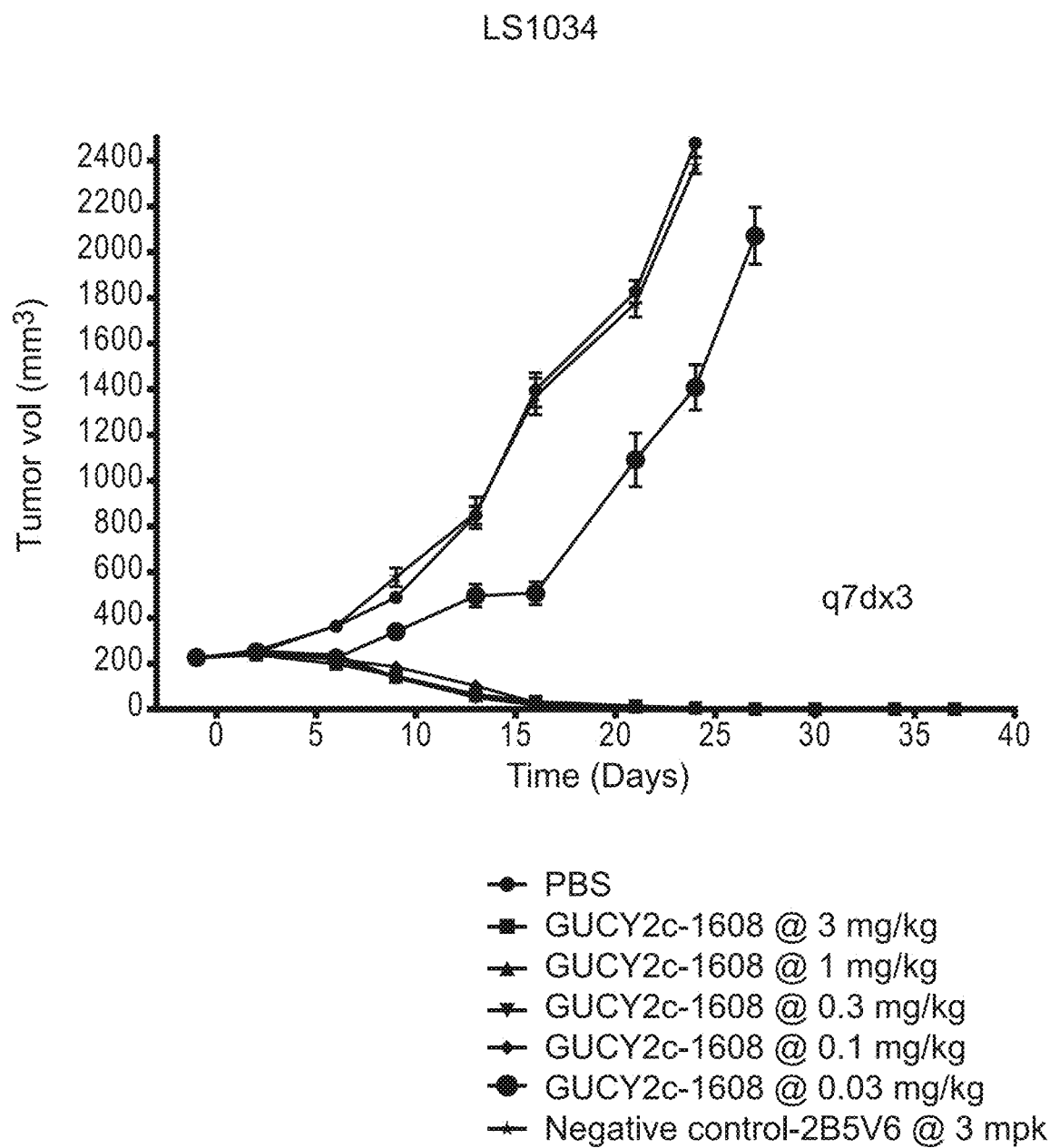

MV4-11 vs. 2B5v6

EOL-1 vs. 2B5v6

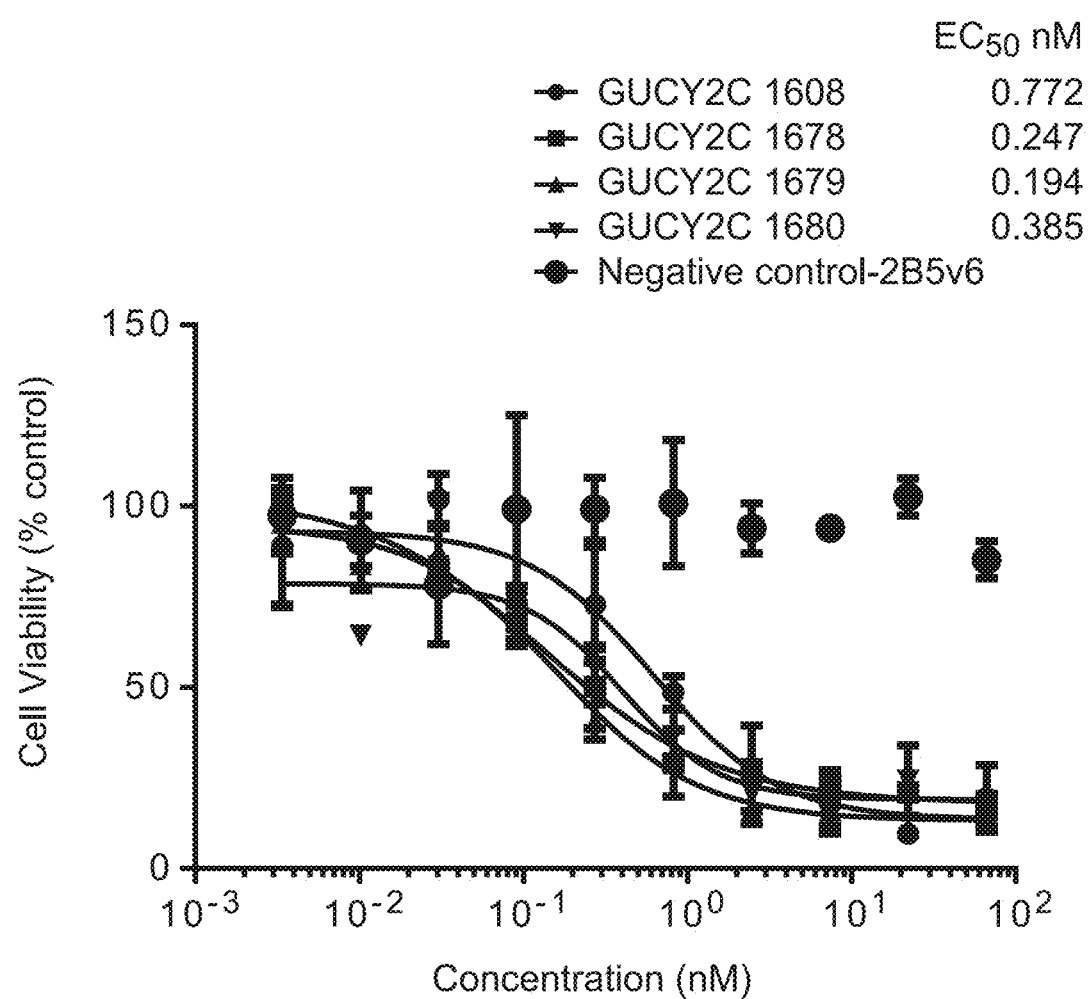

SEQUENCE LISTING

<160> NUMBER OF SEQ ID NOS: 100

<210> SEQ ID NO 1
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Thr Ser Gln Ser Leu Phe Asn Val
            20                  25                  30

Arg Ser Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 2
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser

<210> SEQ ID NO 3
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110
```

<210> SEQ ID NO 4
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120
```

<210> SEQ ID NO 5
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 5

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Tyr
                20                  25                  30

Tyr Met Thr Trp Val Arg Gln Ala Pro Gly Lys Gly Leu Glu Trp Val
            35                  40                  45

Ala Phe Ile Arg Asn Arg Ala Gln Gly Tyr Thr Ser Asp His Asn Pro
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120

<210> SEQ ID NO 6
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
                20                  25                  30

Arg Ser Gly Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 7
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Thr Trp Val Arg Gln Ala Pro Gly Lys Gly Leu Glu Trp Val
            35                  40                  45

Ala Phe Ile Arg Asn Gln Ala Arg Gly Tyr Thr Ser Asp His Gln Pro
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr

```
                    85                  90                  95
Tyr Cys Ala Arg Asp Arg Pro Ser Tyr Tyr Val Leu Asp Tyr Trp Gly
                100                 105                 110

Gln Gly Thr Thr Val Thr Val Ser Ser
        115                 120

<210> SEQ ID NO 8
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Thr Ser Asp Gln Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 10
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 10
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Asp Arg Gly Tyr Thr Ser Asp His Gln Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
            115                 120

<210> SEQ ID NO 11
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Tyr Leu Phe Thr Phe Gly Gly Gly Thr Lys Val Glu Ile Lys
            100                 105                 110

<210> SEQ ID NO 12
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Ala Arg Gly Tyr Thr Ser Asp His Asn Pro
    50                  55                  60

Ser Val Lys Gly Arg Phe Thr Ile Ser Arg Asp Asn Ala Lys Asn Ser
```

```
                65                  70                  75                  80
Leu Tyr Leu Gln Met Asn Ser Leu Arg Ala Glu Asp Thr Ala Val Tyr
                    85                  90                  95

Tyr Cys Ala Arg Asp Arg His Ser Tyr Tyr Val Leu Asp Tyr Trp Gly
                100                 105                 110

Gln Gly Thr Thr Val Thr Val Ser Ser
        115                 120
```

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 13

```
Asp Tyr Tyr Met Thr
1               5
```

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 14

```
Gly Phe Thr Phe Ser Asp Tyr
1               5
```

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 15

```
Gly Phe Thr Phe Ser Asp Tyr Tyr Met Thr
1               5                   10
```

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 16

```
Phe Ile Arg Asn Arg Ala Arg Gly Tyr Thr Ser Asp His Asn Pro Ser
1               5                   10                  15

Val Lys Gly
```

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 17

```
Arg Asn Arg Ala Arg Gly Tyr Thr
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 18

Asp Arg Pro Ser Tyr Tyr Val Leu Asp Tyr
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 19

Phe Ile Arg Asn Gln Ala Arg Gly Tyr Thr Ser Asp His Asn Pro Ser
1               5                   10                  15

Val Lys Gly

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 20

Arg Asn Gln Ala Arg Gly Tyr Thr
1               5

<210> SEQ ID NO 21
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 21

Phe Ile Arg Asn Arg Ala Gln Gly Tyr Thr Ser Asp His Asn Pro Ser
1               5                   10                  15

Val Lys Gly

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 22

Arg Asn Arg Ala Gln Gly Tyr Thr
1               5

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 23

Phe Ile Arg Asn Gln Ala Arg Gly Tyr Thr Ser Asp His Gln Pro Ser
```

-continued

```
1               5                   10                  15

Val Lys Gly

<210> SEQ ID NO 24
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 24

Phe Ile Arg Asn Gln Asp Arg Gly Tyr Thr Ser Asp His Gln Pro Ser
1               5                   10                  15

Val Lys Gly

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 25

Asp Arg His Ser Tyr Tyr Val Leu Asp Tyr
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 26

Thr Ser Ser Gln Ser Leu Phe Asn Val Arg Ser Arg Lys Asn Tyr Leu
1               5                   10                  15

Ala

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 27

Trp Ala Ser Thr Arg Glu Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 28

Lys Gln Ser Tyr Asp Leu Phe Thr
1               5

<210> SEQ ID NO 29
<211> LENGTH: 17
<212> TYPE: PRT
<213> ORGANISM: Artificial Seuqence
<220> FEATURE:
```

```
<223> OTHER INFORMATION: Synthetic peptide sequence

<400> SEQUENCE: 29

Thr Ser Ser Gln Ser Leu Phe Asn Val Arg Ser Gln Lys Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 30

Thr Ser Ser Gln Ser Leu Phe Asn Val Arg Ser Gly Lys Asn Tyr Leu
1               5                   10                  15

Ala

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 31

Trp Ala Ser Asp Arg Glu Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 32

Thr Ser Asp Gln Ser Leu Phe Asn Val Arg Ser Gly Lys Asn Tyr Leu
1               5                   10                  15

Ala

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 33

Lys Gln Ser Tyr Tyr Leu Phe Thr
1               5

<210> SEQ ID NO 34
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
```

```
                    20                  25                  30

Arg Ser Arg Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                    85                  90                  95

Ser Tyr Asp Leu Phe Thr Phe Gly Gly Gly Thr Lys Val Glu Ile Lys
                100                 105                 110

<210> SEQ ID NO 35
<211> LENGTH: 121
<212> TYPE: PRT
<213> ORGANISM: Artificial Sequence
<220> FEATURE:
<223> OTHER INFORMATION: Synthetic peptide sequence

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Tyr Met Thr Trp Val Arg Gln Ala Pro Gly Lys Gly Leu Glu Trp Val
            35                  40                  45

Ala Phe Ile Arg Asn Gln Ala Arg Gly Tyr Thr Ser Asp His Asn Pro
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
                100                 105                 110

Gln Gly Thr Thr Val Thr Val Ser Ser
        115                 120

<210> SEQ ID NO 36
<211> LENGTH: 461
<212> TYPE: PRT
<213> ORGANISM: Artificial Sequence
<220> FEATURE:
<223> OTHER INFORMATION: Synthetic peptide sequence

<400> SEQUENCE: 36

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Ser Val Asp Tyr Tyr
                20                  25                  30

Gly Thr Ser Leu Met Gln Trp Tyr Gln Gln Lys Pro Gly Lys Pro Pro
            35                  40                  45

Lys Leu Leu Ile Tyr Ala Ala Ser Asn Val Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Thr Arg
                85                  90                  95
```

Lys Val Tyr Thr Phe Gly Gln Gly Thr Lys Leu Glu Ile Lys Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Asp Tyr Tyr Met Thr Trp Val Arg Gln Ala Pro Gly
145                 150                 155                 160

Lys Gly Leu Glu Trp Val Ala Phe Ile Arg Asn Arg Ala Arg Gly Tyr
                165                 170                 175

Thr Ser Asp His Asn Pro Ser Val Lys Gly Arg Phe Thr Ile Ser Arg
            180                 185                 190

Asp Asn Ala Lys Asn Ser Leu Tyr Leu Gln Met Asn Ser Leu Arg Ala
        195                 200                 205

Glu Asp Thr Ala Val Tyr Tyr Cys Ala Arg Asp Arg Pro Ser Tyr Tyr
    210                 215                 220

Val Leu Asp Tyr Trp Gly Gln Gly Thr Thr Val Thr Val Ser Ser Gly
225                 230                 235                 240

Cys Pro Pro Cys Pro Ala Pro Glu Ala Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Cys Thr Leu Pro Pro
        355                 360                 365

Ser Arg Glu Glu Met Thr Lys Asn Gln Val Ser Leu Trp Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly
    450                 455                 460

<210> SEQ ID NO 37
<211> LENGTH: 464
<212> TYPE: PRT
<213> ORGANISM: Artificial Sequence
<220> FEATURE:
<223> OTHER INFORMATION: Synthetic peptide sequence

<400> SEQUENCE: 37

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Asn Val
            20                  25                  30
Arg Ser Arg Lys Asn Tyr Leu Ala Trp Tyr Gln Gln Lys Pro Gly Gln
        35                  40                  45
Pro Pro Lys Leu Leu Ile Ser Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                85                  90                  95
Ser Tyr Asp Leu Phe Thr Phe Gly Ser Gly Thr Lys Leu Glu Ile Lys
            100                 105                 110
Gly Gly Gly Ser Gly Gly Gly Gly Glu Val Gln Leu Val Glu Ser Gly
        115                 120                 125
Gly Gly Leu Val Gln Pro Gly Gly Ser Leu Arg Leu Ser Cys Ala Ala
    130                 135                 140
Ser Gly Tyr Thr Phe Thr Ser Tyr Trp Met His Trp Val Arg Gln Ala
145                 150                 155                 160
Pro Gly Lys Gly Leu Glu Trp Ile Gly Glu Ile Lys Pro Ser Asn Gly
                165                 170                 175
Leu Thr Asn Tyr Ile Glu Lys Phe Lys Asn Arg Phe Thr Ile Ser Val
            180                 185                 190
Asp Lys Ala Lys Asn Ser Ala Tyr Leu Gln Met Asn Ser Leu Arg Ala
        195                 200                 205
Glu Asp Thr Ala Val Tyr Tyr Cys Thr Arg Thr Ile Thr Thr Thr Glu
    210                 215                 220
Gly Tyr Trp Phe Phe Asp Val Trp Gly Gln Gly Thr Leu Val Thr Val
225                 230                 235                 240
Ser Ser Gly Cys Pro Pro Cys Pro Ala Pro Glu Ala Ala Gly Ala Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Cys Arg Glu Glu Met Thr Lys Asn Gln Val Ser Leu Ser
    370                 375                 380
Cys Ala Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Val Ser Lys Leu Thr Val Asp Lys
```

-continued

```
                420                 425                 430
Ser Arg Trp Gln Gln Gly Asn Val Phe Ser Cys Ser Val Met His Glu
            435                 440                 445
Ala Leu His Asn His Tyr Thr Gln Lys Ser Leu Ser Leu Ser Pro Gly
        450                 455                 460

<210> SEQ ID NO 38
<211> LENGTH: 464
<212> TYPE: PRT
<213> ORGANISM: Artificial Sequence
<220> FEATURE:
<223> OTHER INFORMATION: Synthetic peptide sequence

<400> SEQUENCE: 38

Asp Ile Gln Met Thr Gln Ser Pro Ser Ser Leu Ser Ala Ser Val Gly
1               5                  10                  15
Asp Arg Val Thr Ile Thr Cys Thr Ser Ser Gln Ser Leu Phe Asn Val
            20                  25                  30
Arg Ser Arg Lys Asn Tyr Leu Ala Trp Tyr Gln Gln Lys Pro Gly Lys
        35                  40                  45
Ala Pro Lys Leu Leu Ile Tyr Trp Ala Ser Thr Arg Glu Ser Gly Val
    50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Lys Gln
                85                  90                  95
Ser Tyr Asp Leu Phe Thr Phe Gly Gly Gly Thr Lys Val Glu Ile Lys
            100                 105                 110
Gly Gly Gly Ser Gly Gly Gly Gly Glu Val Gln Leu Val Glu Ser Gly
        115                 120                 125
Gly Gly Leu Val Gln Pro Gly Gly Ser Leu Arg Leu Ser Cys Ala Ala
    130                 135                 140
Ser Gly Tyr Thr Phe Thr Ser Tyr Trp Met His Trp Val Arg Gln Ala
145                 150                 155                 160
Pro Gly Lys Gly Leu Glu Trp Ile Gly Glu Ile Lys Pro Ser Asn Gly
                165                 170                 175
Leu Thr Asn Tyr Ile Glu Lys Phe Lys Asn Arg Phe Thr Ile Ser Val
            180                 185                 190
Asp Lys Ala Lys Asn Ser Ala Tyr Leu Gln Met Asn Ser Leu Arg Ala
        195                 200                 205
Glu Asp Thr Ala Val Tyr Tyr Cys Thr Arg Thr Ile Thr Thr Thr Glu
    210                 215                 220
Gly Tyr Trp Phe Phe Asp Val Trp Gly Gln Gly Thr Leu Val Thr Val
225                 230                 235                 240
Ser Ser Gly Cys Pro Pro Cys Pro Ala Pro Glu Ala Ala Gly Ala Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
```

```
                    325                 330                 335
Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Cys Arg Glu Glu Met Thr Lys Asn Gln Val Ser Leu Ser
            370                 375                 380

Cys Ala Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Val Ser Lys Leu Thr Val Asp Lys
                420                 425                 430

Ser Arg Trp Gln Gln Gly Asn Val Phe Ser Cys Ser Val Met His Glu
                435                 440                 445

Ala Leu His Asn His Tyr Thr Gln Lys Ser Leu Ser Leu Ser Pro Gly
                450                 455                 460

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 39

Gly Gly Gly Gly Ser Gly Gly Gly Gly Ser Gly Gly Gly Gly Ser
1               5                   10                  15

<210> SEQ ID NO 40
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 40

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Gly Gly Gly Ser Gly Gly Gly Gly Ser Gly
            115                 120                 125

Gly Gly Gly Ser Pro Ile Glu Glu Leu Glu Asp Arg Val Phe Val Asn
            130                 135                 140

Cys Asn Thr Ser Ile Thr Trp Val Glu Gly Thr Val Gly Thr Leu Leu
145                 150                 155                 160
```

```
Ser Asp Ile Thr Arg Leu Asp Leu Gly Lys Arg Ile Leu Asp Pro Arg
            165                 170                 175

Gly Ile Tyr Arg Cys Asn Gly Thr Asp Ile Tyr Lys Asp Lys Glu Ser
        180                 185                 190

Thr Val Gln Val His Tyr Arg Met Cys Gln Ser Cys Val Glu Leu Asp
        195                 200                 205

His His His His His His
    210

<210> SEQ ID NO 41
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Pro
            85                  90                  95

Thr Phe Gly Gln Gly Thr Arg Leu Glu Ile Lys
            100                 105

<210> SEQ ID NO 42
<211> LENGTH: 124
<212> TYPE: PRT
<213> ORGANISM: Artificial Sequence
<220> FEATURE:
<223> OTHER INFORMATION: Synthetic peptide sequence

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Ser Pro Ser Val Gly Trp Gly Tyr Gly Phe Asp
            100                 105                 110

Ile Trp Gly Gln Gly Thr Leu Val Thr Val Ser Ser
        115                 120

<210> SEQ ID NO 43
```

```
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 43

Ala Ala Ser Ser Leu Gln Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 44

Val Gln Pro Gly Gly Ser Leu Arg Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 45

Leu Arg Leu Ser Cys Ala Ala Ser Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 46

Trp Val Arg Gln Ala Pro Gly Lys Gly
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 47

Val Arg Gln Ala Pro Gly Lys Gly Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 48

Trp Val Ala Phe Ile Arg Asn Gln Ala
1               5

<210> SEQ ID NO 49
<211> LENGTH: 9
```

```
<212> TYPE: PRT
<213> ORGANISM: Artificial Sequence
<220> FEATURE:
<223> OTHER INFORMATION: Synthetic peptide sequence

<400> SEQUENCE: 49

Phe Ile Arg Asn Gln Ala Arg Gly Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 50

Tyr Thr Ser Asp His Asn Pro Ser Val
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 51

Val Lys Gly Arg Phe Thr Ile Ser Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 52

Phe Thr Ile Ser Arg Asp Asn Ala Lys
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 53

Leu Tyr Leu Gln Met Asn Ser Leu Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 54

Tyr Leu Gln Met Asn Ser Leu Arg Ala
1               5

<210> SEQ ID NO 55
<211> LENGTH: 9
<212> TYPE: PRT
```

```
<213> ORGANISM: Artificial Sequence
<220> FEATURE:
<223> OTHER INFORMATION: Synthetic peptide sequence

<400> SEQUENCE: 55

Leu Gln Met Asn Ser Leu Arg Ala Glu
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 56

Ile Gln Met Thr Gln Ser Pro Ser Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 57

Met Thr Gln Ser Pro Ser Ser Leu Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 58

Ile Thr Cys Thr Ser Ser Gln Ser Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 59

Val Arg Ser Gln Lys Asn Tyr Leu Ala
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 60

Trp Tyr Gln Gln Lys Pro Gly Lys Ala
1               5

<210> SEQ ID NO 61
<211> LENGTH: 9
<212> TYPE: PRT
<213> ORGANISM: Artificial Sequence
```

<220> FEATURE:
<223> OTHER INFORMATION: Synthetic peptide sequence

<400> SEQUENCE: 61

Leu Leu Ile Tyr Trp Ala Ser Thr Arg
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 62

Phe Thr Leu Thr Ile Ser Ser Leu Gln
1               5

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 63

Glu Pro Lys Ser Cys Asp Lys Thr His Thr Cys Pro Pro Cys Pro
1               5                   10                  15

<210> SEQ ID NO 64
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 64

Cys Pro Pro Cys Pro
1               5

<210> SEQ ID NO 65
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 65

Gly Gly Gly Gly Ser Gly Gly Gly Ser Gly Gly Gly Gly Ser Gly
1               5                   10                  15

<210> SEQ ID NO 66
<211> LENGTH: 186
<212> TYPE: PRT
<213> ORGANISM: Homo sapiens

<400> SEQUENCE: 66

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
        50                  55                  60

```
Glu Phe Ser Glu Leu Glu Gln Ser Gly Tyr Tyr Val Cys Tyr Pro Arg
 65                  70                  75                  80

Gly Ser Lys Pro Glu Asp Ala Asn Phe Tyr Leu Tyr Leu Arg Ala Arg
                 85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
                180                 185

<210> SEQ ID NO 67
<211> LENGTH: 1534
<212> TYPE: DNA
<213> ORGANISM: Homo sapiens

<400> SEQUENCE: 67
tattgtcaga gtcctcttgt ttggccttct aggaaggctg tgggacccag ctttcttcaa      60
ccagtccagg tggaggcctc tgccttgaac gtttccaagt gaggtaaaac ccgcaggccc     120
agaggcctct ctacttcctg tgtggggttc agaaaccctc ctcccctccc agcctcaggt     180
gcctgcttca gaaaatgaag tagtaagtct gctggcctcc gccatcttag taaagtaaca     240
gtcccatgaa acaaagatgc agtcgggcac tcactggaga gttctgggcc tctgcctctt     300
atcagttggc gtttgggggc aagatggtaa tgaagaaatg ggtggtatta cacagacacc     360
atataaagtc tccatctctg gaaccacagt aatattgaca tgccctcagt atcctggatc     420
tgaaatacta tggcaacaca atgataaaaa cataggcggt gatgaggatg ataaaaacat     480
aggcagtgat gaggatcacc tgtcactgaa ggaattttca gaattggagc aaagtggtta     540
ttatgtctgc taccccagag gaagcaaacc agaagatgcg aacttttatc tctacctgag     600
ggcaagagtg tgtgagaact gcatggagat ggatgtgatg tcggtggcca caattgtcat     660
agtggacatc tgcatcactg ggggcttgct gctgctggtt tactactgga gcaagaatag     720
aaaggccaag gccaagcctg tgacacgagg agcgggtgct ggcggcaggc aaaggggaca     780
aaacaaggag aggccaccac ctgttcccaa cccagactat gagcccatcc ggaaaggcca     840
gcgggacctg tattctggcc tgaatcagag acgcatctga ccctctggag aacactgcct     900
cccgctggcc caggtctcct ctccagtccc cctgcgactc cctgtttcct gggctagtct     960
tggaccccac gagagagaat cgttcctcag cctcatggtg aactcgcgcc ctccagcctg    1020 atccccgct ccctcctccc tgccttctct gctggtaccc agtcctaaaa tattgctgct    1080
tcctcttcct ttgaagcatc atcagtagtc acaccctcac agctggcctg ccctcttgcc    1140
aggatattta tttgtgctat tcactccctt ccctttggat gtaacttctc cgttcagttc    1200 cctcctttc ttgcatgtaa gttgtccccc atcccaaagt attccatcta cttttctatc    1260 gccgtccct tttgcagccc tctctgggga tggactgggg aaatgttgac agaggccctg    1320
ccccgttcac agatcctggc cctgagccag ccctgtgctc ctccctcccc caacactccc    1380
```

| | |
|---|---|
| taccaacccc ctaatcccct actccctcca cccccctcc actgtaggcc actggatggt | 1440 |
| catttgcatc tccgtaaatg tgctctgctc ctcagctgag agagaaaaaa ataaactgta | 1500 |
| tttggctgca agaaaaaaaa aaaaaaaaaa aaaa | 1534 |

<210> SEQ ID NO 68
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 68

| | |
|---|---|
| gacatccaga tgacccagtc ccctcttct ctgtctgcct ctgtgggcga cagagtgacc | 60 |
| atcacctgca caagctcaca gtcactgttt aatgtccgca gccggaaaaa ctatcttgcg | 120 |
| tggtatcagc agaagcctgg caaggctccc aagctgctga tctactgggc cagtacacga | 180 |
| gaatccggcg tgccttccag attctccggc tctggctctg gcaccgattt caccctgacc | 240 |
| atctcctccc tccagcctga ggatttcgcc acctactact gcaaacagtc ttacgacctt | 300 |
| ttcacttttg gcggcggaac aaaggtggag atcaag | 336 |

<210> SEQ ID NO 69
<211> LENGTH: 363
<212> TYPE: DNA
<213> ORGANISM: Artificial Sequence
<220> FEATURE:
<223> OTHER INFORMATION: Synthetic nucleotide sequence

<400> SEQUENCE: 69

| | |
|---|---|
| gaagtgcagc ttgttgaatc tggcggcggt ttggttcagc ccggtggatc actgcgactc | 60 |
| agttgcgcag ctagcggctt caccttttct gattactaca tgacatgggt acgacaggcg | 120 |
| ccaggcaagg gtttggaatg gtagcattc atacgcaata gggcacgcgg gtacacttca | 180 |
| gaccacaatc cctcagtaaa aggaagattt accatctcaa gagacaatgc caaaaattca | 240 |
| ctctacctgc aaatgaactc acttcgcgcc gaggataccg ccgtgtatta ctgtgccaga | 300 |
| gacagaccat cttattacgt gctggactat tggggacagg gcactacagt caccgtcagc | 360 |
| tct | 363 |

<210> SEQ ID NO 70
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 70

| | |
|---|---|
| gacatccaga tgacccagtc ccctcttct ctgtctgcct ctgtgggcga cagagtgacc | 60 |
| atcacctgca caagctcaca gtcactgttt aatgtccgca gccagaaaaa ctatcttgcg | 120 |
| tggtatcagc agaagcctgg caaggctccc aagctgctga tctactgggc cagtacacga | 180 |
| gaatccggcg tgccttccag attctccggc tctggctctg gcaccgattt caccctgacc | 240 |
| atctcctccc tccagcctga ggatttcgcc acctactact gcaaacagtc ttacgacctt | 300 |
| ttcacttttg gcggcggaac aaaggtggag atcaag | 336 |

<210> SEQ ID NO 71
<211> LENGTH: 363
<212> TYPE: DNA
<213> ORGANISM: Artificial Sequence

```
<220> FEATURE:
<223> OTHER INFORMATION: Synthetic nucleotide sequence

<400> SEQUENCE: 71
gaagtgcagc ttgttgaatc tggcggcggt ttggttcagc ccggtggatc actgcgactc      60
agttgcgcag ctagcggctt cacctttttct gattactaca tgcatgggt acgacaggcg     120 ccaggcaagg gtttggaatg ggtagcattc atacgcaatc aggcacgcgg gtacacttca     180
gaccacaatc cctcagtaaa aggaagattt accatctcaa gagacaatgc caaaaattca     240
ctctacctgc aaatgaactc acttcgcgcc gaggataccg ccgtgtatta ctgtgccaga     300
gacagaccat cttattacgt gctggactat tggggacagg gcactacagt caccgtcagc     360
tct                                                                    363

<210> SEQ ID NO 72
<211> LENGTH: 363
<212> TYPE: DNA
<213> ORGANISM: Artificial Sequence
<220> FEATURE:
<223> OTHER INFORMATION: Synthetic nucleotide sequence

<400> SEQUENCE: 72
gaagtgcagc ttgttgaatc tggcggcggt ttggttcagc ccggtggatc actgcgactc      60
agttgcgcag ctagcggctt cacctttttct gattactaca tgcatgggt acgacaggcg     120 ccaggcaagg gtttggaatg ggtagcattc atacgcaata gggcacaggg gtacacttca     180
gaccacaatc cctcagtaaa aggaagattt accatctcaa gagacaatgc caaaaattca     240
ctctacctgc aaatgaactc acttcgcgcc gaggataccg ccgtgtatta ctgtgccaga     300
gacagaccat cttattacgt gctggactat tggggacagg gcactacagt caccgtcagc     360
tct                                                                    363

<210> SEQ ID NO 73
<211> LENGTH: 363
<212> TYPE: DNA
<213> ORGANISM: Artificial Sequence
<220> FEATURE:
<223> OTHER INFORMATION: Synthetic nucleotide sequence

<400> SEQUENCE: 73
gaagtgcagc ttgttgaatc tggcggcggt ttggttcagc ccggtggatc actgcgactc      60
agttgcgcag ctagcggctt cacctttttct gattactaca tgcatgggt acgacaggcg     120 ccaggcaagg gtttggaatg ggtagcattc atacgcaatc aggcacgcgg gtacacttca     180
gaccaccagc cctcagtaaa aggaagattt accatctcaa gagacaatgc caaaaattca     240
ctctacctgc aaatgaactc acttcgcgcc gaggataccg ccgtgtatta ctgtgccaga     300
gacagaccat cttattacgt gctggactat tggggacagg gcactacagt caccgtcagc     360
tct                                                                    363

<210> SEQ ID NO 74
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 74
gacatccaga tgacccagtc cccctcttct ctgtctgcct ctgtgggcga cagagtgacc      60
```

```
atcacctgca caagctcaca gtcactgttt aatgtccgca gccagaaaaa ctatcttgcg      120
tggtatcagc agaagcctgg caaggctccc aagctgctga tctactgggc cagtgatcga      180
gaatccggcg tgccttccag attctccggc tctggctctg gcaccgattt caccctgacc      240
atctcctccc tccagcctga ggatttcgcc acctactact gcaaacagtc ttacgacctt      300 ttcactttg gcggcggaac aaaggtggag atcaag                                 336
```

<210> SEQ ID NO 75
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 75

```
gacatccaga tgacccagtc cccctcttct ctgtctgcct ctgtgggcga cagagtgacc       60
atcacctgca caagcgacca gtcactgttt aatgtccgca gcggcaaaaa ctatcttgcg      120
tggtatcagc agaagcctgg caaggctccc aagctgctga tctactgggc cagtgaccga      180
gaatccggcg tgccttccag attctccggc tctggctctg gcaccgattt caccctgacc      240
atctcctccc tccagcctga ggatttcgcc acctactact gcaaacagtc ttacgacctt      300 ttcactttg gcggcggaac aaaggtggag atcaag                                 336
```

<210> SEQ ID NO 76
<211> LENGTH: 363
<212> TYPE: DNA
<213> ORGANISM: Artificial Sequence
<220> FEATURE:
<223> OTHER INFORMATION: Synthetic nucleotide sequence

<400> SEQUENCE: 76

```
gaagtgcagc ttgttgaatc tggcggcggt ttggttcagc ccggtggatc actgcgactc       60
agttgcgcag ctagcggctt cacctttttct gattactaca tgacatgggt acgacaggcg      120
ccaggcaagg gtttggaatg ggtagcattc atacgcaatc aggaccgcgg gtacacttca      180
gaccaccagc cctcagtaaa aggaagattt accatctcaa gagacaatgc caaaaattca      240
ctctacctgc aaatgaactc acttcgcgcc gaggataccg ccgtgtatta ctgtgccaga      300
gacagaccat cttattacgt gctggactat tggggacagg gcactacagt caccgtcagc      360
tct                                                                     363
```

<210> SEQ ID NO 77
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 77

```
gacatccaga tgacccagtc cccctcttct ctgtctgcct ctgtgggcga cagagtgacc       60
atcacctgca caagctcaca gtcactgttt aatgtccgca gccagaaaaa ctatcttgcg      120
tggtatcagc agaagcctgg caaggctccc aagctgctga tctactgggc cagtacacga      180
gaatccggcg tgccttccag attctccggc tctggctctg gcaccgattt caccctgacc      240
atctcctccc tccagcctga ggatttcgcc acctactact gcaaacagtc ttactacctt      300 ttcactttg gcggcggaac aaaggtggag atcaag                                 336
```

```
<210> SEQ ID NO 78
<211> LENGTH: 216
<212> TYPE: PRT
<213> ORGANISM: Artificial Sequence
<220> FEATURE:
<223> OTHER INFORMATION: Synthetic peptide sequence

<400> SEQUENCE: 78

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 79
<211> LENGTH: 216
<212> TYPE: PRT
<213> ORGANISM: Artificial Sequence
<220> FEATURE:
<223> OTHER INFORMATION: Synthetic peptide sequence

<400> SEQUENCE: 79

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 80
<211> LENGTH: 326
<212> TYPE: PRT
<213> ORGANISM: Artificial Sequence
<220> FEATURE:
<223> OTHER INFORMATION: Synthetic peptide sequence

<400> SEQUENCE: 80

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

Gln Val Ser Leu Thr Cys Leu Val Lys Gly Phe Tyr Pro Ser Asp Ile
                      245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 81
<211> LENGTH: 326
<212> TYPE: PRT
<213> ORGANISM: Artificial Sequence
<220> FEATURE:
<223> OTHER INFORMATION: Synthetic peptide sequence

<400> SEQUENCE: 81

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 82
<211> LENGTH: 216
<212> TYPE: PRT
<213> ORGANISM: Artificial Sequence
<220> FEATURE:
<223> OTHER INFORMATION: Synthetic peptide sequence

<400> SEQUENCE: 82

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 83
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 83
gacatccaga tgacccagtc ccctctcttct ctgtctgcct ctgtgggcga cagagtgacc      60
atcacctgca aagctcaca gtcactgttt aatgtccgca gcggaaaaaa ctatcttgcg      120
tggtatcagc agaagcctgg caaggctccc aagctgctga tctactgggc cagtacacga     180
```

```
gaatccggcg tgccttccag attctccggc tctggctctg gcaccgattt caccctgacc    240
atctcctccc tccagcctga ggatttcgcc acctactact gcaaacagtc ttacgacctt    300 ttcactttg gcggcggaac aaaggtggag atcaag                               336
```

<210> SEQ ID NO 84
<211> LENGTH: 363
<212> TYPE: DNA
<213> ORGANISM: Artificial Sequence
<220> FEATURE:
<223> OTHER INFORMATION: Synthetic nucleotide sequence

<400> SEQUENCE: 84

```
gaagtgcagc ttgttgaatc tggcggcggt ttggttcagc ccggtggatc actgcgactc     60
agttgcgcag ctagcggctt caccttttct gattactaca tgacatgggt acgacaggcg    120
ccaggcaagg gtttggaatg gtagcattc atacgcaatc aggcacgcgg gtacacttca    180
gaccacaatc cctcagtaaa aggaagattt accatctcaa gagacaatgc caaaaattca    240
ctctacctgc aaatgaactc acttcgcgcc gaggataccg ccgtgtatta ctgtgccaga    300
gacagacact cttattacgt gctggactat tggggacagg gcactacagt caccgtcagc    360
tct                                                                  363
```

<210> SEQ ID NO 85
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 85

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110
```

<210> SEQ ID NO 86
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 86

```
gacatcgtga tgacccagag ccccgatagc ctggccgtgt ctctgggaga gagagccacc     60
atcaactgca agagcagcca gagcctgttc aacgtgagaa gccggaagaa ctacctggcc    120
tggtatcagc agaaacccgg ccagccccc aagctgctga tcagctgggc cagcaccaga    180
gaaagcggcg tgcccgatag attcagcggc agcggaagcg gcaccgactt caccctgaca    240
```

```
atcagctccc tgcaggccga ggacgtggcc gtgtactact gcaagcagag ctacgacctg    300
ttcaccttcg gcagcggcac caagctggaa atcaaa                              336
```

<210> SEQ ID NO 87
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Thr Ser Glu Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 88
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 88

```
gacatccaga tgacccagtc cccctcttct ctgtctgcct ctgtgggcga cagagtgacc    60
atcacctgca aagctcaga gtcactgttt aatgtccgca gcggcaaaaa ctatcttgcg    120
tggtatcagc agaagcctgg caaggctccc aagctgctga tctactgggc cagtgaccga    180
gaatccggcg tgccttccag attctccggc tctggctctg gcaccgattt caccctgacc    240
atctcctccc tccagcctga ggatttcgcc acctactact gcaaacagtc ttacgacctt    300 ttcactttg gcggcggaac aaaggtggag atcaag                               336
```

<210> SEQ ID NO 89
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Thr Ser Gln Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                 85                  90                  95

Ser Tyr Asp Leu Phe Thr Phe Gly Gly Gly Thr Lys Val Glu Ile Lys
            100                 105                 110

<210> SEQ ID NO 90
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 90
gacatccaga tgacccagtc cccctcttct ctgtctgcct ctgtgggcga cagagtgacc      60
atcacctgca aagctcaca gtcactgttt aatgtccgca gcggcaaaaa ctatcttgcg     120
tggtatcagc agaagcctgg caaggctccc aagctgctga tctactgggc agtgaccga    180 gaatccggcg tgccttccag attctccggc tctggctctg gcaccgattt caccctgacc    240
atctcctccc tccagcctga ggatttcgcc acctactact gcaaacagtc ttacgacctt    300 ttcactttg gcggcggaac aaaggtggag atcaag                              336

<210> SEQ ID NO 91
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 91

Thr Ser Ser Glu Ser Leu Phe Asn Val Arg Ser Gly Lys Asn Tyr Leu
 1               5                  10                  15

Ala

<210> SEQ ID NO 92
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 92

Thr Ser Ser Gln Ser Leu Phe Asn Val Arg Ser Gly Lys Asn Tyr Leu
 1               5                  10                  15

Ala

<210> SEQ ID NO 93
<211> LENGTH: 461
<212> TYPE: PRT
<213> ORGANISM: Artificial Sequence
<220> FEATURE:
<223> OTHER INFORMATION: Synthetic peptide sequence

<400> SEQUENCE: 93

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Ser Val Asp Tyr Tyr
                20                  25                  30

Gly Ser Ser Leu Leu Gln Trp Tyr Gln Gln Lys Pro Gly Lys Ala Pro
```

```
                35                  40                  45
Lys Leu Leu Ile Tyr Ala Ala Ser Lys Leu Ala Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Thr Arg
                 85                  90                  95

Lys Ala Tyr Thr Phe Gly Gln Gly Thr Lys Leu Glu Ile Lys Gly Gly
                100                 105                 110

Gly Ser Gly Gly Gly Gly Glu Val Gln Leu Val Glu Ser Gly Gly Gly
            115                 120                 125

Leu Val Gln Pro Gly Gly Ser Leu Arg Leu Ser Cys Ala Ala Ser Gly
            130                 135                 140

Phe Thr Phe Ser Asp Tyr Tyr Met Thr Trp Val Arg Gln Ala Pro Gly
145                 150                 155                 160

Lys Gly Leu Glu Trp Val Ala Phe Ile Arg Asn Gln Ala Arg Gly Tyr
                165                 170                 175

Thr Ser Asp His Asn Pro Ser Val Lys Gly Arg Phe Thr Ile Ser Arg
                180                 185                 190

Asp Asn Ala Lys Asn Ser Leu Tyr Leu Gln Met Asn Ser Leu Arg Ala
                195                 200                 205

Glu Asp Thr Ala Val Tyr Tyr Cys Ala Arg Asp Arg Pro Ser Tyr Tyr
210                 215                 220

Val Leu Asp Tyr Trp Gly Gln Gly Thr Thr Val Thr Val Ser Ser Gly
225                 230                 235                 240

Cys Pro Pro Cys Pro Ala Pro Glu Ala Ala Gly Ala Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Cys Thr Leu Pro Pro
                355                 360                 365

Ser Arg Glu Glu Met Thr Lys Asn Gln Val Ser Leu Trp Cys Leu Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly
450                 455                 460
```

<210> SEQ ID NO 94
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

Gly Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Ser Tyr Trp Met His Trp Val Arg Gln
145                 150                 155                 160

Ala Pro Gly Lys Gly Leu Glu Trp Ile Gly Glu Ile Lys Pro Ser Asn
                165                 170                 175

Glu Leu Thr Asn Val His Glu Lys Phe Lys Asp Arg Phe Thr Ile Ser
            180                 185                 190

Val Asp Lys Ala Lys Asn Ser Ala Tyr Leu Gln Met Asn Ser Leu Arg
        195                 200                 205

Ala Glu Asp Thr Ala Val Tyr Tyr Cys Thr Arg Thr Ile Thr Thr Thr
    210                 215                 220

Glu Gly Tyr Trp Phe Phe Asp Val Trp Gly Gln Gly Thr Leu Val Thr
225                 230                 235                 240

Val Ser Ser Gly Cys Pro Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365
```

```
Thr Leu Pro Pro Cys Arg Glu Glu Met Thr Lys Asn Gln Val Ser Leu
        370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
        450                 455                 460

Gly
465

<210> SEQ ID NO 95
<211> LENGTH: 461
<212> TYPE: PRT
<213> ORGANISM: Artificial Sequence
<220> FEATURE:
<223> OTHER INFORMATION: Synthetic peptide sequence

<400> SEQUENCE: 95

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Tyr Tyr
            20                  25                  30

Gly Ser Ser Leu Leu Gln Trp Tyr Gln Gln Lys Pro Gly Lys Ala Pro
        35                  40                  45

Lys Leu Leu Ile Tyr Ala Ala Ser Lys Leu Ala Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Thr Arg
                85                  90                  95

Lys Ala Tyr Thr Phe Gly Gln Gly Thr Lys Leu Glu Ile Lys Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
        130                 135                 140

Phe Thr Phe Ser Asp Tyr Tyr Met Thr Trp Val Arg Gln Ala Pro Gly
145                 150                 155                 160

Lys Gly Leu Glu Trp Val Ala Phe Ile Arg Asn Gln Ala Arg Gly Tyr
                165                 170                 175

Thr Ser Asp His Asn Pro Ser Val Lys Gly Arg Phe Thr Ile Ser Arg
            180                 185                 190

Asp Asn Ala Lys Asn Ser Leu Tyr Leu Gln Met Asn Ser Leu Arg Ala
        195                 200                 205

Glu Asp Thr Ala Val Tyr Tyr Cys Ala Arg Asp Arg Pro Ser Tyr Tyr
        210                 215                 220

Val Leu Asp Tyr Trp Gly Gln Gly Thr Thr Val Thr Val Ser Ser Gly
225                 230                 235                 240

Cys Pro Pro Cys Pro Ala Pro Glu Ala Ala Gly Ala Pro Ser Val Phe
                245                 250                 255
```

```
Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Cys Thr Leu Pro Pro
        355                 360                 365

Ser Arg Glu Glu Met Thr Lys Asn Gln Val Ser Leu Trp Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly
            450                 455                 460

<210> SEQ ID NO 96
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Thr Ser Asp Gln Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

Gly Gly Gly Gly Ser Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Ser Tyr Trp Met His Trp Val Arg Gln
145                 150                 155                 160
```

Ala Pro Gly Lys Gly Leu Glu Trp Ile Gly Glu Ile Lys Pro Ser Asn
                165                 170                 175

Glu Leu Thr Asn Val His Glu Lys Phe Lys Asp Arg Phe Thr Ile Ser
            180                 185                 190

Val Asp Lys Ala Lys Asn Ser Ala Tyr Leu Gln Met Asn Ser Leu Arg
        195                 200                 205

Ala Glu Asp Thr Ala Val Tyr Tyr Cys Thr Arg Thr Ile Thr Thr Thr
    210                 215                 220

Glu Gly Tyr Trp Phe Phe Asp Val Trp Gly Gln Gly Thr Leu Val Thr
225                 230                 235                 240

Val Ser Ser Gly Cys Pro Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Cys Arg Glu Glu Met Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly
465

<210> SEQ ID NO 97
<211> LENGTH: 461
<212> TYPE: PRT
<213> ORGANISM: Artificial Sequence
<220> FEATURE:
<223> OTHER INFORMATION: Synthetic peptide sequence

<400> SEQUENCE: 97

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Tyr Tyr
            20                  25                  30

Gly Ser Ser Leu Leu Gln Trp Tyr Gln Gln Lys Pro Gly Lys Ala Pro
        35                  40                  45

```
Lys Leu Leu Ile Tyr Ala Ala Ser Lys Leu Ala Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Thr Arg
                 85                  90                  95

Lys Ala Tyr Thr Phe Gly Gln Gly Thr Lys Leu Glu Ile Lys Gly Gly
                100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
        130                 135                 140

Phe Thr Phe Ser Asp Tyr Tyr Met Thr Trp Val Arg Gln Ala Pro Gly
145                 150                 155                 160

Lys Gly Leu Glu Trp Val Ala Phe Ile Arg Asn Gln Ala Arg Gly Tyr
                165                 170                 175

Thr Ser Asp His Asn Pro Ser Val Lys Gly Arg Phe Thr Ile Ser Arg
                180                 185                 190

Asp Asn Ala Lys Asn Ser Leu Tyr Leu Gln Met Asn Ser Leu Arg Ala
                195                 200                 205

Glu Asp Thr Ala Val Tyr Tyr Cys Ala Arg Asp Arg Pro Ser Tyr Tyr
        210                 215                 220

Val Leu Asp Tyr Trp Gly Gln Gly Thr Thr Val Thr Val Ser Ser Gly
225                 230                 235                 240

Cys Pro Pro Cys Pro Ala Pro Glu Ala Ala Gly Ala Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Cys Thr Leu Pro Pro
        355                 360                 365

Ser Arg Glu Glu Met Thr Lys Asn Gln Val Ser Leu Trp Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly
450                 455                 460
```

<210> SEQ ID NO 98
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

Gly Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Ser Tyr Trp Met His Trp Val Arg Gln
145                 150                 155                 160

Ala Pro Gly Lys Gly Leu Glu Trp Ile Gly Glu Ile Lys Pro Ser Asn
                165                 170                 175

Glu Leu Thr Asn Val His Glu Lys Phe Lys Asp Arg Phe Thr Ile Ser
            180                 185                 190

Val Asp Lys Ala Lys Asn Ser Ala Tyr Leu Gln Met Asn Ser Leu Arg
        195                 200                 205

Ala Glu Asp Thr Ala Val Tyr Tyr Cys Thr Arg Thr Ile Thr Thr Thr
    210                 215                 220

Glu Gly Tyr Trp Phe Phe Asp Val Trp Gly Gln Gly Thr Leu Val Thr
225                 230                 235                 240

Val Ser Ser Gly Cys Pro Pro Cys Pro Ala Pro Glu Ala Ala Gly Ala
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365
```

```
Thr Leu Pro Pro Cys Arg Glu Glu Met Thr Lys Asn Gln Val Ser Leu
        370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
450                 455                 460

Gly
465

<210> SEQ ID NO 99
<211> LENGTH: 461
<212> TYPE: PRT
<213> ORGANISM: Artificial Sequence
<220> FEATURE:
<223> OTHER INFORMATION: Synthetic peptide sequence

<400> SEQUENCE: 99

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Tyr Tyr
            20                  25                  30

Gly Ser Ser Leu Leu Gln Trp Tyr Gln Gln Lys Pro Gly Lys Ala Pro
        35                  40                  45

Lys Leu Leu Ile Tyr Ala Ala Ser Lys Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Thr Arg
                85                  90                  95

Lys Ala Tyr Thr Phe Gly Gln Gly Thr Lys Leu Glu Ile Lys Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Asp Tyr Tyr Met Thr Trp Val Arg Gln Ala Pro Gly
145                 150                 155                 160

Lys Gly Leu Glu Trp Val Ala Phe Ile Arg Asn Gln Ala Arg Gly Tyr
                165                 170                 175

Thr Ser Asp His Asn Pro Ser Val Lys Gly Arg Phe Thr Ile Ser Arg
            180                 185                 190

Asp Asn Ala Lys Asn Ser Leu Tyr Leu Gln Met Asn Ser Leu Arg Ala
        195                 200                 205

Glu Asp Thr Ala Val Tyr Tyr Cys Ala Arg Asp Arg Pro Ser Tyr Tyr
    210                 215                 220

Val Leu Asp Tyr Trp Gly Gln Gly Thr Thr Val Thr Val Ser Ser Gly
225                 230                 235                 240

Cys Pro Pro Cys Pro Ala Pro Glu Ala Ala Gly Ala Pro Ser Val Phe
                245                 250                 255
```

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Cys Thr Leu Pro Pro
        355                 360                 365

Ser Arg Glu Glu Met Thr Lys Asn Gln Val Ser Leu Trp Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly
450                 455                 460

<210> SEQ ID NO 100
<211> LENGTH: 465
<212> TYPE: PRT
<213> ORGANISM: Artificial Sequence
<220> FEATURE:
<223> OTHER INFORMATION: Synthetic peptide sequence

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Thr Ser Ser Glu Ser Leu Phe Asn Val
            20                  25                  30

Arg Ser Gly Lys Asn Tyr Leu Ala Trp Tyr Gln Gln Lys Pro Gly Lys
        35                  40                  45

Ala Pro Lys Leu Leu Ile Tyr Trp Ala Ser Asp Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

Gly Gly Gly Gly Ser Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Ser Tyr Trp Met His Trp Val Arg Gln
145                 150                 155                 160

-continued

```
Ala Pro Gly Lys Gly Leu Glu Trp Ile Gly Glu Ile Lys Pro Ser Asn
            165                 170                 175
Glu Leu Thr Asn Val His Glu Lys Phe Lys Asp Arg Phe Thr Ile Ser
            180                 185                 190
Val Asp Lys Ala Lys Asn Ser Ala Tyr Leu Gln Met Asn Ser Leu Arg
            195                 200                 205
Ala Glu Asp Thr Ala Val Tyr Tyr Cys Thr Arg Thr Ile Thr Thr Thr
            210                 215                 220
Glu Gly Tyr Trp Phe Phe Asp Val Trp Gly Gln Gly Thr Leu Val Thr
225                 230                 235                 240
Val Ser Ser Gly Cys Pro Pro Cys Pro Ala Pro Glu Ala Ala Gly Ala
            245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
            275                 280                 285
Asp Pro Glu Val Lys Phe Asn Trp Tyr Val Asp Gly Val Glu Val His
            290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
            325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
            355                 360                 365
Thr Leu Pro Pro Cys Arg Glu Glu Met Thr Lys Asn Gln Val Ser Leu
            370                 375                 380
Ser Cys Ala Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
            405                 410                 415
Leu Asp Ser Asp Gly Ser Phe Phe Leu Val Ser Lys Leu Thr Val Asp
            420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
            450                 455                 460
Gly
465
```

ANTIBODIES SPECIFIC FOR CD3 AND USES THEREOF

RELATED APPLICATIONS

This application claims the benefit of U.S. Provisional Application No. 62/675,562, filed May 23, 2018, and U.S. Provisional Application No. 62/847,460, filed May 14, 2019, which are incorporated by reference herein in their entirety.

SEQUENCE LISTING

This application is being filed electronically via EFS-Web and includes an electronically submitted sequence listing in .txt format. The .txt file contains a sequence listing entitled "PC72375-PRV2_SequenceListing_ST25_05132019. txt" created on May 13, 2019, and having a size of 100 KB. The sequence listing contained in this .txt file is part of the specification and is incorporated herein by reference in its entirety.

FIELD OF THE INVENTION

The present invention relates to antibodies and antigen-binding fragments thereof, which are specific for CD3, and methods of use thereof. The present invention also relates to multispecific antibodies that bind CD3 and a target antigen, and methods of use thereof.

BACKGROUND OF THE INVENTION

Cluster of Differentiation 3 (CD3) is a homodimeric or heterodimeric antigen expressed on T cells in association with the T cell receptor complex (TCR) and is required for T cell activation. T cell activation is a complex phenomenon that depends on the participation of a variety of cell surface molecules expressed on the responding T cell population. Functional CD3 is formed from the dimeric association of two of four different chains: epsilon, zeta, delta and gamma. For example, the antigen-specific T cell receptor (TCR) is composed of a disulfide-linked heterodimer, containing two clonally distributed, integral membrane glycoprotein chains, alpha and beta (a and 13), or gamma and delta (γ and δ), non-covalently associated with a complex of low molecular weight invariant proteins, commonly designated as CD3. The CD3 dimeric arrangements also include gamma/epsilon, delta/epsilon and zeta/zeta.

Antibodies against CD3 have been shown to cluster CD3 on T cells, thereby causing T cell activation in a manner similar to the engagement of the TCR by peptide-loaded MHC molecules. Thus, CD3 antibodies may be useful for therapeutic purposes involving the T cell activation.

SUMMARY OF THE INVENTION

The present invention provides antibodies that bind CD3, as well as compositions, such as pharmaceutical compositions, comprising one or more CD3 antibodies. The antibodies according to this aspect of the invention are useful, inter alia, for targeting T cells expressing CD3, and for stimulating T cell activation, e.g., under circumstances where T cell-mediated killing is beneficial or desirable. The CD3 antibodies of the invention may be included as part of a multispecific antibody, e.g., bispecific antibody, that directs CD3-mediated T cell activation to specific cell types such as tumor cells or infectious agents.

In one aspect, the present invention provides an antibody which specifically binds to CD3, wherein the antibody comprises: (a) a heavy chain variable (VH) region comprising a VH complementarity determining region one (VH CDR1), a VH complementarity determining region two (VH CDR2), and a VH complementarity determining region three (VH CDR3) of the VH sequence shown in SEQ ID NO: 2, 4, 5, 7, 10, 12 or 35; and/or (b) a light chain variable (VL) region comprising a VL complementarity determining region one (VL CDR1), a VL complementarity determining region two (VL CDR2), and a VL complementarity determining region three (VL CDR3) of the VL sequence shown in SEQ ID NO: 1, 3, 6, 8, 9, 11, 34, 87 or 89.

In one embodiment of this aspect, the CD3 antibody comprises: (a) a VH region comprising (i) a VH CDR1 comprising a sequence of SEQ ID NO: 13, 14, or 15; (ii) a VH CDR2 comprising a sequence of SEQ ID NO: 16, 17, 19, 20, 21, 22, 23 or 24; and (iii) a VH CDR3 comprising a sequence of SEQ ID NO: 18 or 25; and/or (b) a VL region comprising (i) a VL CDR1 comprising a sequence of SEQ ID NO: 26, 29, 30, 32, 91 or 92; (ii) a VL CDR2 comprising a sequence of SEQ ID NO: 27 or 31; and (iii) a VL CDR3 comprising a sequence of SEQ ID NO: 28 or 33.

In some such embodiments, the invention provides an antibody, wherein: (a) the VH region comprises a sequence of SEQ ID NO: 2, 4, 5, 7, 10, 12 or 35; and/or (b) the VL region comprises a sequence of SEQ ID NO: SEQ ID NO: 1, 3, 6, 8, 9, 11, 34, 87 or 89.

In other embodiments, the antibody comprises a VL/VH amino acid sequence pair selected from the group consisting of SEQ ID NOs: 1 and 2; SEQ ID NOs: 3 and 2; SEQ ID NOs: 3 and 4; SEQ ID NOs: 3 and 5; SEQ ID NOs: 6 and 7; SEQ ID NOs: 8 and 7; SEQ ID NOs: 6 and 4; SEQ ID NOs: 8 and 4; SEQ ID NOs: 9 and 10; SEQ ID NOs: 9 and 7; SEQ ID NOs: 11 and 12; SEQ ID NOs: 34 and 35; SEQ ID NOs: 9 and 4; SEQ ID NOs: 87 and 4; and SEQ ID NOs: 89 and 4.

In some embodiments of each of the foregoing, the antibody is selected from the group consisting of a Fab, a Fab fragment, a F(ab)$_2$ fragment, an Fv fragment, a single chain Fv fragment, a disulfide stabilized Fv fragment, a single-chain antibody, a monoclonal antibody, a chimeric antibody, a bispecific antibody, a trispecific antibody, a multispecific antibody, a bispecific heterodimeric diabody, a bispecific heterodimeric IgG, a polyclonal antibody, a labeled antibody, a humanized antibody, a human antibody, and fragments thereof.

In a specific embodiment, the antibody is a bispecific antibody. In some such embodiments, the bispecific antibody specifically binds to a tumor antigen.

In some embodiments, the antibody of the present invention further comprises a human or humanized VH framework and a human or humanized VL framework. In some such embodiments, the antibody is a humanized antibody.

The present invention further provides a pharmaceutical composition comprising a CD3 antibody of the invention, as further disclosed herein, and a pharmaceutically acceptable carrier.

In another aspect, the present invention provides a method of modulating a T cell mediated immune response in a subject in need thereof, comprising administering to the subject an effective amount of the antibody or the pharmaceutical composition as disclosed herein, such that the immune response in the subject is modulated.

In one aspect, the present invention provides a method of inhibiting growth of tumor cells in a subject, comprising administering to a subject a bispecific antibody, trispecific antibody, multispecific antibody, bispecific heterodimeric diabody, or bispecific heterodimeric IgG as disclosed herein in an amount effective to inhibit growth of the tumor cells.

In some such embodiments, the tumor cells are of a cancer. In specific embodiments, the cancer is selected from the group consisting of breast, ovarian, thyroid, prostate, cervical, lung, bladder, endometrial, head and neck, testicular, glioblastoma cancer and cancer of digestive system.

In one embodiment, the cancer of digestive system is selected from the group consisting of esophagus, stomach, small intestine, colon, rectum, anus, liver, gall bladder, appendix, bile ducts, and pancreas.

In one embodiment, the invention provides an antibody, or a pharmaceutical composition comprising such an antibody, for use in therapy.

In another embodiment, the invention provides the use of an antibody of the invention in the manufacture of a medicament for use in therapy. In some such embodiments, the therapy comprises activation of a cytolytic T cell response.

In one aspect, the present invention provides a polynucleotide comprising a nucleotide sequence encoding an antibody as disclosed herein. In another aspect, the invention provides a vector comprising such a polynucleotide.

In yet another aspect, the invention provides a host cell comprising the vectors as disclosed herein. In some such embodiments, the host cell recombinantly produces the antibody as disclosed herein. In specific embodiments, the host cell is selected from the group consisting of bacterial cell lines, mammalian cell lines, insect cell lines, yeast cell lines. In a particular embodiment, the mammalian cell line is a CHO cell line.

In one aspect, the present invention provides a method of producing an antibody as disclosed herein, comprising culturing a host cell under conditions that result in production of the antibody as disclosed herein, and purifying the antibody from the culture supernatant.

In another aspect, the present invention provides a use of a CD3 antibody, a polynucleotide, a vector, or a host cell as disclosed herein, in the manufacture of a medicament for treating a disorder.

In one aspect, the invention provides an antibody, or a pharmaceutical composition for use in a method of modulating a T cell mediated immune response in a subject in need thereof. In specific embodiments, the invention provides an antibody, or a pharmaceutical composition for use in a method of inhibiting growth of tumor cells in a subject.

In another aspect, the invention provides an antibody, or a pharmaceutical composition for use in treating cancer, optionally wherein the cancer is selected from the group consisting of breast, ovarian, thyroid, prostate, cervical, lung, bladder, endometrial, head and neck, testicular, glioblastoma cancer and cancer of digestive system.

In yet another aspect, the invention provides an antibody, or a pharmaceutical composition for use in treating cancer wherein the T cell mediated immune response is modulated or wherein the growth of tumor cells is inhibited.

Other embodiments will become apparent from a review of the detailed description. Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF FIGURES/DRAWINGS

FIG. 1 provides a schematic of the architecture of a bispecific antibody having a first heterodimer-promoting domain and a second heterodimer-promoting domain comprising an Fc chain optimized to associate via a "knob-in-hole" association.

Figure 5:
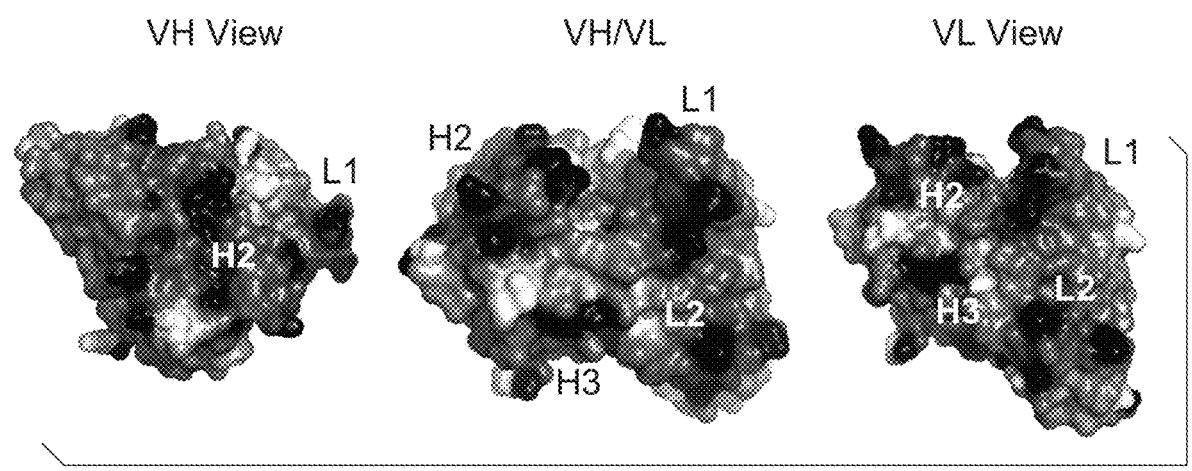

FIG. 5 depicts potential energy surface (PES) of the H2B4 Fv region from the x-ray crystal structure. This includes 3 views highlighting the VH region, the VH/VL interface and the VL region. The CDRs with excess positive charge are indicated in the figure for reference. Dark black represents positive charge and white represents negative charge.

Figure 6:
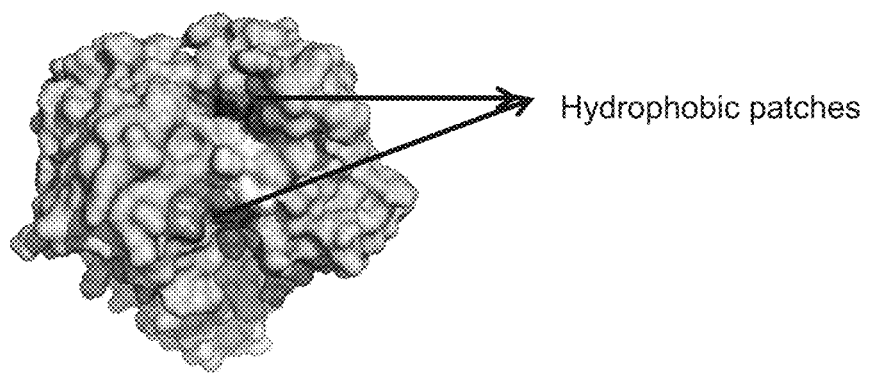

FIG. 6 depicts spatial aggregation propensity (SAP) surface of the Fv region of H2B4. The regions with concentrated hydrophobic residues are labeled.

Figure 7:
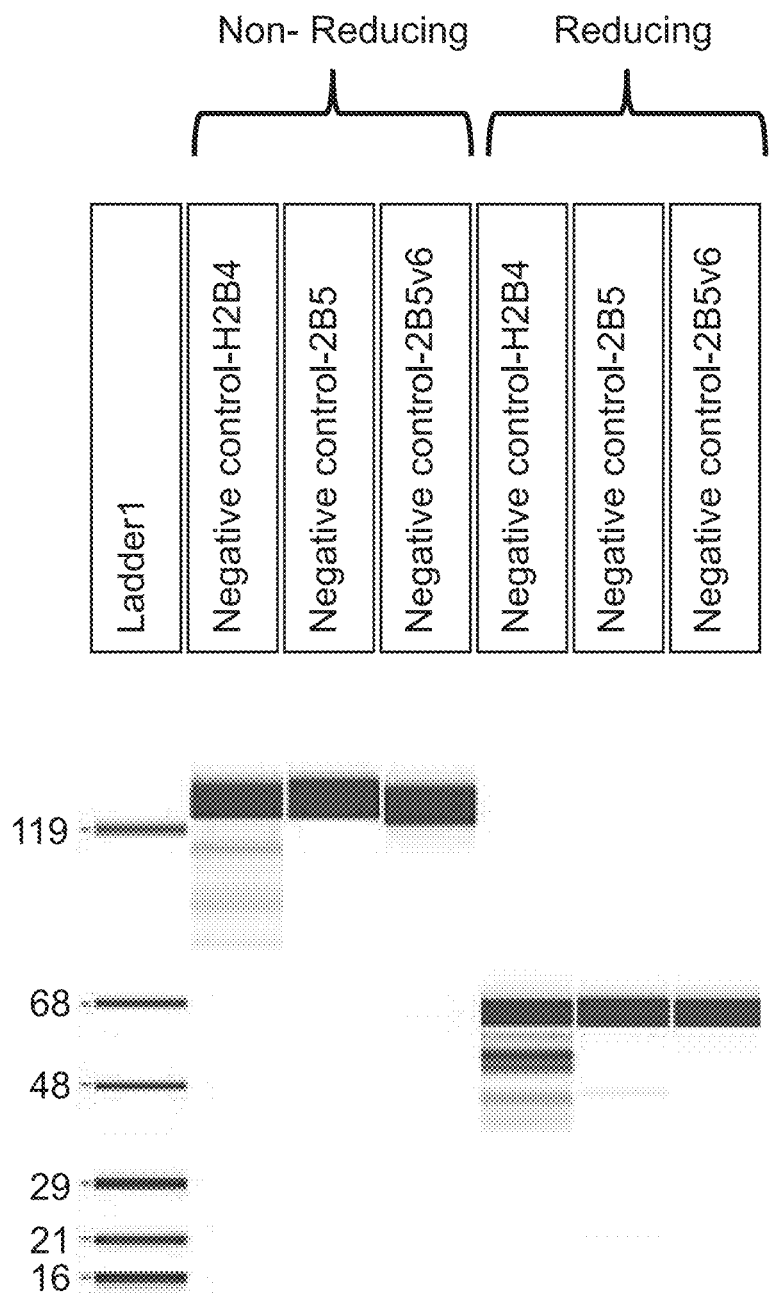

FIG. 7 depicts heterogeneity in the bispecific antibodies containing CD3 antibody binding domains H2B4, 2B5 and 2B5v6, using capillary gel-electropherogram.

Figure 8:
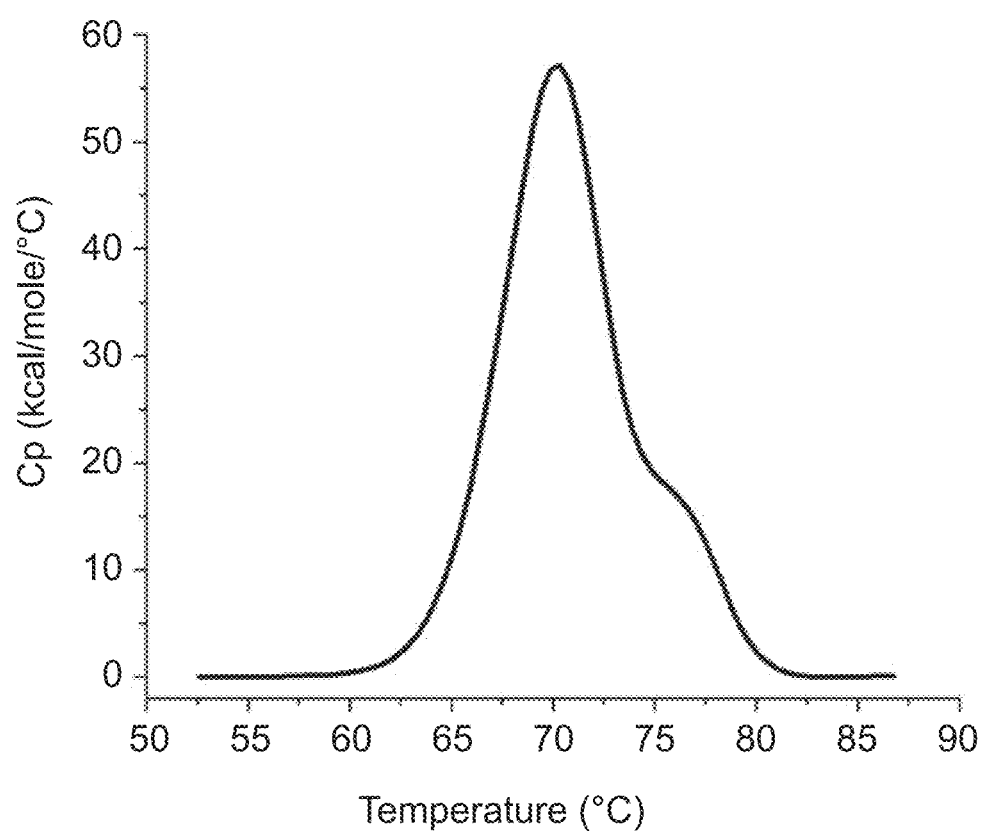

FIG. 8 depicts heat capacity of GUCY2c-1608 (GUCY2c-2B5v6) bispecific antibody as a function of temperature, using differential scanning calorimetry (DSC) thermogram.

Figure 9:
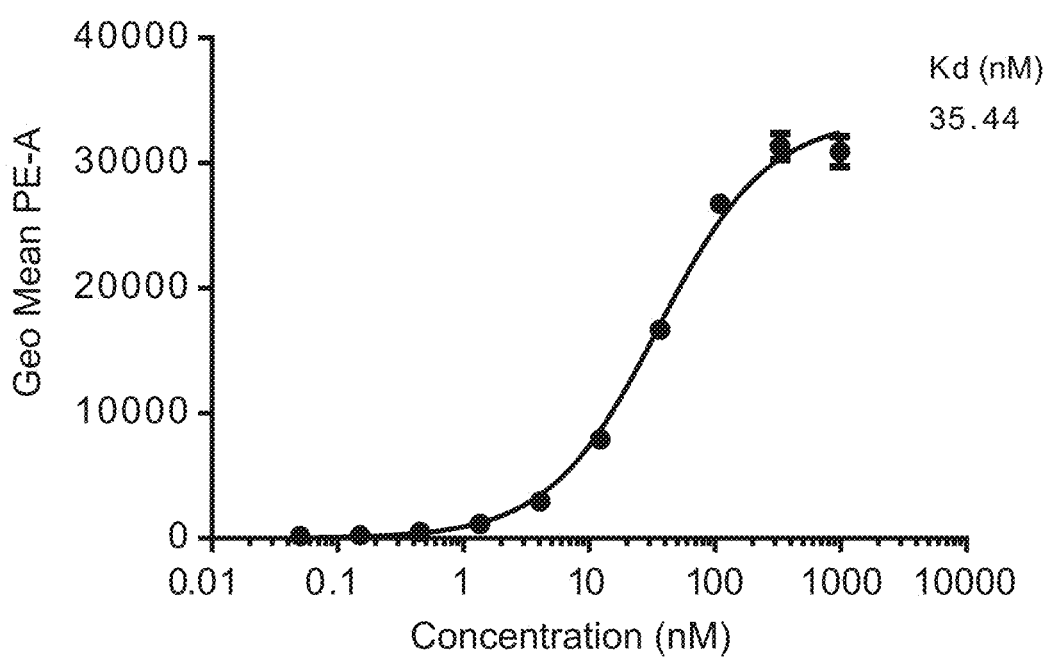

FIG. 9 depicts GUCY2c-1608 (GUCY2c-2B5v6) bispecific antibody binding to naïve T cells.

Figure 10:
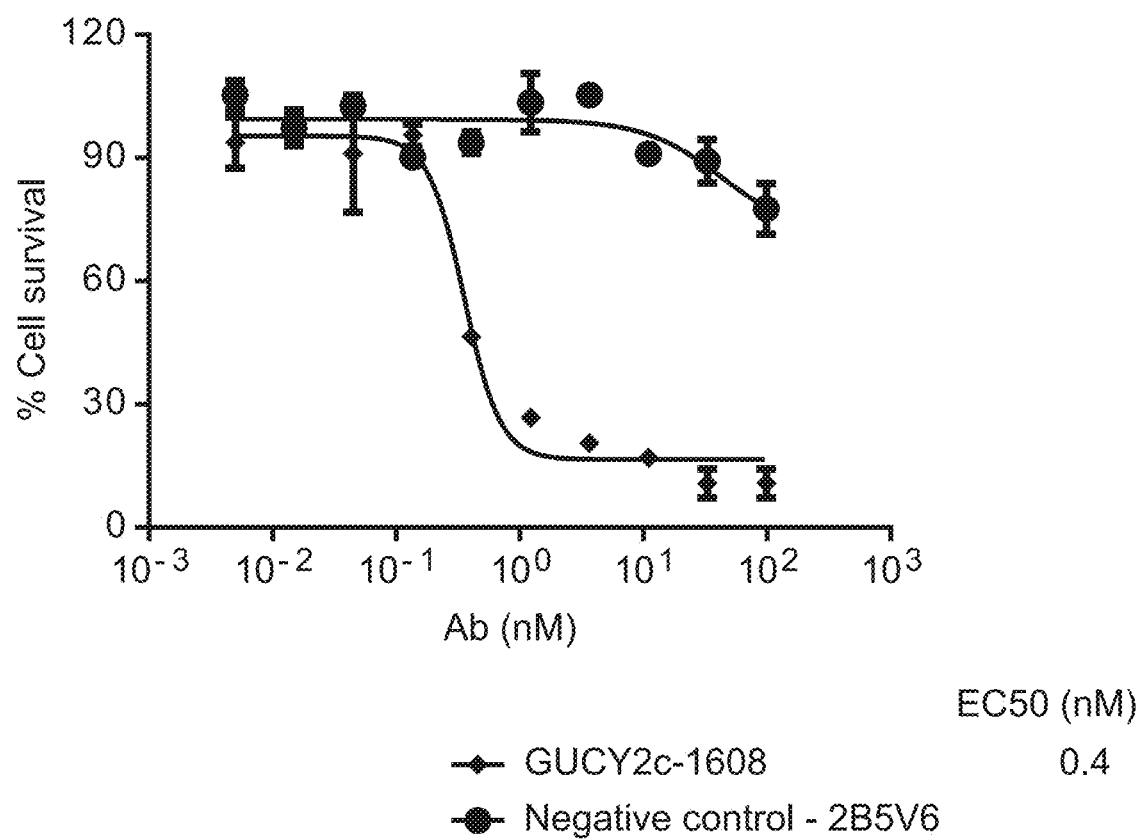

FIG. 10 depicts cell viability data for in vitro cytotoxicity mediated by GUCY2c-1608 (GUCY2c-2B5v6) bispecific antibody.

Figure 11A:
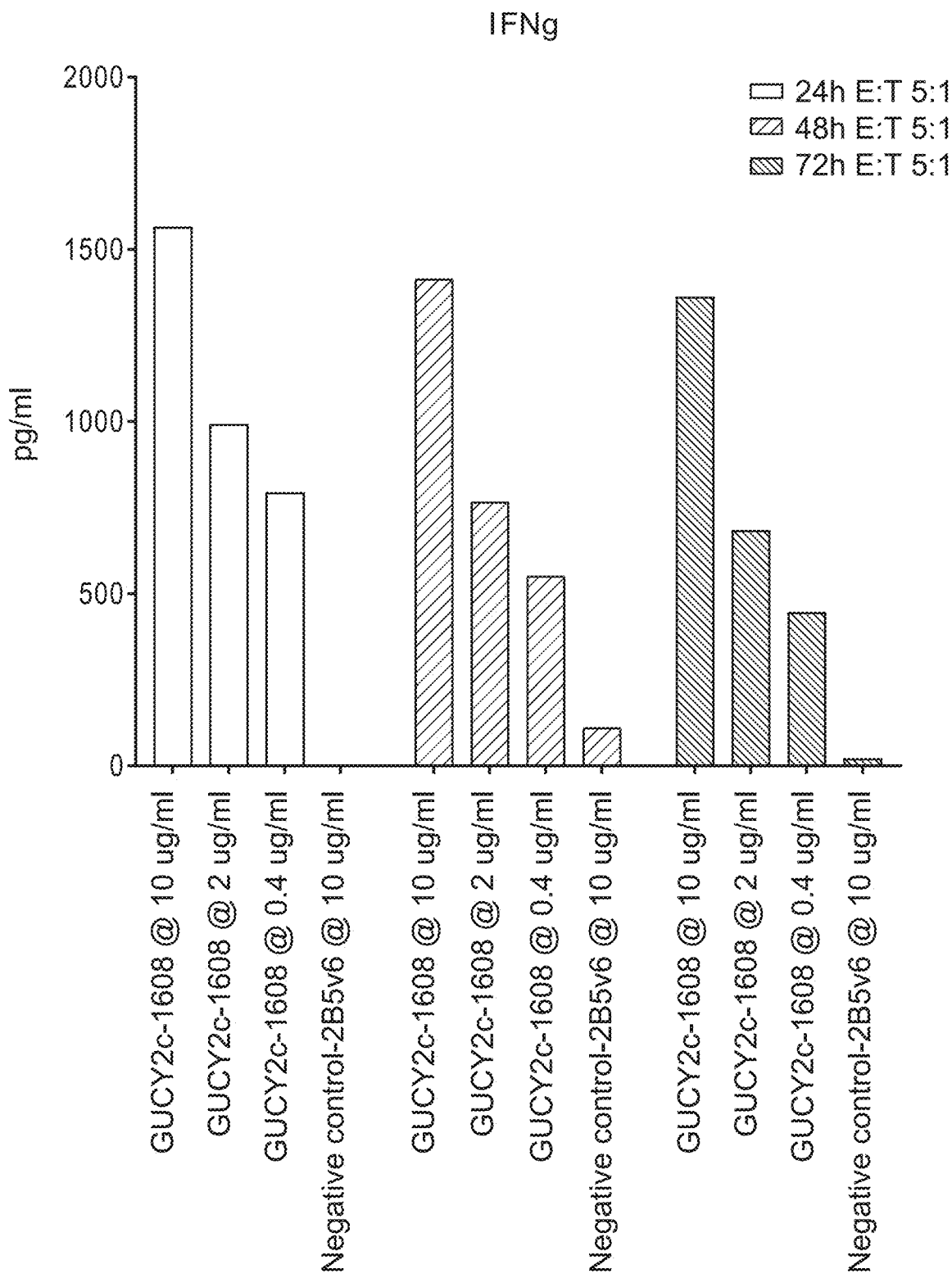
Figure 11B:
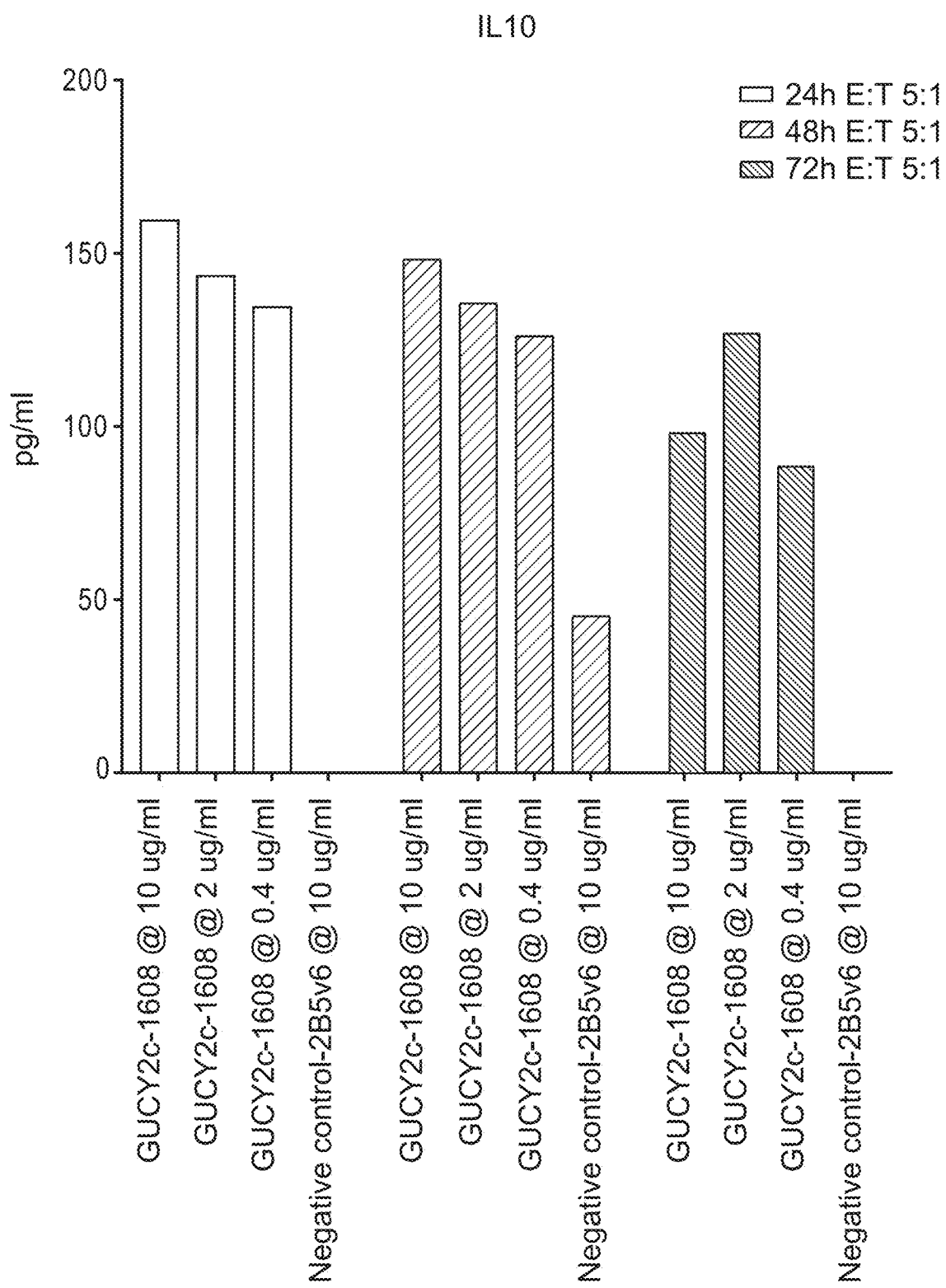
Figure 11C:
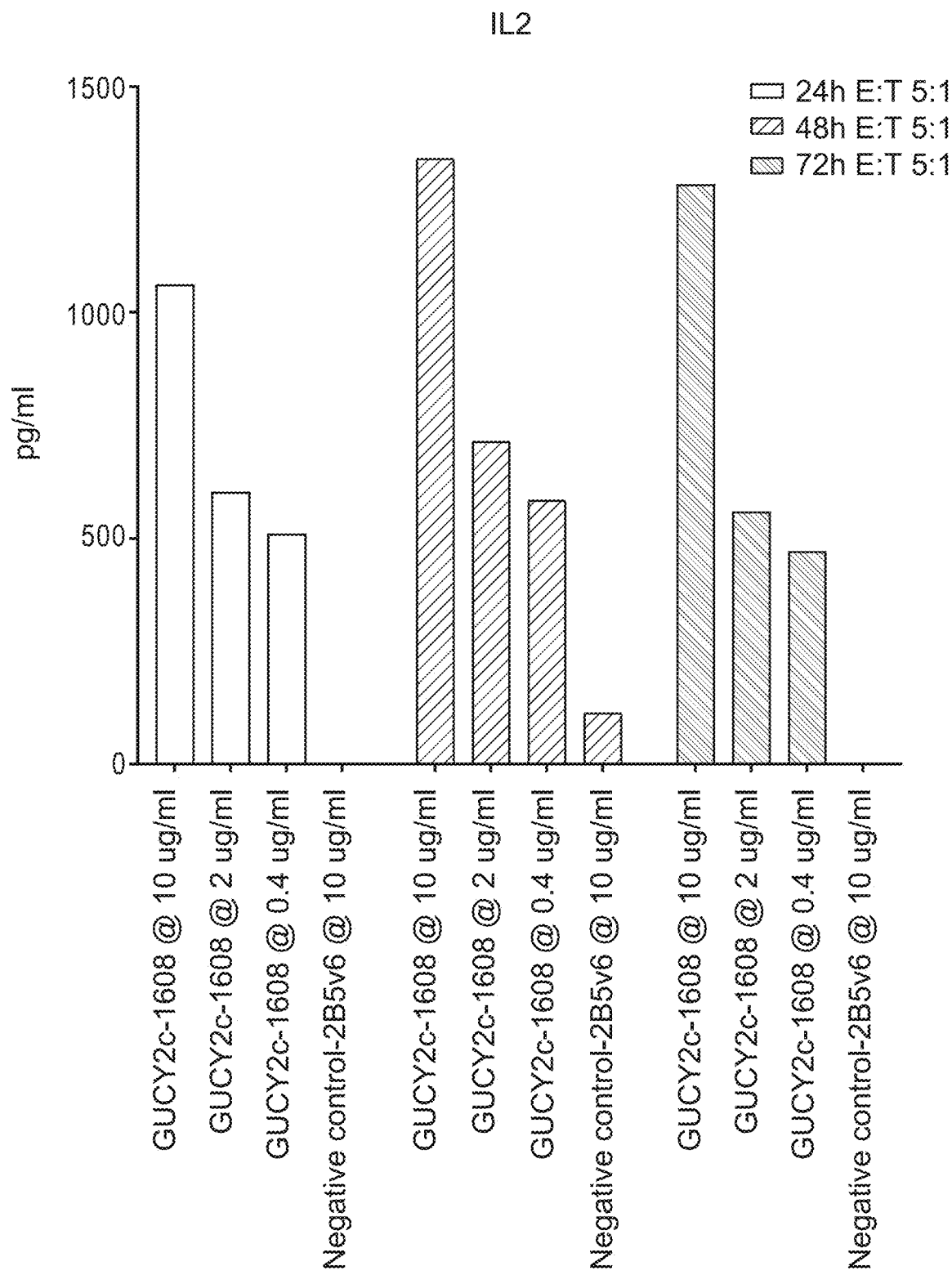
Figure 11D:
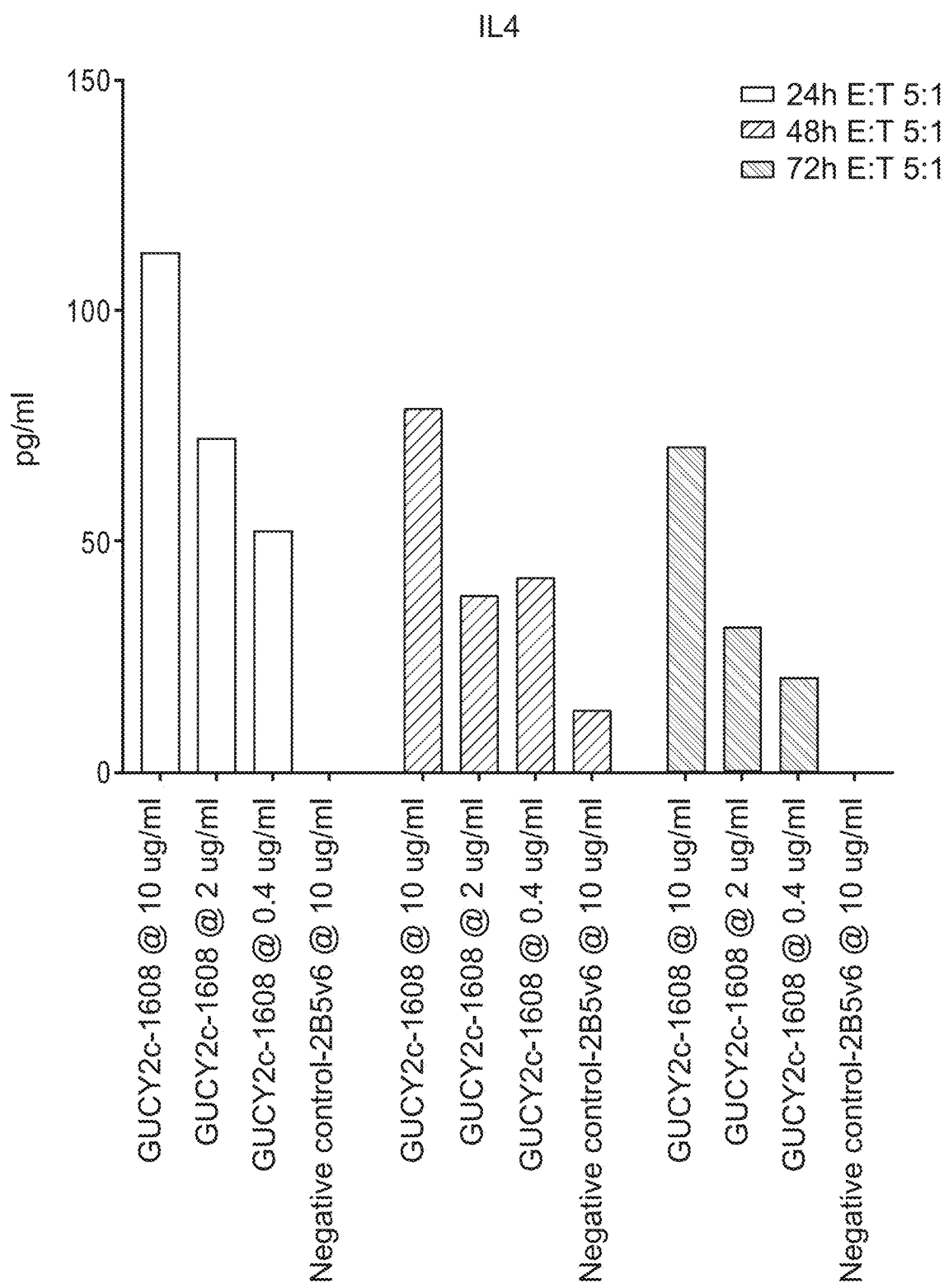
Figure 11E:
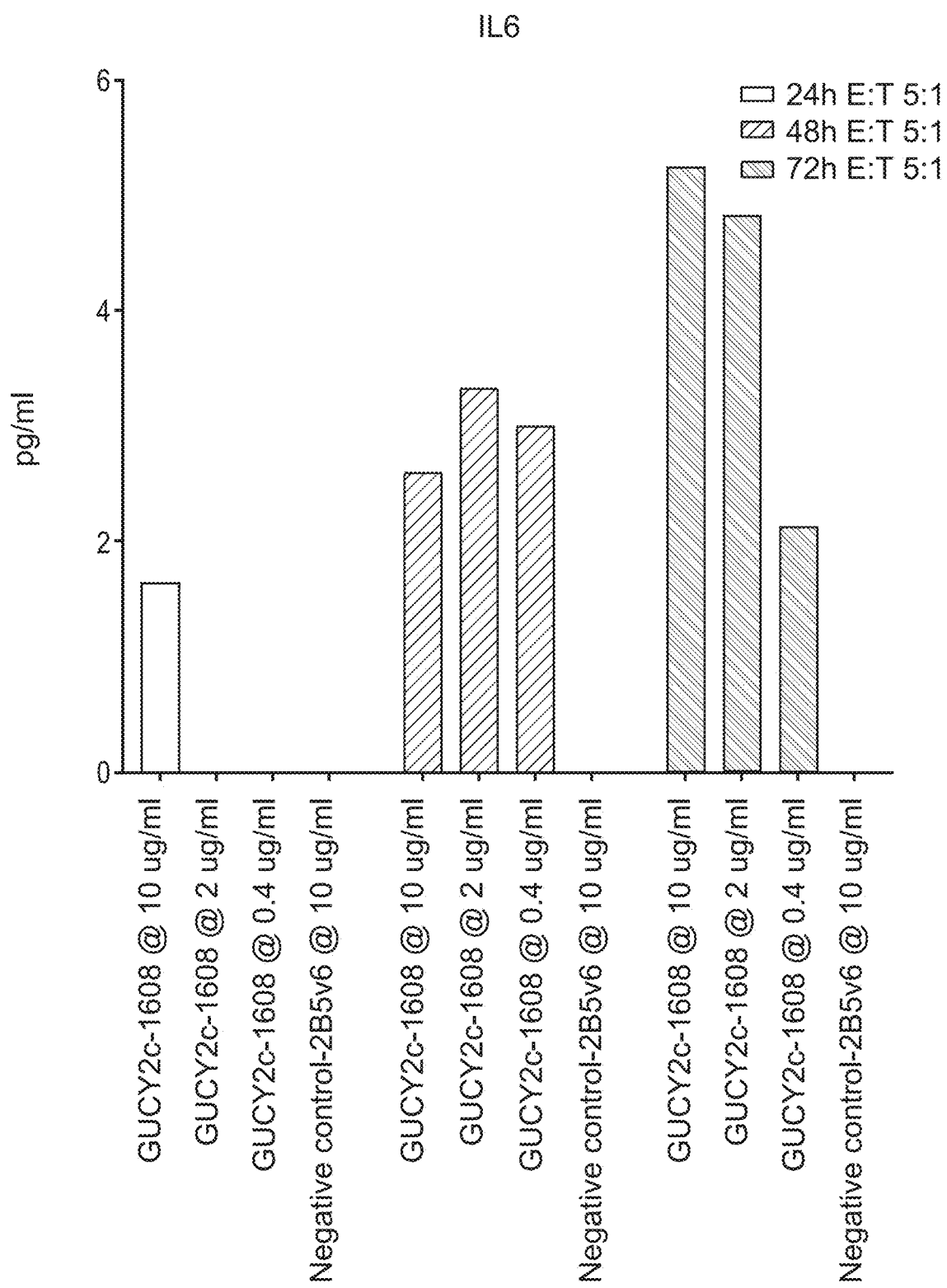
Figure 11F:
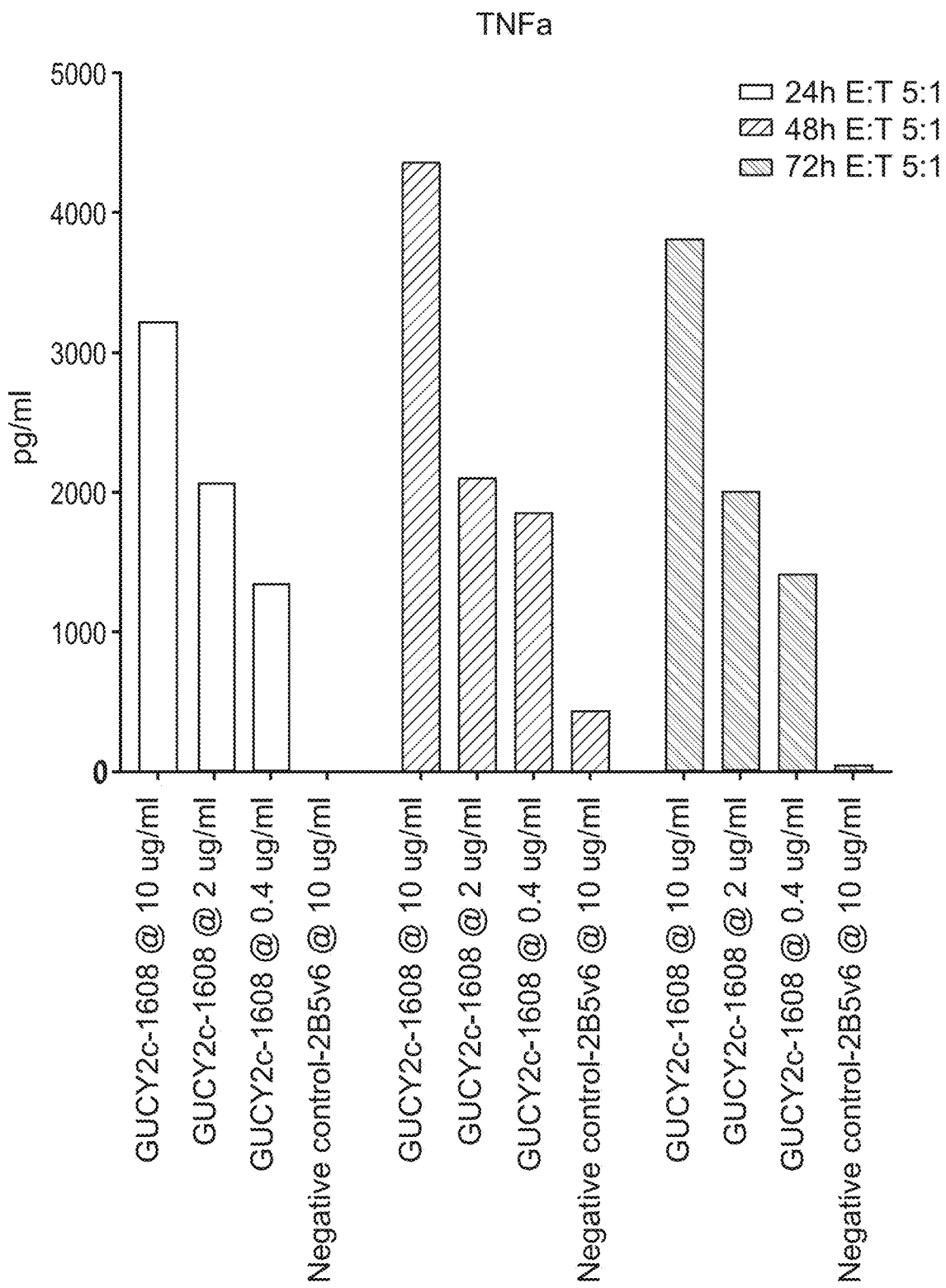

FIGS. 11A to 11F depict in vitro cytokine release measurements with GUCY2c-1608 (GUCY2c-2B5v6) bispecific. The bispecific antibody recruits naïve human T cells to GUCY2c-expressing T84 cells to induce cytokine release in vitro. Luminex based assay showed upregulation of human IFN-gamma (FIG. 11A), IL10 (FIG. 11B), IL2 (FIG. 11C), IL4 (FIG. 11D), IL6 (FIG. 11E) and TNF-alpha (FIG. 11F).

Figure 12:
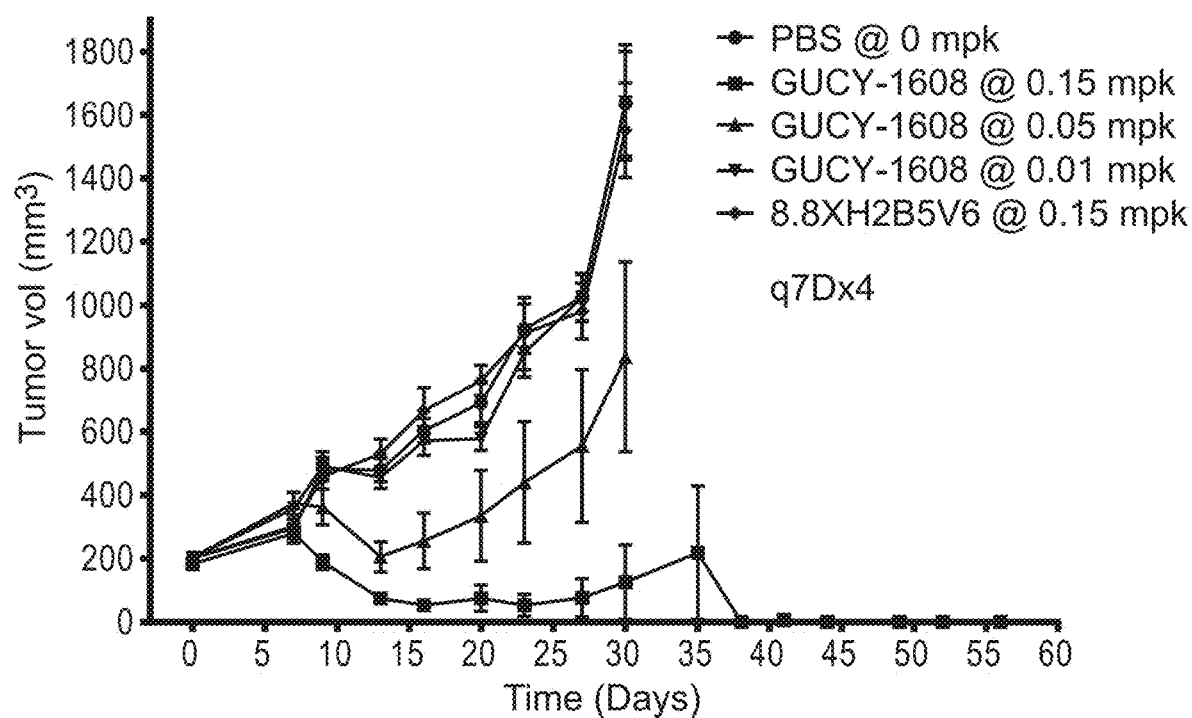

FIG. 12 depicts dose dependent tumor growth inhibition by GUCY2c-1608 (GUCY2c-2B5v6) bispecific antibody in a colorectal cancer patient derived xenograft, PDX-CRX-11201 in an adoptive transfer system.

FIG. 13 depicts dose dependent tumor growth inhibition by GUCY2C-1608 (GUCY2C-2B5v6) bispecific antibody in a colorectal cancer cell line xenograft, LS1034 in an adoptive transfer system.

Figure 14A:
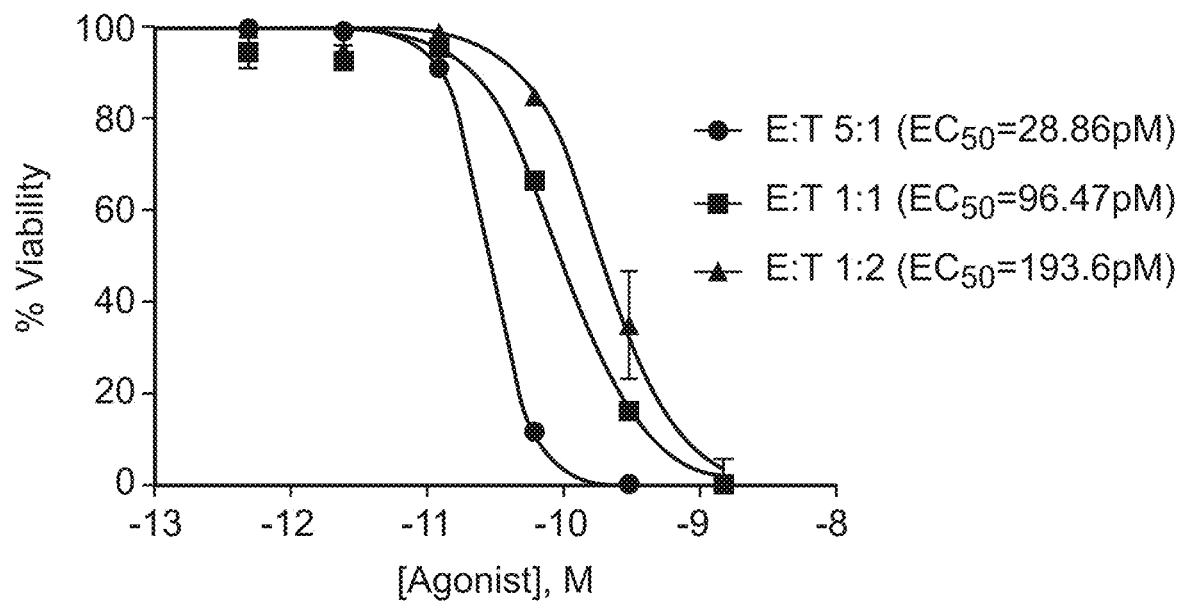
Figure 14B:
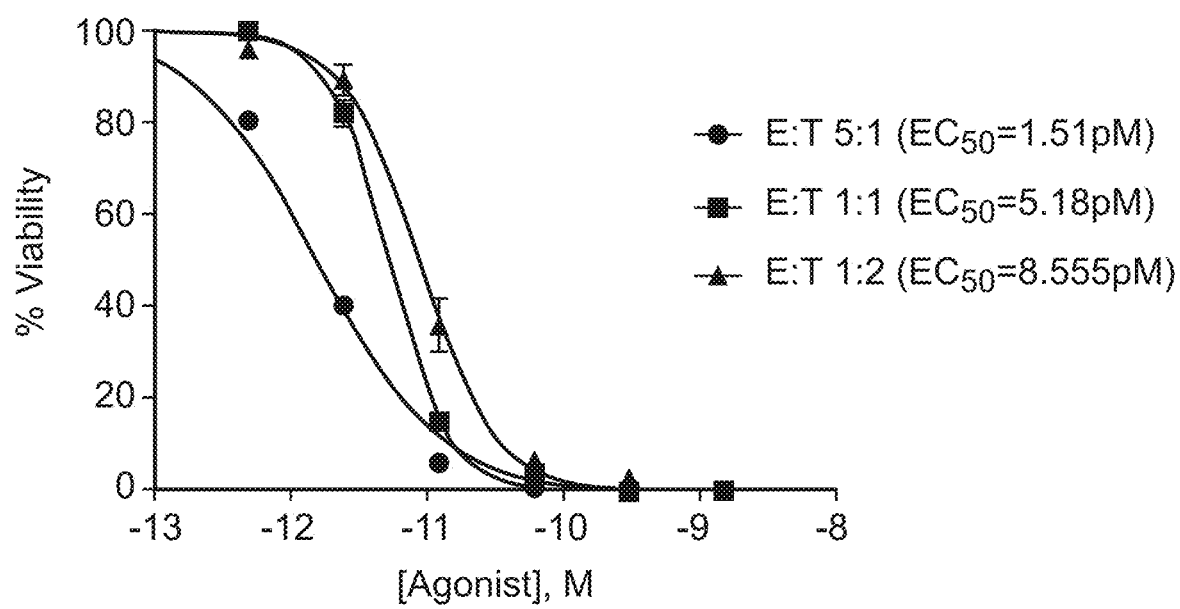

FIG. 14A depicts the results of cell viability data showing the in vitro cytotoxicity mediated by FLT3-2B5v6 bispecific antibodies at different effector to target (E:T) ratios using Flt3 expressing MV4-11 cells. FIG. 14B depicts the results of cell viability data showing the in vitro cytotoxicity mediated by FLT3-2B5v6 bispecific antibodies at different effector to target (E:T) ratios using Flt-3 expressing EOL-1 cells.

Figure 15:
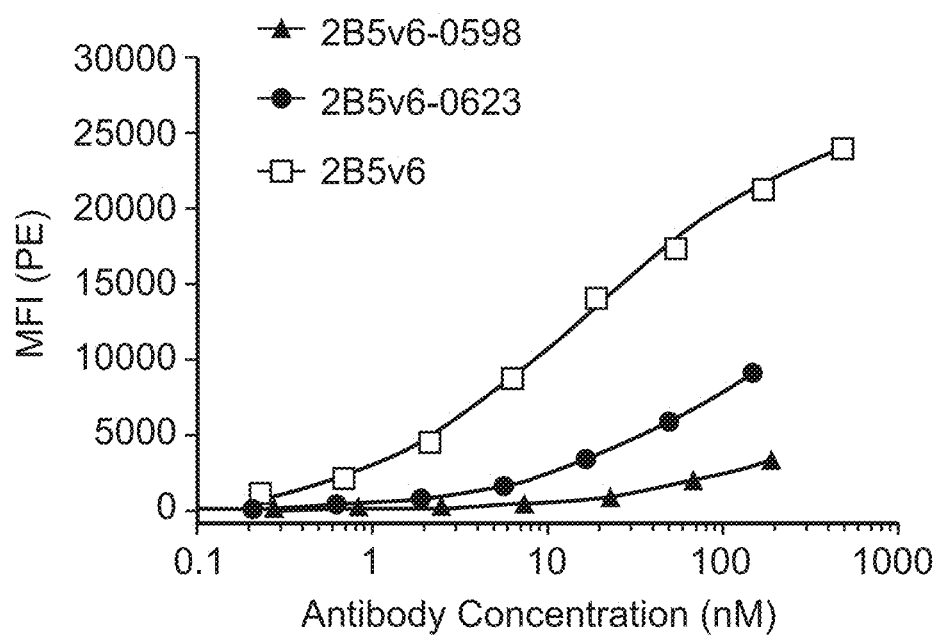

FIG. 15 depicts the binding of low-affinity 2B5v6 variants to Jurkat cells expressing CD3.

FIG. 16 depicts a graph summarizing results of a study showing anti-GUCY2C bispecific T cell mediated cytotoxicity with anti-CD3 variants.

DETAILED DESCRIPTION

The invention disclosed herein provides antibodies that specifically bind to CD3 (e.g., human CD3), including full length antibodies or antigen-binding fragments thereof. The invention also provides polynucleotides encoding these antibodies, compositions comprising these antibodies, and methods of making and using these antibodies. The invention further provides methods for treating a disorder, using the antibodies, as described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). In some cases, terms with commonly understood meanings are defined herein for clarity and/or for ready reference, and the inclusion of such definitions herein should not necessarily be construed to represent a substantial difference over what is generally understood in the art.

The invention will now be described in detail by way of reference using the following definitions and examples. All patents and publications, including all sequences disclosed within such patents and publications, referred to herein are expressly incorporated by reference.

Definitions

In general, unless otherwise defined, all terms of art, notations and other scientific terms or terminology used herein are intended to have the meanings commonly understood by those of skill in the art to which this invention pertains. For example, the term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the singular forms "a", "an" and "the" include their corresponding plural references unless the context clearly dictates otherwise.

As used herein, the numeric ranges are inclusive of the numbers defining the range.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. For instance, in some embodiments, about or approximately a particular value may indicate a value of 99%, 95%, or 90% of that value. As an example, the expression of "about 100" includes 99 and 101 and all values in between (e.g., 99.1, 99.2, 99.3, 99.4, 99.5, etc.). As another example, where the temperature is 70° C., "about" or "approximately" 70° C. may equal 69° C., 66° C., or 63° C. It is to be understood that these are merely examples.

As used herein, nucleic acids are written left to right in 5' to 3' direction; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains. Preferably, mammalian polypeptides (polypeptides that were originally derived from a mammalian organism) are used, more preferably those which are directly secreted into the medium.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses a polyclonal, a monoclonal antibody, a chimeric antibody, a bispecific antibody, dual-specific antibody, bifunctional antibody, a trispecific antibody, a multispecific antibody, a bispecific heterodimeric diabody, a bispecific heterodimeric IgG, a labeled antibody, a humanized antibody, a human antibody, and fragments thereof (such as Fab, Fab', F(ab')$_2$, Fv), single chain (ScFv) and domain antibodies (including, for example, shark and camelid antibodies), fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known. The invention also includes "antibody analog(s)," other non-antibody molecule protein-based scaffolds, e.g., fusion proteins and/or immunoconjugates that use CDRs to provide specific antigen binding. The antibodies of the invention can be derived from any species including, but not limited to mouse, human, camel, llama, fish, shark, goat, rabbit, chicken, horse and bovine.

The term "antibody" further includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HC VR or VH) and a heavy chain constant region. A "variable region" of an antibody refers to the variable region of the antibody light chain or the variable region of the antibody heavy chain, either alone or in combination. The heavy chain constant region comprises three domains, CH1, CH2 and CH3. The CH1 and CH2 domains are connected by a hinge region. Each light chain comprises a light chain variable region (abbreviated herein as LC VR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the CD3 antibody (or antigen-binding portion thereof) may be identical to the human germline sequences, or may be naturally or artificially modified. An amino acid consensus sequence may be defined based on a side-by-side analysis of two or more CDRs. The CDRs in each chain are held together in close proximity by the FRs and, with the CDRs from the other chain, contribute to the formation of the antigen binding site of antibodies.

The term "antigen-binding fragment," "antibody fragment," or "antigen-binding portion," as used herein, refers to one or more fragments of an antibody that retain the ability to specifically bind to an antigen. Examples of binding fragments encompassed within the term "antigen-binding fragment" of an antibody include (i) an antibody heavy chain variable domain (VH) and/or an antibody light chain variable domain (VL), or a pair of VH/VL derived from full length antibodies or antibody fragments such as a VH domain and/or a VL domain; (ii) a Fab fragment, a monovalent fragment consisting of the VL, VH, CL and CH1 domains; (iii) a Fab' fragment, which is essentially a Fab with part of the hinge region (e.g., Fundamental Immunology, Paul ed., 3.sup.rd ed.1993; (iv) a F(ab')2 fragment, a bivalent fragment comprising two Fab fragments linked by a disulfide bridge at the hinge region; (v) a Fd fragment consisting of the VH and CH1 domains; (vi) an Fv fragment consisting of the VL and VH domains of a single arm of an antibody; (vii) a single chain Fv fragment (scFv), a single protein chain in which the VL and VH regions pair to form monovalent molecules (e.g., Bird et al. (1988) Science 242:423-426; and Huston et al. (1988) Proc. Natl. Acad. Sci. USA 85:5879-5883); (viii) a disulfide stabilized Fv fragment (dsFv), an Fv with an engineered intermolecular disulfide bond to stabilize the VH-VL pair; (ix) a single variable domain antibody (sdAb or dAb) fragment (e.g., Ward et al., (1989) Nature 341:544-546), which is composed of a variable domain of heavy chain and devoid of the light chain; (x) a complementarity determining region (CDR); and any derivatives thereof.

As used herein, an "antigen-binding fragment" of an antibody may comprise at least one variable domain. The variable domain may be of any size or amino acid composition and will generally comprise at least one CDR which is adjacent to or in frame with one or more framework sequences. As used herein, an "antigen-binding fragment of an antibody" may comprise a homo-dimer or hetero-dimer (or other multimer) of any of the variable region and constant domain configurations listed below in non-covalent association with one another and/or with one or more monomeric VH or VL region (e.g., by disulfide bond(s)). For example, the variable region may be dimeric and contain VH-VH, VH-VL or VL-VL dimers. The configurations of variable and constant domains that may be found within an antigen-binding fragment of an antibody of the present invention include: VH-CH1; VH-CH2, VH-CH3, VH-CH1-CH2, VH-CH1-CH2-CH3, VH-CH2-CH3, VH-VL-CL, VH-VL-CH1, VH-VL-CH2, VH-CL; VL-CH1; VL-CH2, VL-CH3, VL-CH1-CH2, VL-CH1-CH2-CH3, VL-CH2-CH3, and VL-CL. The variable regions and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable regions and/or constant domains in a single polypeptide molecule.

As used herein, a "binding domain" comprises any region of a polypeptide (e.g., antibody) which is responsible for selectively binding to a molecule of interest (e.g. an antigen, ligand, receptor, substrate or inhibitor). Exemplary binding domains include an antibody variable region, receptor binding domain, ligand binding domain and an enzymatic domain.

As used herein, the term "human acceptor framework" is a framework comprising the amino acid sequence of a light chain variable (VL) framework or a heavy chain variable (VH) framework derived from a human immunoglobulin framework or a human consensus framework, as defined below. A human acceptor framework "derived from" a human immunoglobulin framework or a human consensus framework may comprise the same amino acid sequence thereof, or it may contain amino acid sequence modifications. In some embodiments, the number of amino acid modifications are 10 or less, 9 or less, 8 or less, 7 or less, 6 or less, 5 or less, 4 or less, 3 or less, or 2 or less. In some embodiments, the VL human acceptor framework is identical in sequence to the VL human immunoglobulin framework sequence or human consensus framework sequence.

As used herein, an "affinity matured" antibody refers to an antibody with one or more modifications in one or more variable regions (which include the CDRs and FRs compared to a parent antibody, which does not possess such modifications, and wherein such modifications result in an improvement in the affinity of the antibody for an antigen.

As used herein, the term "Fc region," "Fc domain," "Fc chain" or analogous terms are used to define a C-terminal region of an IgG heavy chain. The Fc region of an IgG comprises two constant domains, CH2 and CH3. The CH2 domain of a human IgG Fc region usually extends from amino acids 231 to amino acid 340 according to the numbering system of the EU Index, or from amino acid 244 to amino acid 360 according to the numbering system of Kabat. The CH3 domain of a human IgG Fc region usually extends from amino acids 341 to 447 according to the numbering system of the EU index or from amino acid 361 to amino acid 478 according to the numbering system of Kabat. The CH2 domain of a human IgG Fc region (also referred to as "Cγ 2" domain) is unique in that it is not closely paired with another domain. Rather, two N-linked branched carbohydrate chains are interposed between the two CH2 domains of an intact native IgG. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

In certain embodiments, an Fc chain begins in the hinge region just upstream of the papain cleavage site and ends at the C-terminus of the antibody. Accordingly, a complete Fc chain comprises at least a hinge domain, a CH2 domain, and a CH3 domain. In certain embodiments, an Fc chain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc chain (i.e., a hinge domain, a CH2 domain, and a CH3 domain). In certain embodiments, an Fc chain comprises a hinge domain (or portion thereof) fused to a CH3 domain (or portion thereof). In certain embodiments, an Fc chain comprises a CH2 domain (or portion thereof) fused to a CH3 domain (or portion thereof). In certain embodiments, an Fc chain consists of a CH3 domain or portion thereof. In certain embodiments, an Fc chain consists of a hinge domain (or portion thereof) and a CH3 domain (or portion thereof). In certain embodiments, an Fc chain consists of a CH2 domain (or portion thereof) and a CH3 domain. In certain embodiments, an Fc chain consists of a hinge domain (or portion thereof) and a CH2 domain (or portion thereof). In certain embodiments, an Fc chain lacks at least a portion of a CH2 domain (e.g., all or part of a CH2 domain). An Fc chain herein generally refers to a polypeptide comprising all or part of the Fc chain of an immunoglobulin heavy-chain. This includes, but is not limited to, polypeptides comprising the entire CHl, hinge, CH2, and/or CH3 domains as well as fragments of such peptides comprising only, e.g., the hinge, CH2, and CH3 domain. The Fc chain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc chain includes molecules in monomeric or multimeric form, whether digested from whole antibody or produced by other means. In some embodiment, the Fc chain comprises the carboxy-terminal portions of both heavy chains held together by disulfides. In certain embodiments, an Fc chain consists of a CH2 domain and a CH3 domain.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII) subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

A "native sequence Fc region" or "wild-type Fc region" comprises an amino acid sequence identical to the amino acid sequence of an Fc region found in nature. By "wild-type" human IgG Fc it is meant a sequence of amino acids that occurs naturally within the human population. Of course, just as the Fc sequence may vary slightly between individuals, one or more alterations may be made to a wild-type sequence and still remain within the scope of the invention. For example, the Fc region may contain additional alterations that are not related to the present invention, such as a mutation in a glycosylation site, inclusion of an unnatural amino acid, or a "knobs-in-holes" mutation.

A "variant Fc region" or "variant Fc chain" comprises an amino acid sequence which differs from that of a native sequence Fc region by virtue of at least one amino acid modification yet retains at least one effector function of the native sequence Fc region. In some embodiments, the variant Fc chain has at least one amino acid substitution compared to a native sequence Fc chain or to the Fc region of a parent polypeptide, e.g., from about one to about ten amino acid substitutions, and preferably, from about one to about five amino acid substitutions in a native sequence Fc chain or in the Fc chain of the parent polypeptide. The variant Fc chain herein will preferably possess at least about 80% sequence identity with a native sequence Fc chain and/or with an Fc chain of a parent polypeptide, and most preferably, at least about 90% sequence identity therewith, more preferably, at least about 95%, at least about 96%, at least about 97%, at least about 98%, at least about 99% sequence identity therewith.

As used herein, the term "effector functions" refer to those biological activities attributable to the Fc chain (a native sequence Fc chain or amino acid sequence variant Fc chain) of an antibody, and vary with the antibody isotype. Examples of antibody effector functions include: C1q binding and complement dependent cytotoxicity; Fc receptor binding; antibody-dependent cell-mediated cytotoxicity (ADCC), phagocytosis; down regulation of cell surface receptors (e.g., B cell receptor); and B cell activation. Such effector functions generally require the Fc chain to be combined with a binding domain (e.g., an antibody variable region) and can be assessed using various assays known in the art for evaluating such antibody effector functions. An exemplary measurement of effector function is through Fcγ3 and/or C1q binding.

The effector functions of antibodies are determined by sequences in the Fc chain; this chain is also the part recognized by Fc receptors (FcR) found on certain types of cells.

In some embodiments, an Fc polypeptide comprises part or all of a wild-type hinge sequence (generally at its N-terminal). In some embodiments, an Fc polypeptide does not comprise a functional or wild-type hinge sequence.

The "hinge region," "hinge sequence," and variations thereof, as used herein, include the meaning known in the art, which is illustrated in, for example, Janeway et al., ImmunoBiology: the immune system in health and disease, Elsevier Science Ltd., NY (4th ed., 1999); Bloom et al., Protein Science, 6:407-415, 1997; and Humphreys et al., J. Immunol. Methods, 209:193-202, 1997.

The "immunoglobulin-like hinge region," "immunoglobulin-like hinge sequence," or variations thereof, as used herein, refers to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG½ hinge region.

In some embodiments, the hinge region can be from the human IgG1 subtype extending from amino acid 216 to amino acid 230 according to the numbering system of the EU index, or from amino acid 226 to amino acid 243 according to the numbering system of Kabat. In some embodiments the sequence may be EPKSCDKTHTCPPCP (SEQ ID NO: 63). Those of skill in the art may differ in their understanding of the exact amino acids corresponding to the various domains of the IgG molecule. Thus, the N-terminal or C-terminal of the domains outlined above may extend or be shortened by 1, 2, 3, 4, 5, 6, 7, 8, 9, or even 10 amino acids.

In some embodiments, the hinge region may be mutated by one or more amino acids. In some embodiments, the hinge region may be truncated and contain only a portion of the full hinge region. In some embodiments, the hinge region may contain only the last 5 amino acids of the hinge region, referred to here as the "lower hinge" region. In some embodiments, the lower hinge region may be comprised of the amino acids CPPCP (SEQ ID NO: 64) or from amino acid 226 to amino acid 230 according to the numbering system of the EU index or amino acid 239 to amino acid 243 according to the numbering system of Kabat.

As used herein, the term "modification" refers to an amino acid substitution, insertion, and/or deletion in a polypeptide sequence, an alteration to a moiety chemically linked to a protein, or a modification of a function of a protein, e.g., an antibody. For example, a modification may be an altered function of an antibody, or an altered carbohydrate structure attached to a protein. As used herein, an "amino acid modification" refers to a mutation (substitution), insertion (addition), or deletion of one or more amino acid residue in an antibody. The term "amino acid mutation" denotes the substitution of at least one existing amino acid residue with another different amino acid residue (e.g. the replacing amino acid residue). The term "amino acid deletion" denotes the removal of at least one amino acid residue at a predetermined position in an amino acid sequence. For example, the mutation L234A denotes that the amino acid residue lysine at position 234 in an antibody Fc-region is substituted by the amino acid residue alanine (substitution of lysine with alanine) (numbering according to the EU index numbering system). A "naturally occurring amino acid residue" denotes an amino acid residue from the group consisting of alanine (three letter code: Ala, one letter code: A), arginine (Arg, R), asparagine (Asn, N), aspartic acid (Asp, D), cysteine (Cys, C), glutamine (Gin, Q), glutamic acid (Glu, E), glycine (Gly, G), histidine (His, H), isoleucine (He, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

The term "agent" is used herein to denote a biological macromolecule, an extract made from biological materials, a mixture of biological macromolecules, a chemical compound, a mixture of chemical compounds, and/or a mixture of chemical compounds and biological macromolecules. The term "therapeutic agent" refers to an agent that has biological activity.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

Antibodies of the present invention can be "humanized antibodies". As used herein, "humanized" antibody refers to forms of non-human (e.g., mouse, rat, rabbit, non-human primate or other mammal) antibodies that are chimeric immunoglobulins, immunoglobulin chains, or fragments thereof (such as Fv, Fab, Fab', F(ab')2 or other antigen binding subsequences of antibodies) that contain one or more amino acid residues introduced into it from a source which is non-human. These non-human amino acid residues are often referred to as "import" residues, which are typically taken from an "import" variable domain. An import residue, sequence, or antibody has a desired affinity and/or specificity, or other desirable antibody biological activity as discussed herein.

Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable regions, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc chains modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody. Humanized as used herein is intended to include de-immunized antibodies.

As used herein, "human antibody" means an antibody having an amino acid sequence corresponding to that of an antibody produced by a human and/or which has been made using any of the techniques for making human antibodies known to those skilled in the art or disclosed herein. Accordingly, the term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boemer et al., J. Immunol., 147(1):86-95, 1991; and U.S. Pat. No. 5,750,373.

The human antibodies of the present invention can exist in at least two forms that are associated with hinge heterogeneity. For example, the immunoglobulin molecule comprises a stable four chain construct of approximately 150-160 kDa in which the dimers are held together by an interchain heavy chain disulfide bond. Alternatively, the dimers are not linked via inter-chain disulfide bonds and a molecule of about 75-80 kDa is formed composed of a covalently coupled light and heavy chain (half-antibody).

As used herein, the term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855, 1984). Chimeric antibodies of interest herein include primatized antibodies comprising variable region antigen-binding sequences derived from a non-human primate (e.g., Old World Monkey, Ape, etc.) and human constant region sequences.

A "monovalent antibody" comprises one antigen binding site per molecule (e.g., IgG or Fab). In some instances, a monovalent antibody can have more than one antigen binding sites, but the binding sites are from different antigens.

A "monospecific antibody" refers to an antibody or antibody preparation that comprises two identical antigen binding sites per molecule (e.g., IgG) such that the two binding sites bind identical epitope on the antigen. Thus, they compete with each other on binding to one antigen molecule. This term includes a "monoclonal antibody" or "monoclonal antibody composition." Most antibodies found in nature are monospecific. In some instances, a monospecific antibody can also be a monovalent antibody (e.g., Fab).

The terms "mutation load," "mutational load," "mutation burden," or "mutational burden" are used interchangeably herein. Tumor mutational load is a measure of the number of mutations within a tumor genome, defined as the total number of mutations per coding area of a tumor genome. There is large variability in mutation burden within tumor types, ranging from just a few to 1000s of mutations (Alexandrov L B et al., Nature 2013; 500(7463):415-421; Lawrence M S et al., Nature 2013; 499:214-218; Vogelstein B et al., Science, 2013; 339:1546-1558.

An "original amino acid residue" is one which is replaced by an "import amino acid" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. In some embodiments, the method of the instant invention involves replacing at least one original amino acid residue, but more than one original residue can be replaced. Normally, no more than the total residues in the interface of the first or second polypeptide may comprise original amino acid residues which are replaced.

The term "compete", as used herein with regard to an antibody, means that a first antibody, or an antigen-binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "antibody-dependent cell-mediated cytotoxicity" or "ADCC" refers to a cell-mediated reaction in which nonspecific cytotoxic cells that express Fc receptors (FcRs) (e.g., natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., PNAS (USA), 95:652-656, 1998.

As used herein, a "complement dependent cytotoxicity" or "CDC" refers to the lysing of a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods, 202: 163, 1996, may be performed.

As used herein, the terms "immunospecifically binds," "immunospecifically recognizes," "specifically binds," "specifically recognizes" and analogous terms refer to molecules e.g., binding domains that specifically bind to an antigen (e.g., epitope or immune complex) and do not specifically bind to another molecule. A molecule that specifically binds to an antigen may bind to other peptides or polypeptides with lower affinity as determined by assays known in the art e.g., immunoassays, BIACORE™, or other assays. Preferably, molecules that specifically bind an antigen do not cross-react with other proteins.

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

The binding proteins, binding domains, CDRs, or antibodies (as broadly defined herein) can be identified according to the definitions of the Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., Nature 342:877-883, 1989 (structural loop structures). The identity of the amino acid residues in a particular antibody that make up a CDR can be determined using methods well known in the art. AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., J. Mol. Biol., 262:732-745, 1996. The "conformational" definition of CDRs is based on residues that make enthalpic contributions to antigen binding (see, e.g., Makabe et al., J. Biol. Chem., 283:1156-1166, 2008). North has identified canonical CDR conformations using a different preferred set of CDR definitions (North et al., J. Mol. Biol. 406: 228-256, 2011). In another approach, referred to herein as the "conformational definition" of CDRs, the positions of the CDRs may be identified as the residues that make enthalpic contributions to antigen binding (Makabe et al., J Biol. Chem. 283:1156-1166, 2008). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, extended (combination of Kabat and Chothia), North, extended, AbM, contact, and/or conformational definitions.

Residues in a variable domain are numbered according to Kabat, which is a numbering system used for heavy chain variable regions or light chain variable regions of the compilation of antibodies. See, Kabat et al., Sequences of Proteins of Immunological Interest, 5th Ed. Public Health Service, National Institutes of Health, Bethesda, Md., 1991. Using this numbering system, the actual linear amino acid sequence may contain fewer or additional amino acids corresponding to a shortening of, or insertion into, a FR or CDR of the variable region. For example, a heavy chain variable region may include a single amino acid insert (residue 52a according to Kabat) after residue 52 of H2 and inserted residues (e.g., residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) was used herein to assign Kabat numbering to variable regions VL CDR1, VL CDR2, VL CDR3, VH CDR1, VH CDR2, and VH CDR3. Specific amino acid residue positions in an antibody may also be numbered according to Kabat.

As used herein, the term "phage display library" refers to a population of bacteriophage, each of which contains a foreign cDNA recombinantly fused in frame to a surface protein. The phage displays the foreign protein encoded by the cDNA on its surface. After replication in a bacterial host, typically E. coli, the phage which contains the foreign cDNA of interest are selected by the expression of the foreign protein on the phage surface.

The term "epitope" refers to that portion of a molecule capable of being recognized by, making contact and/or being bound by an antibody at one or more of the antibody's antigen-binding regions known as a paratope. A single antigen may have more than one epitope. Thus, different antibodies may bind to different areas on an antigen and may have different biological effects. Epitopes often consist of a chemically active surface grouping of molecules such as amino acids or sugar side chains and have specific three-dimensional structural characteristics as well as specific charge characteristics. As used herein, epitopes may be either conformational or linear. A conformational epitope is produced by spatially juxtaposed amino acids from different segments of the linear polypeptide chain. A linear epitope is one produced by adjacent amino acid residues in a polypeptide chain. In certain embodiments, an epitope may include moieties of saccharides, phosphoryl groups, or sulfonyl groups on the antigen.

The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds. Once a desired epitope on an antigen is determined, it is possible to generate antibodies to that epitope, so e.g., using the techniques described herein.

The terms "specific binding" or "specifically binding" when used in reference to the interaction of an antibody and a protein or peptide refers to an interaction that is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

In certain embodiments "specifically binds" means, for instance, that an antibody binds a protein with a KD of about 0.1 nM or less, but more usually less than about 1 µM. In certain embodiments, "specifically binds" means that an antibody binds a target at times with a KD of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human protein or mouse protein). Likewise, because of homology within certain regions of polypeptide sequences of different proteins, specific binding can include an antibody that recognizes more than one protein. It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in some embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be multispecific and comprise at least two antigen-binding sites with differing specificities. By way of non-limiting example, a bispecific antibody may comprise one antigen-binding site that recognizes an epitope on one protein (e.g., human CD3) and further comprise a second, different antigen-binding site that recognizes a different epitope on a second protein. Generally, but not necessarily, reference to binding means specific binding.

An antibody that specifically binds to an antigen may bind to other peptides or polypeptides with lower affinity as determined by assays known in the art e.g. immunoassays, BIACORE®, or other assays. Preferably, the antibody that specifically binds an antigen does not cross-react with other proteins.

The terms "non-specific binding" or "background binding" when used in reference to the interaction of an antibody and a protein or peptide refers to an interaction that is not dependent on the presence of a particular structure (i.e., the antibody is binding to proteins in general rather that a particular structure such as an epitope).

The term "$k_{on}$" or "$k_a$," as used herein, refers to the rate constant for association of an antibody to an antigen. Specifically, the rate constants ($k_{on}/k_a$ and $k_{off}/k_d$) and equilibrium dissociation constants are measured using whole antibody (i.e., bivalent) and monomeric CD3 proteins.

The term "$k_{off}$" or "$k_d$," as used herein, refers to the rate constant for dissociation of an antibody from the antibody/antigen complex.

The term "$K_D$," as used herein, refers to the equilibrium dissociation constant of an antibody-antigen interaction.

As used herein, the term "binding affinity," generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. In particular, the term "binding affinity" is intended to refer to the dissociation rate of a particular antigen-antibody interaction. The $K_D$ is the ratio of the rate of dissociation, also called the "off-rate ($k_{off}$)," to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 µM indicates weak binding affinity compared to a $K_D$ of 1 nM. $K_D$ values for antibodies can be determined using methods well established in the art. One method for determining the $K_D$ of an antibody is by using surface plasmon resonance (SPR), typically using a biosensor system such as a BIACORE™ system. BIACORE™ kinetic analysis comprises analyzing the binding and dissociation of an antigen from chips with immobilized molecules (e.g., molecules comprising epitope binding domains), on their surface. Another method for determining the $K_D$ of an antibody is by using Bio-Layer Interferometry, typically using OCTET® technology (Octet $QK^e$ system, ForteBio).

"Biologically active," "biological activity" and "biological characteristics" with respect to an antibody of the present invention, such as an antibody, fragment, or derivative thereof, means having the ability to bind to a biological molecule, except where specified otherwise.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

The present invention also includes polynucleotides that encode the antibodies of the invention, including the polypeptides and binding regions of the antibodies. The polynucleotides encoding the molecules of the invention may be obtained, and the nucleotide sequence of the polynucleotides determined, by any method known in the art.

The polynucleotides that encode the antibodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term "polynucleotide encoding an antibody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART® AG, Regensburg, Germany).

The antibodies of the present invention may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie, J U et al. Science 247: 1306-1310, 1990 or Padlan et al. FASEB J. 9: 133-139, 1995.

As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, a "non-essential" amino acid residue is a residue that can be altered from the wild-type sequence of the binding agent, e.g., the antibody, without abolishing or, without substantially altering a biological activity, whereas an "essential" amino acid residue results in such a change. In an antibody, an essential amino acid residue can be a specificity determining residue (SDR).

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or polypeptide that is separated from some or all of the coexisting materials in the natural system is isolated. Such polynucleotide could be part of a vector and/or such polynucleotide or polypeptide could be part of a composition, e.g., a mixture, solution or suspension or comprising an isolated cell or a cultured cell which comprises the polynucleotide or polypeptide, and still be isolated in that the vector or composition is not part of its natural environment. For example, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 50%, 40%, 30%, 20%, 10%, 5%, 2.5% or 1%, (by dry weight) of contaminating protein. When the antibody is recombinantly produced, it is also preferably substantially free of culture medium, i.e., culture medium represents less than about 50%, 40%, 30%, 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 50%, 40%, 30%, 20%, 10%, 5% or 1% (by dry weight) of chemical precursors or compounds other than antibody of interest. In a preferred embodiment of the present invention, antibodies are isolated or purified. An antibody that has been separated or removed from at least one component of an organism, or from a tissue or cell in which the antibody naturally exists or is naturally produced, is an "isolated antibody" for purposes of the present invention.

The term "recovering" as used herein, refers to the process of rendering a chemical species such as a polypeptide substantially free of naturally associated components by isolation, e.g., using protein purification techniques well known in the art.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. For example, a control sequence "operably linked" to a coding sequence is ligated in such a manner that expression of the coding sequence is achieved under conditions suitable or compatible with the control sequence. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "expression control sequence" or "control sequence" refers to a polynucleotide sequence that is necessary to effect the expression of a coding sequence to which it is ligated. The nature of such control sequences differs depending upon the host organism. For example, in prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "mammalian cells" include reference to cells derived from mammals including humans, rats, mice, guinea pigs, chimpanzees, or macaques. The cells may be cultured in vivo or in vitro.

As used herein, the term "purified product" refers to a preparation of the product which has been isolated from the cellular constituents with which the product is normally associated and/or from other types of cells that may be present in the sample of interest.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

As used herein, the term "treat," "treating" or "treatment" is an approach for obtaining beneficial or desired clinical results. For the purpose of the present invention, treatment is defined as the administration of an CD3 antibody molecule (e.g., monoclonal antibody, bispecific antibody) to a subject, e.g., a patient, or administration, e.g., by application, to an isolated tissue or cell from a subject which is returned to the subject. The CD3 antibody molecule can be administered alone or in combination with one or more agents. The treatment can be to cure, heal, alleviate, relieve, alter, remedy, ameliorate, palliate, improve or affect the disorder, the symptoms of the disorder or the predisposition toward the disorder, e.g., a cancer.

As used herein, the term "subject" is intended to include any animal (e.g., a mammal), including, but not limited to, humans, non-human primates, rodents, and the like, which is to be the recipient of a particular treatment. For example, a subject can be a patient (e.g., a human patient or a veterinary patient), having a cancer. Typically, the terms "subject," "individual" and "patient" are used interchangeably herein in reference to a human subject.

The term "non-human animals" of the invention includes all non-human vertebrates, e.g., non-human mammals and non-mammals, such as non-human primates, sheep, dog, cow, chickens, amphibians, reptiles, mouse, rat, rabbit or goat etc., unless otherwise noted.

As used herein, the term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

As used herein, the terms "pharmaceutically acceptable excipient, carrier or adjuvant" or "acceptable pharmaceutical carrier" refer to an excipient, carrier or adjuvant that can be administered to a subject, together with at least one antibody of the present disclosure, and which does not destroy the activity of the antibody. The excipient, carrier or adjuvant should be nontoxic when administered with an antibody in doses sufficient to deliver a therapeutic effect.

As used herein, the term "ameliorating" means a lessening or improvement of one or more symptoms as compared to not administering an antibody molecule of the invention. "Ameliorating" also includes shortening or reduction in duration of a symptom.

As used herein, the terms "prevent", "preventing" and "prevention" refer to the prevention of the recurrence or onset of one or more symptoms of a disorder in a subject as result of the administration of a prophylactic or therapeutic agent.

As used herein, an "effective amount," "therapeutically effective amount," "therapeutically sufficient amount," or "effective dosage" refers to that amount of a therapeutic agent (e.g., CD3 antibody, either alone or as a part of a multispecific antibody (e.g., bispecific)), which is effective or sufficient, upon single or multiple dose administration to a subject, in preventing, healing, ameliorating, treating or managing a disease, disorder or side effect, or decreasing the rate of advancement of a disease or disorder, or in prolonging curing, alleviating, relieving, or improving the condition of a subject with a disorder as described herein beyond that expected in the absence of such treatment. The term also includes within its scope amounts effective to enhance normal physiological function. An effective amount may be considered in the context of administering one or more therapeutic agents, and a single agent may be considered to be given in an effective amount if, in conjunction with one or more other agents, a desirable result may be or is achieved.

As used herein, the effective agent is capable of targeting effector T cells to induce T-cell-mediated cytotoxicity of cells associated with a disease, such as cancer, autoimmune disease or infectious disease. The therapeutic agent of the present invention introduces the T cell mediated immune response, by modulating a CD3 antigen on the T cell surface, particularly CD3, more particularly CD3 epsilon.

With respect to cancer, a therapeutically effective amount refers to the amount of therapeutic agent that inhibits growth of a tumor or cancer by slowing, interrupting, arresting or stopping its growth and/or metastases.

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. As used herein, the term "half maximal effective concentration ($EC_K$)" refers to the concentration of a therapeutic agent which causes a response halfway between the baseline and maximum after a specified exposure time. The therapeutic agent may cause inhibition or stimulation. The $EC_{50}$ value is commonly used, and is used herein, as a measure of potency.

As used herein, "combination therapy" or administration "in combination with" refers to the use of more than one prophylactic and/or therapeutic agent. The use of the term "combination therapy" or "in combination" does not restrict the order in which prophylactic and/or therapeutic agents are administered to a subject with a disorder. In other words, the combination therapy may be done by separately, sequentially, or simultaneously treating with the therapeutic agents. In the case of "sequential administration," the first administered agent may be exerting some physiological effect on the subject when the second agent is administered or becomes active in the subject.

The term "simultaneous administration" as used herein in relation to the administration of prophylactic and/or therapeutic agent refers to the administration of agents such that the individual agents are present within a subject at the same time. Simultaneous administration may be effected by the molecules being formulated in a single composition, or in separate compositions administered at the same or similar time. Sequential administration may be in any order as required.

The term "cluster of differentiation 3" or "CD3" refers a multimeric protein complex, known historically as the T3 complex, and is composed of four distinct polypeptide chains; epsilon (ε), gamma (γ), delta (δ) and zeta (ζ) that assemble and function as three pairs of dimers (εγ, εδ, ζζ). The CD3 complex serves as a T cell co-receptor that associates noncovalently with the T cell receptor (TCR) (Smith-Garvin et al. 2009) and generate an activation signal in T lymphocytes. The CD3 protein complex is a defining feature of the T cell lineage, therefore CD3 antibodies can be used effectively as T cell markers (Chetty and Gatter 1994). It is well known that CD3 antibodies elicit the generation of cytotoxic T cells through the activation of endogenous lymphokine production and are capable of selectively killing tumor targets (Yun et al., Cancer Research, 49: 4770-4774 (1989)).

T cells play a central role in cell-mediated immunity in humans and animals. The recognition and binding of a particular antigen is mediated by the TCRs expressed on the surface of T cells. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. More specifically, T cells express TCR complexes that are able to induce antigen specific immune responses (Smith-Garvin et al, 2009). Antigens are peptides expressed by tumor cells and virally infected cells capable of stimulating immune responses. Intracellularly expressed antigens are bound to major histocompatibility class I (MHC class I) molecules and transported to the surface where they are exposed to T cells. If the binding affinity of the TCR to the MHC class I in complex with the antigen is sufficient the formation of an immune synapse will be initiated. Signaling through the immune synapse is mediated through the CD3 co-receptors that form epsilon/delta, delta/gamma and zeta/zeta dimers. These dimers associate with the TCR and generate an activation signal in T lymphocytes. This signaling cascade directs T cell mediated killing of the cell expressing the antigen. Cytotoxicity is mediated by release and transfer of granzyme B and perforin from the T cell to the target cell.

As used herein, an "activating T cell antigen" refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 130), NCBI RefSeq no. NP_000724.1, SEQ ID NO: 66 for the human sequence. Typically, a naturally occurring allelic variant has an amino acid sequence at least 95%, 97% or 99% identical to the protein described in GenBank Accession No.: BAB71849.1.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

As used herein, an "antibody that binds CD3", an "antibody that recognizes CD3", an "anti-CD3 antibody" or a "CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The human CD3 epsilon is indicated in GenBank Accession No. NM_000733. The antibodies of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

Antibodies directed against CD3 are able to generate an activation signal in T lymphocytes. Other T cell activation ligands can be used as well, including without limitation CD28, CD134, CD137, and CD27.

The present invention includes one-arm antibodies that bind CD3. As used herein, a "one-arm antibody" means an antigen-binding molecule comprising a single antibody heavy chain and a single antibody light chain. The one-arm antibodies of the present invention may comprise any of the VL/VH or CDR amino acid sequences as set forth in Tables 1, 2 and 3 herein.

The CD3 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In some embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In some further embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies that contain one or more germline mutations can be easily tested for one or more desired property such as, improved binding specificity, increased binding affinity, improved or enhanced antagonistic or agonistic biological properties (as the case may be), reduced immunogenicity, etc. Antibodies obtained in this general manner are encompassed within the present invention.

The present invention also includes CD3 antibodies comprising variants of any of the VH, VL, and/or CDR amino acid sequences disclosed herein having one or more conservative substitutions. For example, the present invention includes CD3 antibodies having VH, VL, and/or CDR amino acid sequences with, e.g., 10 or fewer, 8 or fewer, 6 or fewer, 4 or fewer, etc. conservative amino acid substitutions relative to any of the VH, VL, and/or CDR amino acid sequences set forth in Table 1 herein.

As used herein, the term "complex" or "complexed" refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

As used herein, the "CD3 antibody" includes monovalent antibodies with a single specificity, as well as "bispecific antibody," "dual-specific antibody," trispecific antibodies," "bifunctional antibody," "heteromultimer," "heteromultimeric complex," "bispecific heterodimeric diabody," "heteromultimeric polypeptide," or bispecific heterodimeric IgGs. In some embodiments of the invention, the CD3 antibodies of the invention are human or humanized antibodies.

As used herein, a "bispecific antibody" is a molecule comprising at least a first polypeptide and a second polypeptide, wherein the second polypeptide differs in amino acid sequence from the first polypeptide by at least one amino acid residue. In some instances, the bispecific is an artificial hybrid antibody having two different heavy chain region and light chain region. Preferably, the bispecific antibody has binding specificity for at least two different ligands, antigens or binding sites. Accordingly, the bispecific antibodies can bind simultaneously two different antigens. The two antigen binding sites of a bispecific antibody bind to two different epitopes, which may reside on the same or different protein targets, e.g., tumor target.

As used herein, the first polypeptide chain and the second polypeptide chain of the "bispecific antibody" comprise at least one antibody VL and one antibody VH region or fragment thereof, wherein both antibody binding domains are comprised within a single polypeptide chain and wherein the VL and VH regions in each polypeptide chain are from different antibodies.

Bispecific antibodies can be derived from full length antibodies or antibody fragments (e.g., F(ab')2 bispecific antibodies). Diabodies are described more fully in, for example, EP404,097; WO93/11161; and Hollinger et al., Proc. Natl. Acad. Sci. USA 90:6444-6448, 1993. Bispecific antibodies are heterodimers of two "crossover" sFv fragments in which the VH and VL regions of the two antibodies are present on different polypeptide chains.

As used herein, the terms "linked," "fused," "fusion," "covalently bound," "covalently coupled" and "genetically fused" are used interchangeably. These terms refer to the joining together of two more elements or components, by whatever means including chemical conjugation or recombinant means. As used herein, the term "covalently bound" means that the specified moieties are either directly covalently bonded to one another, or else are indirectly covalently joined to one another through an intervening moiety or moieties, such as a linking peptide or moiety. In a preferred embodiment, moieties are covalently fused. One type of covalent linkage is a peptide bond. Methods of chemical conjugation (e.g., using heterobifunctional cross-linking agents) are known in the art. Fused moieties may also be genetically fused. As used herein, the term "genetically fused," "genetically linked" or "genetic fused" refers to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

As used herein, the term "linked" or "links" refers to either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

As used herein, the term "linker" refers to an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

As used herein, the term "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody. Cysteine residues can be introduced, e.g., by site directed mutagenesis, so that stabilizing disulfide bonds can be made within the molecule.

The "knob-in-hole designation" is analogous to the "protuberance and cavity" designation and may be used interchangeably.

A "protuberance" or "knob" refers to at least one amino acid side chain which projects from the interface of the first polypeptide and is therefore positionable in a compensatory cavity in the adjacent interface (i.e., the interface of the second polypeptide) so as to stabilize the heterodimer, and thereby favor heterodimer formation over homodimer formation, for example. The protuberance may exist in the original interface or may be introduced synthetically (e.g., by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. The upper limit for the number of original residues which are replaced is the total number of residues in the interface of the first polypeptide. Certain import residues for the formation of a protuberance are generally naturally occurring amino acid residues and are preferably selected from arginine (R), phenylalanine (F), tyrosine (Y) and tryptophan (W).

The protuberance or knob is "positionable" in the cavity or hole which means that the spatial location of the protuberance and cavity on the interface of the first polypeptide and second polypeptide respectively and the sizes of the protuberance and cavity are such that the protuberance may be located in the cavity without significantly perturbing the normal association of the first and second polypeptides at the interface. Since protuberances such as phenylalanine (F), tyrosine (Y) and tryptophan (W) do not typically extend perpendicularly from the axis of the interface, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

A "cavity" or "hole" refers to at least one amino acid side chain which is recessed from the interface of the second polypeptide and therefore accommodates a corresponding protuberance on the adjacent interface of the first polypeptide. The cavity may exist in the original interface or may be introduced synthetically (e.g., by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. The upper limit for the number of original residues which are replaced is the total number of residues in the interface of the second polypeptide. Certain import residues for the formation of a cavity are usually naturally occurring amino acid residues and are preferably selected from alanine (A), serine (S), threonine (T) and valine (V).

A "target antigen," a "target cell antigen," a "tumor antigen," or a "tumor specific antigen," as used herein refers to an antigenic determinant presented on the surface of a target cell, for example a cell in a tumor such as a cancer cell or a cell of the tumor stroma.

As used herein, the term "cancer" or "cancerous" refers to or describes a physiological condition in mammals that is typically characterized by unregulated cell growth, a neoplasm or a tumor resulting from abnormal uncontrolled growth of cells. In some aspects, cancer refers to a malignant primary tumor without metastasis, which has remained localized. In other aspects, cancer refers to a malignant tumor, which has invaded and destroyed neighboring body structures and spread to distant sites. In some aspects, the cancer is associated with a specific cancer antigen. Examples of cancer include, but are not limited to, cancer of the oral cavity and pharynx, the digestive system (e.g., the esophagus, stomach, small intestine, colon, rectum, liver, gall bladder, bile ducts, and pancreas), the respiratory system (e.g., the larynx, lung, and bronchus, including non-small cell lung carcinoma), bones and joints (e.g., bone metastases), soft tissue, the skin (e.g., melanoma), breast, the genital system (e.g., the uterine cervix, uterine corpus, ovary vulva, vagina, prostate, and testis), the urinary system (e.g., the urinary bladder, kidney, renal pelvis, and ureter), the eye and orbit, the brain and nervous system (e.g., glioma), head and neck, or the endocrine system (e.g., thyroid). The cancer also can be a lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). In certain embodiments, the cancer of digestive system is a cancer of the esophagus, stomach, small intestine, colon, rectum, liver, gall bladder, bile ducts, and pancreas.

With respect to cancer, the treatment is useful in any one or more of the following: (a) treating, preventing, or ameliorating one or more symptoms of a condition associated with malignant cells in a subject (e.g., gastrointestinal-related cancer such as colorectal cancer (CRC)); (b) inhibiting tumor growth or progression in a subject who has a malignant tumor expressing a tumor antigen; (c) inhibiting metastasis of cancer (malignant) cells expressing a tumor antigen in a subject who has one or more malignant cells expressing a tumor antigen; (d) inducing regression (e.g., long-term regression) of a tumor expressing a tumor antigen; (e) exerting cytotoxic activity in malignant cells expressing a tumor antigen; (f) increasing the progression-free survival of a subject with a tumor antigen associated disorder; (g) increasing the overall survival of a subject with a tumor antigen associated disorder; (h) reducing use of additional chemotherapeutic or cytotoxic agents in a subject with a tumor antigen associated disorder; (i) reducing the tumor burden in a subject with a tumor antigen associated disorder; or (j) blocking interaction of a tumor antigen with other yet to be identified factors. While not wishing to be bound by theory, treating is believed to cause the inhibition, ablation, or killing of a cell in vitro or in vivo, or otherwise reducing the capacity of a cell, including an aberrant cell, to mediate a disorder, e.g., a disorder as described herein such as cancer.

As used herein, the term "malignant cell" or "malignancy" refers to tumors or tumor cells that are invasive and/or able to undergo metastasis, i.e., a cancerous cell.

Although any materials and methods similar or equivalent to those described herein can be used in the practice or testing or testing of the present invention, the preferred materials and methods are now described.

Materials and Methods

Various techniques for the production of antibodies have been described which include the traditional hybridoma method for making monoclonal antibodies, recombinant techniques for making antibodies (including chimeric antibodies, e.g., humanized antibodies), antibody production in transgenic animals and the recently described phage display technology for preparing "fully human" antibodies. These techniques are described briefly below.

Polyclonal antibodies to the antigen of interest generally can be raised in animals by multiple subcutaneous (sc) or intraperitoneal (ip) injections of the antigen and an adjuvant. The antigen (or a fragment containing the target amino acid sequence) can be conjugated to a protein that is immunogenic in the species to be immunized, e.g., serum albumin, bovine thyroglobulin, or soybean trypsin inhibitor using a bifunctional or derivatizing agent, for example maleimidobenzoyl sulfosuccinimide ester (conjugation through cysteine residues), or N-hydroxysuccinimide (through lysine residues). Animals are immunized against the immunogenic conjugates or derivatives and a few weeks later the animals are boosted by subcutaneous injection at multiple sites. 7 to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are used to enhance the immune response.

Monoclonal antibodies can be obtained from a population of substantially homogeneous antibodies using the hybridoma method first described by Kohler & Milstein, Nature 256:495, 1975 or may be made by recombinant DNA methods (Cabilly et al., U.S. Pat. No. 4,816,567). In the hybridoma method, a mouse or other appropriate host animal is immunized as hereinabove described to elicit lymphocytes that produce, or are capable of producing, antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986). The hybridoma cells thus prepared are seeded and grown in a suitable culture medium that preferably contains one or more substances that inhibit the growth or survival of the unfused, parental myeloma cells. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, Protein A-Sepharose, hydroxylapatite chromatography, gel electrophoresis, dialysis, or affinity chromatography.

The expression of antibody, antigen-binding fragments of an antibody, or any antibody construct can be performed in appropriate prokaryotic or eukaryotic host cells like CHO cells, NSO cells, SP2/0 cells, HEK293 cells, COS cells, PER.C6 cells, yeast, or E. coli cells, and the secreted antibody is recovered and harvested from the cells (a cell culture supernatant, a conditioned cell culture supernatant, a cell lysate, or a clarified bulk.). General methods for production of antibodies are well-known in the state of the art and described, for example, in the review articles of Makrides, S. C., Protein Expr. Purif. 17:183-202, 1999; Geisse, S., et al., Protein Expr. Purif. 8:271-282, 1986;

Kaufman, R. J., Mol. Biotechnol. 16:151-160, 2000; Werner, R. G., Drug Res. 48:870-880, 1998. In a specific embodiment, the cell culture is a mammalian cell culture, such as a Chinese Hamster Ovary (CHO) cell culture.

In one embodiment, the antibody can be recovered or isolated from a source which naturally produces. In some such embodiments, the isolated or recovered antibodies can be subjected to additional purification steps by using conventional chromatography methods known in the art. In particular, methods of purification are contemplated to include, but are not limited to, affinity chromatography (e.g., a Protein A affinity chromatography), ion-exchange chromatography (e.g., an anion exchange chromatography or a cation exchange chromatography), hydrophobic interaction chromatography, hydroxylapatite chromatography, gel filtration chromatography and/or dialysis. Among those, a preferred purification method is using Protein A chromatography. The matrix to which the affinity ligand is attached is most often agarose, but other matrices are available.

Other techniques for antibody purification such as fractionation on an ion-exchange column, ethanol precipitation, reverse phase high pressure chromatography, ethanol precipitation, Reverse Phase HPLC, chromatography on silica, chromatography on heparin Sepharose™, chromatography on an anion or cation exchange resin (such as a polyaspartic acid column), chromatofocusing, electrophoresis using SDS-PAGE, and ammonium sulfate precipitation are also known in the art. The above list of purification methods is merely exemplary in nature, and is not intended to be a limiting recitation.

Alternatively, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551-255; 1993 and Jakobovits et al., Nature 362:255-258, 1993).

In some embodiments, the antibodies of the present invention can be humanized with retention of high affinity for the antigen and other favorable biological properties. Methods for humanizing non-human antibodies are well known in the art. Humanization can be essentially performed following the method of Winter and co-workers (Jones et al., Nature 321:522-525, 1986; Riechmann et al., Nature 332:323-327, 1988; Verhoeyen et al., Science 239: 1534-1536, 1988), by substituting rodent CDRs or CDR sequences for the corresponding sequences of a human antibody. Accordingly, such humanized antibodies are chimeric antibodies (Cabilly, supra), wherein substantially less than an intact human variable domain has been substituted by the corresponding sequence from a non-human species. In practice, humanized antibodies are typically human antibodies in which some CDR residues, and possibly some FR residues, are substituted by residues from analogous sites in rodent antibodies. It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. For further details see WO92/22653, published Dec. 23, 1992.

Antibodies of the present invention can also be generated using various phage display methods known in the art. In phage display methods, functional antibody domains are displayed on the surface of phage particles which carry the polynucleotide sequences encoding them. In a particular aspect, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods is typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkmann et al. "Phage Display Of Disulfide-Stabilized Fv Fragments," J. Immunol. Methods, 182:41-50, 1995.

The functional characteristics of the multiple IgG isotypes, and domains thereof, are well known in the art. The amino acid sequences of IgG1, IgG2, IgG3 and IgG4 are known in the art. Selection and/or combinations of two or more domains from specific IgG isotypes for use in the methods of the invention may be based on any known parameter of the parent isotypes including affinity to FcγR. For example, use of regions or domains from IgG isotypes that exhibit limited or no binding to FcγRIIB, e.g., IgG2 or IgG4, may find particular use where a bispecific antibody is desired to be engineered to maximize binding to an activating receptor and minimize binding to an inhibitory receptor. Similarly, use of Fc chains or domains from IgG isotypes known to preferentially bind C1q or FcγRIIIA, e.g., IgG3 may be combined with Fc amino acid modifications known in the art to enhance antibody-dependent cell mediated cytotoxicity (ADCC) and/or complement dependent cytotoxicity (CDC), to engineer a bispecific antibody such that effector function activity, e.g., complement activation or ADCC, is maximized. In a similar fashion, mutations may be made in the Fc chains or domains of IgG isotypes that minimize or eliminate the effector function of the Fc chain.

During the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another e.g., the antibodies compete for binding to the antigen. One method is to identify the epitope to which antibodies bind, or "epitope mapping". There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). In an additional example, mutagenesis of an antigen binding domain, domain swapping experiments and alanine scanning mutagenesis can be performed to identify residues required, sufficient, and/or necessary for epitope binding. The binding affinity and the off-rate of an antigen-binding domain interaction can be determined by competitive binding assays. One example of a competitive binding assay is a radioimmunoassay comprising the incubation of labeled antigen, and the detection of the molecule bound to the labeled antigen. The affinity of the molecule of the present invention for an antigen and the binding off-rates can be determined from the saturation data by Scatchard analysis.

The affinities and binding properties of the antibodies of the present invention for an antigen may be initially determined using in vitro assays (biochemical or immunological based assays) known in the art for antigen-binding domain, including but not limited to enzyme-linked immunosorbent assay (ELISA) assay, surface plasmon resonance (SPR) assay, Bio-Layer Interferometry, or immunoprecipitation assays. The molecules of the invention may have similar binding properties in vivo models (such as those described and disclosed herein) as those in in vitro based assays. However, the present invention does not exclude molecules of the invention that do not exhibit the desired phenotype in in vitro based assays but do exhibit the desired phenotype in vivo.

Once a nucleic acid sequence encoding molecules of the invention (i.e., binding domains) has been obtained, the vector for the production of the molecules may be produced by recombinant DNA technology using techniques well known in the art.

The polynucleotides encoding the antibody binding domains of the present invention may include an expression control polynucleotide sequence operably linked to the antibody coding sequences, including naturally-associated or heterologous promoter regions known in the art. The expression control sequences may be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Eukaryotic cell lines include the CHO cell lines, various COS cell lines, HeLa cells, myeloma cell lines, transformed B-cells, or human embryonic kidney cell lines.

In one embodiment, the DNA encoding the antibodies of the invention is isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., Proc. Nat. Acad. Sci. 81:6851, 1984. In that manner, chimeric antibodies are prepared that have the binding specificity of an anti-antigen monoclonal antibody herein.

CD3 Antibodies

In one aspect, the present invention provides agents that specifically bind CD3 (e.g., full-length human CD3 epsilon subunit (e.g., accession number NP_000724 or SEQ ID NO: 66)).

In certain embodiments, the CD3 antibody specifically binds human CD3.

Exemplary CD3 antibodies of the present invention are listed in Tables 1, 2 and 3 herein. Table 1 sets forth the amino acid sequence identifiers of the VH regions and VL regions. In some embodiments, provided is an antibody having any one of partial light chain sequence as listed in Table 1 and/or any one of partial heavy chain sequence as listed in Table 1.

TABLE 1

| Variant | Light Chain | Heavy Chain |
| --- | --- | --- |
| 2B5-0001 (2B5 antibody) | DIQMTQSPSSLSASVGDRVTITCTSS QSLFNVRSRKNYLAWYQQKPGKAP KLLIYWASTRESGVPSRFSGSGSGT DFTLTISSLQPEDFATYYCKQSYDLF TFGGGTKVEIK (SEQ ID NO: 1) | EVQLVESGGGLVQPGGSLRLSC AASGFTFSDYYMTWVRQAPGKG LEWVAFIRNRARGYTSDHNPSVK GRFTISRDNAKNSLYLQMNSLRA EDTAVYYCARDRPSYYVLDYWG QGTTVTVSS (SEQ ID NO: 2) |
| 2B5-0002 | DIQMTQSPSSLSASVGDRVTITCTSS QSLFNVRSQKNYLAWYQQKPGKAP KLLIYWASTRESGVPSRFSGSGSGT DFTLTISSLQPEDFATYYCKQSYDLF TFGGGTKVEIK (SEQ ID NO: 3) | EVQLVESGGGLVQPGGSLRLSC AASGFTFSDYYMTWVRQAPGKG LEWVAFIRNRARGYTSDHNPSVK GRFTISRDNAKNSLYLQMNSLRA EDTAVYYCARDRPSYYVLDYWG QGTTVTVSS (SEQ ID NO: 2) |

TABLE 1-continued

| Variant | Light Chain | Heavy Chain |
| --- | --- | --- |
| 2B5-0006 (2B5v6) | DIQMTQSPSSLSASVGDRVTITCTSSQSLFNVRSQKNYLAWYQQKPGKAPKLLIYWASTRESGVPSRFSGSGSGTDFTLTISSLQPEDFATYYCKQSYDLFTFGGGTKVEIK (SEQ ID NO: 3) | EVQLVESGGGLVQPGGSLRLSCAASGFTFSDYYMTWVRQAPGKGLEWVAFIRNQARGYTSDHNPSVKGRFTISRDNAKNSLYLQMNSLRAEDTAVYYCARDRPSYYVLDYWGQGTTVTVSS (SEQ ID NO: 4) |
| 2B5-0009 | DIQMTQSPSSLSASVGDRVTITCTSSQSLFNVRSQKNYLAWYQQKPGKAPKLLIYWASTRESGVPSRFSGSGSGTDFTLTISSLQPEDFATYYCKQSYDLFTFGGGTKVEIK (SEQ ID NO: 3) | EVQLVESGGGLVQPGGSLRLSCAASGFTFSDYYMTWVRQAPGKGLEWVAFIRNRAQGYTSDHNPSVKGRFTISRDNAKNSLYLQMNSLRAEDTAVYYCARDRPSYYVLDYWGQGTTVTVSS (SEQ ID NO: 5) |
| 2B5-0517 | DIQMTQSPSSLSASVGDRVTITCTSSQSLFNVRSGKNYLAWYQQKPGKAPKLLIYWASTRESGVPSRFSGSGSGTDFTLTISSLQPEDFATYYCKQSYDLFTFGGGTKVEIK (SEQ ID NO: 6) | EVQLVESGGGLVQPGGSLRLSCAASGFTFSDYYMTWVRQAPGKGLEWVAFIRNQARGYTSDHQPSVKGRFTISRDNAKNSLYLQMNSLRAEDTAVYYCARDRPSYYVLDYWGQGTTVTVSS (SEQ ID NO: 7) |
| 2B5-0522 | DIQMTQSPSSLSASVGDRVTITCTSSQSLFNVRSQKNYLAWYQQKPGKAPKLLIYWASDRESGVPSRFSGSGSGTDFTLTISSLQPEDFATYYCKQSYDLFTFGGGTKVEIK (SEQ ID NO: 8) | EVQLVESGGGLVQPGGSLRLSCAASGFTFSDYYMTWVRQAPGKGLEWVAFIRNQARGYTSDHQPSVKGRFTISRDNAKNSLYLQMNSLRAEDTAVYYCARDRPSYYVLDYWGQGTTVTVSS (SEQ ID NO: 7) |
| 2B5-0533 | DIQMTQSPSSLSASVGDRVTITCTSSQSLFNVRSGKNYLAWYQQKPGKAPKLLIYWASTRESGVPSRFSGSGSGTDFTLTISSLQPEDFATYYCKQSYDLFTFGGGTKVEIK (SEQ ID NO: 6) | EVQLVESGGGLVQPGGSLRLSCAASGFTFSDYYMTWVRQAPGKGLEWVAFIRNQARGYTSDHNPSVKGRFTISRDNAKNSLYLQMNSLRAEDTAVYYCARDRPSYYVLDYWGQGTTVTVSS (SEQ ID NO: 4) |
| 2B5-0538 | DIQMTQSPSSLSASVGDRVTITCTSSQSLFNVRSQKNYLAWYQQKPGKAPKLLIYWASDRESGVPSRFSGSGSGTDFTLTISSLQPEDFATYYCKQSYDLFTFGGGTKVEIK (SEQ ID NO: 8) | EVQLVESGGGLVQPGGSLRLSCAASGFTFSDYYMTWVRQAPGKGLEWVAFIRNQARGYTSDHNPSVKGRFTISRDNAKNSLYLQMNSLRAEDTAVYYCARDRPSYYVLDYWGQGTTVTVSS (SEQ ID NO: 4) |
| 2B5-0598 | DIQMTQSPSSLSASVGDRVTITCTSDQSLFNVRSGKNYLAWYQQKPGKAPKLLIYWASDRESGVPSRFSGSGSGTDFTLTISSLQPEDFATYYCKQSYDLFTFGGGTKVEIK (SEQ ID NO: 9) | EVQLVESGGGLVQPGGSLRLSCAASGFTFSDYYMTWVRQAPGKGLEWVAFIRNQDRGYTSDHQPSVKGRFTISRDNAKNSLYLQMNSLRAEDTAVYYCARDRPSYYVLDYWGQGTTVTVSS (SEQ ID NO: 10) |
| 2B5-0623 | DIQMTQSPSSLSASVGDRVTITCTSDQSLFNVRSGKNYLAWYQQKPGKAPKLLIYWASDRESGVPSRFSGSGSGTDFTLTISSLQPEDFATYYCKQSYDLFTFGGGTKVEIK (SEQ ID NO: 9) | EVQLVESGGGLVQPGGSLRLSCAASGFTFSDYYMTWVRQAPGKGLEWVAFIRNQARGYTSDHQPSVKGRFTISRDNAKNSLYLQMNSLRAEDTAVYYCARDRPSYYVLDYWGQGTTVTVSS (SEQ ID NO: 7) |
| 2B5-0707 | DIQMTQSPSSLSASVGDRVTITCTSSQSLFNVRSQKNYLAWYQQKPGKAPKLLIYWASTRESGVPSRFSGSGSGTDFTLTISSLQPEDFATYYCKQSYYLFTFGGGTKVEIK (SEQ ID NO: 11) | EVQLVESGGGLVQPGGSLRLSCAASGFTFSDYYMTWVRQAPGKGLEWVAFIRNQARGYTSDHNPSVKGRFTISRDNAKNSLYLQMNSLRAEDTAVYYCARDRHSYYVLDYWGQGTTVTVSS (SEQ ID NO: 12) |

TABLE 1-continued

| Variant | Light Chain | Heavy Chain |
|---|---|---|
| 2B5-0003 | DIQMTQSPSSLSASVGDRVTITCTSS QSLFNVRSRKNYLAWYQQKPGKAP KLLIYWASTRESGVPSRFSGSGSGT DFTLTISSLQPEDFATYYCKQSYDLF TFGGGTKVEIK (SEQ ID NO: 34) | EVQLVESGGGLVQPGGSLRLSC AASGFTFSDYYMTWVRQAPGKG LEWVAFIRNQARGYTSDHNPSVK GRFTISRDNAKNSLYLQMNSLRA EDTAVYYCARDRPSYYVLDYWG QGTTVTVSS (SEQ ID NO: 35) |
| H2B4 | DIVMTQSPDSLAVSLGERATINCKSS QSLFNVRSRKNYLAWYQQKPGQPP KLLISWASTRESGVPDRFSGSGSGT DFTLTISSLQAEDVAVYYCKQSYDLF TFGSGTKLEIK (SEQ ID NO: 85) | EVQLVESGGGLVQPGGSLRLSC AASGFTFSDYYMTWVRQAPGKG LEWVAFIRNRARGYTSDHNPSVK GRFTISRDNAKNSLYLQMNSLRA EDTAVYYCARDRPSYYVLDYWG QGTTVTVSS (SEQ ID NO: 2) |
| 2B5-1038 | DIQMTQSPSSLSASVGDRVTITCTSD QSLFNVRSGKNYLAWYQQKPGKAP KLLIYWASDRESGVPSRFSGSGSGT DFTLTISSLQPEDFATYYCKQSYDLF TFGGGTKVEIK (SEQ ID NO: 9) | EVQLVESGGGLVQPGGSLRLSC AASGFTFSDYYMTWVRQAPGKG LEWVAFIRNQARGYTSDHNPSVK GRFTISRDNAKNSLYLQMNSLRA EDTAVYYCARDRPSYYVLDYWG QGTTVTVSS (SEQ ID NO: 4) |
| 2B5-1039 | DIQMTQSPSSLSASVGDRVTITCTSS ESLFNVRSGKNYLAWYQQKPGKAP KLLIYWASDRESGVPSRFSGSGSGT DFTLTISSLQPEDFATYYCKQSYDLF TFGGGTKVEIK (SEQ ID NO: 87) | EVQLVESGGGLVQPGGSLRLSC AASGFTFSDYYMTWVRQAPGKG LEWVAFIRNQARGYTSDHNPSVK GRFTISRDNAKNSLYLQMNSLRA EDTAVYYCARDRPSYYVLDYWG QGTTVTVSS (SEQ ID NO: 4) |
| 2B5-1040 | DIQMTQSPSSLSASVGDRVTITCTSS QSLFNVRSGKNYLAWYQQKPGKAP KLLIYWASDRESGVPSRFSGSGSGT DFTLTISSLQPEDFATYYCKQSYDLF TFGGGTKVEIK (SEQ ID NO: 89) | EVQLVESGGGLVQPGGSLRLSC AASGFTFSDYYMTWVRQAPGKG LEWVAFIRNQARGYTSDHNPSVK GRFTISRDNAKNSLYLQMNSLRA EDTAVYYCARDRPSYYVLDYWG QGTTVTVSS (SEQ ID NO: 4) |

In Table 1, the underlined sequences are CDR sequences according to Kabat and in bold according to Chothia.

The invention provides CDR portions of antibodies to CD3 (including Chothia, Kabat CDRs, and CDR contact regions). Methods and techniques for identifying CDRs within VH and VL amino acid sequences are well known in the art and can be used to identify CDRs within the specified VH and/or VL amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et ai, J. Mol. Biol. 273:927-948 (1997); and Martin et ai, Proc. Natl. Acad. Sci. USA 86:9268-9272 (1989). Public databases are also available for identifying CDR sequences within an antibody. It is understood that in some embodiments, CDRs can be a combination of the Kabat and Chothia CDR (also termed "combined CRs" or "extended CDRs"). In some embodiments, the CDRs are the Kabat CDRs. In some further embodiments, the CDRs are the Chothia CDRs. In other words, in embodiments with more than one CDR, the CDRs may be any of Kabat, Chothia, combination CDRs, or combinations thereof. Tables 2 and 3 provide examples of CDR sequences provided herein.

In one embodiment, the present invention provides antibodies comprising an amino acid sequence that is listed in Table 1, or a substantially similar sequence thereof having at least 90%, at least 95%, at least 98% or at least 99% sequence identity thereto.

In some such embodiments, the present invention provides antibodies comprising a VL region comprising an amino acid sequence of any of the VL regions amino acid sequences listed in Table 1, or a substantially similar sequence thereof having at least 90%, at least 95%, at least 98% or at least 99% sequence identity thereto.

In some another such embodiments, the present invention provides antibodies comprising a VH region comprising an amino acid sequence of any of the VH regions amino acid sequences listed in Table 1, or a substantially similar sequence thereof having at least 90%, at least 95%, at least 98% or at least 99% sequence identity thereto.

In one embodiment, provided is an antibody which specifically binds to CD3, wherein the antibody comprises: (a) a heavy chain variable (VH) region comprising a VH complementarity determining region one (VH CDR1), a VH complementarity determining region two (VH CDR2), and a VH complementarity determining region three (VH CDR3) of the VH sequence shown in SEQ ID NO: 2, 4, 5, 7, 10, 12 or 35; and/or (b) a light chain variable (VL) region comprising a VL complementarity determining region one (VL CDR1), a VL complementarity determining region two (VL CDR2), and a VL complementarity determining region three (VL CDR3) of the VL sequence shown in SEQ ID NO: 1, 3, 6, 8, 9, 11, 34, 87 or 89.

In one embodiment, the present invention provides antibodies comprising a set of six CDRs (i.e., VL CDR1, VL CDR2, VL CDR3, VH CDR1, VH CDR2, VH CDR3) contained within a VLNH amino acid sequence pair as defined by any of the exemplary CD3 antibodies listed in Table 1.

In specific embodiments, the present invention provides antibodies comprising the VL CDR1, VL CDR2, VL CDR3, VH CDR1, VH CDR2, or VH CDR3 amino acid sequences set contained within a VLNH amino acid sequence pair selected from the group consisting of SEQ ID NOs: 1 and 2 (e.g., 2B5-0001 (2B5)); SEQ ID NOs: 3 and 2 (2B5-0002); SEQ ID NOs: 3 and 4 (e.g., 2B5-0006 (2135v6)); SEQ ID NOs: 3 and 5 (e.g., 2B5-0009); SEQ ID NOs: 6 and 7 (e.g., 2B5-0517); SEQ ID NOs: 8 and 7 (e.g., 2B5-0522); SEQ ID NOs: 6 and 4 (e.g., 2B5-0533); SEQ ID NOs: 8 and 4 (e.g., 2B5-0538); SEQ ID NOs: 9 and 10 (e.g., 2B5-0598); SEQ ID NOs: 9 and 7 (e.g., 2B5-0623); SEQ ID NOs: 11 and 12 (e.g., 2B5-0707); SEQ ID NOs: 34 and 35 (e.g., 2B5-0003); SEQ ID NOs: 85 and 2 (e.g., H2134), SEQ ID NOs: 9 and 4 (e.g., 2B5-1038) SEQ ID NOs: 87 and 4 (e.g., 2B5-1039); and SEQ ID NOs: 89 and 4 (e.g., 2B5-1040).

Table 2 sets forth VH CDR1, VH CDR2 and VH CDR3 regions of the exemplary CD3 antibodies.

TABLE 2

| mAb | VH CDR1 | VH CDR2 | VH CDR3 |
|---|---|---|---|
| Heavy Chain Variable Region | | | |
| 2B5-0001 (2B5) | DYYMT (SEQ ID NO: 13) (Kabat) GFTFSDY (SEQ ID NO: 14) (Chothia) GFTFSDYYMT (SEQ ID NO: 15) (extended) | FIRNRARGYTSDHNPSVKG (SEQ ID NO: 16) (Kabat) RNRARGYT (SEQ ID NO: 17) (Chothia) | DRPSYYVLDY (SEQ ID NO: 18) |
| 2B5-0002 | DYYMT ID NO: 13) (Kabat) GFTFSDY (SEQ ID NO: 14) (Chothia) GFTFSDYYMT (SEQ ID NO: 15) | FIRNRARGYTSDHNPSVKG (SEQ ID NO: 16) (Kabat) RNRARGYT (SEQ ID NO: 17) (Chothia) | DRPSYYVLDY (SEQ ID NO: 18) |
| 2B5-0006 (2B5v6) | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia), | DRPSYYVLDY (SEQ ID NO: 18) |
| 2B5-0009 | DYYMT (SEQ ID NO: 13) (Kabat) GFTFSDY (SEQ ID NO: 14) (Chothia) GFTFSDYYMT (SEQ ID NO: 15) (extended) | FIRNRAQGYTSDHNPSVKG (SEQ ID NO: 21) (Kabat) RNRAQGYT (SEQ ID NO: 22) (Chothia) | DRPSYYVLDY (SEQ ID NO: 18) |
| 2B5-0517 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHQPSVKG (SEQ ID NO: 23) (Kabat) RNQARGYT (SEQ ID NO: 20) (Chothia) | DRPSYYVLDY (SEQ ID NO: 18) |
| 2B5-0522 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHQPSVKG (SEQ ID NO: 23) (Kabat) RNQARGYT (SEQ ID NO: 20) (Chothia) | DRPSYYVLDY (SEQ ID NO: 18) |
| 2B5-0533 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |

TABLE 2-continued

| Heavy Chain Variable Region | | | |
|---|---|---|---|
| mAb | VH CDR1 | VH CDR2 | VH CDR3 |
| 2B5-0538 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |
| 2B5-0598 | DYYMT (SEQ ID NO: 13) (Kabat) GFTFSDY (SEQ ID NO: 14) (Chothia) GFTFSDYYMT (SEQ ID NO: 15) (extended) | FIRNQDRGYTSDHQPSVKG (SEQ ID NO: 24) (Kabat) RNQARGYT (SEQ ID NO: 20) (Chothia) | DRPSYYVLDY (SEQ ID NO: 18) |
| 2B5-0623 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHQPSVKG (SEQ ID NO: 23) (Kabat) RNQARGYT (SEQ ID NO: 20) (Chothia) | DRPSYYVLDY (SEQ ID NO: 18) |
| 2B5-0707 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRHSYYVLDY (SEQ ID NO: 25) |
| 2B5-0003 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |
| H2B4 | DYYMT (SEQ ID NO: 13) (Kabat) GFTFSDY (SEQ ID NO: 14) (Chothia) GFTFSDYYMT (SEQ ID NO: 15) (extended) | FIRNRARGYTSDHNPSVKG (SEQ ID NO: 16) (Kabat) RNRARGYT (SEQ ID NO: 17) (Chothia) | DRPSYYVLDY (SEQ ID NO: 18) |
| 2B5-1038 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |
| 2B5-1039 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |

TABLE 2-continued

Heavy Chain Variable Region

| mAb | VH CDR1 | VH CDR2 | VH CDR3 |
|---|---|---|---|
| 2B5-1040 | DYYMT (SEQ ID NO: 13) (Kabat) GFTFSDY (SEQ ID NO: 14) (Chothia) GFTFSDYYMT (SEQ ID NO: 15) (extended) | FIRNQARGYTSDHNPSVKG (SEQ ID NO: 19) (Kabat) RNQARGYT (SEQ ID NO: 20) (Chothia) | DRPSYYVLDY (SEQ ID NO: 18) |

In one embodiment, the present invention provides antibodies comprising a VH CDR1 comprising an amino acid sequence of any of the VH CDR1 amino acid sequences listed in Table 2 or a substantially similar sequence thereof having at least 90%, at least 95%, at least 98% or at least 99% sequence identity.

In another embodiment, the present invention provides antibodies comprising a VH CDR2 comprising an amino acid sequence of any of the VH CDR2 amino acid sequences listed in Table 2 or a substantially similar sequence thereof having at least 90%, at least 95%, at least 98% or at least 99% sequence identity.

In yet another embodiment, the present invention provides antibodies, comprising a VH CDR3 comprising an amino acid sequence of any of the VH CDR3 amino acid sequences listed in Table 2 or a substantially similar sequence thereof having at least 90%, at least 95%, at least 98% or at least 99% sequence identity.

Table 3 sets forth VL CDR1, VL CDR2 and VL CDR3 of the exemplary CD3 antibodies.

TABLE 3

Light Chain Variable Region

| mAb | CDR 1 | CDR 2 | CDR 3 |
|---|---|---|---|
| 2B5-0001 (2B5) | TSSQSLFNVRSRKNYLA (SEQ ID NO: 26) | WASTRES (SEQ ID NO: 27) | KQSYDLFT (SEQ ID NO: 28) |
| 2B5-0002 | TSSQSLFNVRSQKNYLA (SEQ ID NO: 29) | WASTRES (SEQ ID NO: 27) | KQSYDLFT (SEQ ID NO: 28) |
| 2B5-0006 (2B5v6) | TSSQSLFNVRSQKNYLA (SEQ ID NO: 29) | WASTRES (SEQ ID NO: 27) | KQSYDLFT (SEQ ID NO: 28) |
| 2B5-0009 | TSSQSLFNVRSQKNYLA (SEQ ID NO: 29) | WASTRES (SEQ ID NO: 27) | KQSYDLFT (SEQ ID NO: 28) |
| 2B5-0517 | TSSQSLFNVRSGKNYLA (SEQ ID NO: 30) | WASTRES (SEQ ID NO: 27) | KQSYDLFT (SEQ ID NO: 28) |
| 2B5-0522 | TSSQSLFNVRSQKNYLA (SEQ ID NO: 29) | WASDRES (SEQ ID NO: 31) | KQSYDLFT (SEQ ID NO: 28) |
| 2B5-0533 | TSSQSLFNVRSGKNYLA (SEQ ID NO: 30) | WASTRES (SEQ ID NO: 27) | KQSYDLFT (SEQ ID NO: 28) |
| 2B5-0538 | TSSQSLFNVRSQKNYLA (SEQ ID NO: 29) | WASDRES (SEQ ID NO: 31) | KQSYDLFT (SEQ ID NO: 28) |
| 2B5-0598 | TSDQSLFNVRSGKNYLA (SEQ ID NO: 32) | WASDRES (SEQ ID NO: 31) | KQSYDLFT (SEQ ID NO: 28) |
| 2B5-0623 | TSDQSLFNVRSGKNYLA (SEQ ID NO: 32) | WASDRES (SEQ ID NO: 31) | KQSYDLFT (SEQ ID NO: 28) |
| 2B5-0707 | TSSQSLFNVRSQKNYLA (SEQ ID NO: 29) | WASTRES (SEQ ID NO: 27) | KQSYYLFT (SEQ ID NO: 33) |
| 2B5-0003 | TSSQSLFNVRSRKNYLA (SEQ ID NO: 26) | WASTRES (SEQ ID NO: 27) | KQSYDLFT (SEQ ID NO: 28) |
| H2B4 | TSSQSLFNVRSRKNYLA (SEQ ID NO: 26) | WASTRES (SEQ ID NO: 27) | KQSYDLFT (SEQ ID NO: 28) |
| 2B5-1038 | TSDQSLFNVRSGKNYLA (SEQ ID NO: 32) | WASDRES (SEQ ID NO: 31) | KQSYDLFT (SEQ ID NO: 28) |

TABLE 3-continued

Light Chain Variable Region

| mAb | CDR 1 | CDR 2 | CDR 3 |
|---|---|---|---|
| 2B5-1039 | TSSESLFNVRSGKNYLA (SEQ ID NO: 91) | WASDRES (SEQ ID NO: 31) | KQSYDLFT (SEQ ID NO: 28) |
| 2B5-1040 | TSSQSLFNVRSGKNYLA (SEQ ID NO: 92) | WASDRES (SEQ ID NO: 31) | KQSYDLFT (SEQ ID NO: 28) |

In one embodiment, the present invention provides antibodies comprising a VL CDR1 comprising an amino acid sequence of any of the VL CDR1 amino acid sequences listed in Table 3 or a substantially similar sequence thereof having at least 90%, at least 95%, at least 98% or at least 99% sequence identity.

In another embodiment, the present invention provides antibodies comprising a VL CDR2 comprising an amino acid sequence of any of the VL CDR2 amino acid sequences listed in Table 3 or a substantially similar sequence thereof having at least 90%, at least 95%, at least 98% or at least 99% sequence identity.

In yet another embodiment, the present invention provides antibodies comprising a VL CDR3 comprising an amino acid sequence of any of the VL CDR3 amino acid sequences listed in Table 3 or a substantially similar sequence thereof having at least 90%, at least 95%, at least 98% or at least 99% sequence identity.

In some embodiments, provided is an antibody which specifically binds to CD3, wherein the antibody comprises: (a) a heavy chain (HC) variable (VH) region comprising a VH complementarity determining region one (CDR1), a VH complementary determining region two (VH CDR2) and a VH complementary determining region three (VH CDR3) of the VH having an amino acid sequence selected from the group consisting of SEQ ID NO: 2, 4, 5, 7, 10, 12 and 35; and/or (b) a light chain (LC) variable (VL) region comprising a VL complementary determining region one (VL CDR1), a VL complementary determining region two (VL CDR2), and a VL complementary determining region three (VL CDR3) of the VL having an amino acid sequence selected from the group consisting of SEQ ID NO: 1, 3, 6, 8, 9, 11, 34, 87 and 89.

In specific embodiments, the antibody comprises: (a) a VH region comprising (i) a VH CDR1 comprising a sequence of SEQ ID NO: 13, 14, or 15; (ii) a VH CDR2 comprising a sequence of SEQ ID NO: 16, 17, 19, 20, 21, 22, 23 or 24; and (iii) a VH CDR3 comprising a sequence of SEQ ID NO: 18 or 25; and/or (b) a VL region comprising (i) a VL CDR1 comprising a sequence of SEQ ID NO: 26, 29, 30, 32, 91 or 92; (ii) a VL CDR2 comprising a sequence of SEQ ID NO: 27 or 31; and (iii) a VL CDR3 comprising a sequence of SEQ ID NO: 28 or 33.

In certain embodiments, the present invention provides an antibody that binds to CD3 and competes with the antibody as described herein, including 2B5-0001 (2B5), 2B5-0002, 2B5-0006 (265v6), 2B5-0009, 2B5-0517, 2B5-0522, 2B5-0533, 2B5-0538, 2B5-0598, 2B5-0623, 2B5-0707, 2B5-0003, 2B5-1038, 2B5-1039, and 2B5-1040.

In some embodiments, the invention also provides CDR portions of CD3 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

Certain of the CD3 antibodies provided herein may be referred to by more than one name. For example, 2B5-0001 may be referred to as 2B5 or h2B5; and 2B5-0006 may be referred to as 2B5v6 or h2B5v6. Table 4 shows the format of the antibody and the CD3 antibody region present in the antibodies as disclosed herein.

TABLE 4

| Sequence | Description | Format | CD3 Antibody Region |
|---|---|---|---|
| 2B5-0001 (2B5) | CD3 antibody | IgG | 2B5-0001 |
| 2B5-0002 | CD3 antibody | IgG | 2B5-0002 |
| 2B5-0003 | CD3 antibody | IgG | 2B5-0003 |
| 2B5-0006 (2B5v6) | CD3 antibody | IgG | 2B5-0006 |
| 2B5-0009 | CD3 antibody | IgG | 2B5-0009 |
| 2B5-0517 | CD3 antibody | IgG | 2B5-0517 |
| 2B5-0522 | CD3 antibody | IgG | 2B5-0522 |
| 2B5-0533 | CD3 antibody | IgG | 2B5-0533 |
| 2B5-0538 | CD3 antibody | IgG | 2B5-0538 |
| 2B5-0598 | CD3 antibody | IgG | 2B5-0598 |
| 2B5-0623 | CD3 antibody | IgG | 2B5-0623 |
| 2B5-0707 | CD3 antibody | IgG | 2B5-0707 |
| 2B5-1038 | CD3 antibody | IgG | 2B5-1038 |
| 2B5-1039 | CD3 antibody | IgG | 2B5-1039 |
| 2B5-1040 | CD3 antibody | IgG | 2B5-1040 |
| H2B4 | CD3 antibody | IgG | H2B4 |
| GUCY2C-H2B4 | CD3-GUCY2c bispecific antibody | CD3 bispecific | H2B4 |
| GUCY2C-2B5 | CD3-GUCY2c bispecific antibody | CD3 bispecific | 2B5-0001 |
| GUCY2C-2B5v6 | CD3-GUCY2c bispecific antibody | CD3 bispecific | 2B5-0006 |
| xFLT3-2B5v6 | CD3-FLT3 bispecific antibody | CD3 bispecific | 2B5-0006 |

The binding affinity ($K_D$) of the antibodies as described herein to CD3 (such as human CD3 epsilon (e.g., SEQ ID NO: 40), can be about 0.001 nM to about 6500 nM. In some embodiments, the binding affinity is about any of 6500 nM, 6000 nM, 5500 nM, 4500 nM, 4000 nM, 3500 nM, 3000 nM, 2500 nM, 2000 nM, 1500 nM, 1000 nM, 750 nM, 500 nM, 400 nM, 300 nM, 250 nM, 200 nM, 150 nM, 100 nM, 75 nM, 50 nM, 45 nM, 40 nM, 35 nM, 30 nM, 25 nM, 20 nM, 19 nM, 17 nM, 16 nM, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, 0.002 nM, or 0.001 nM. In some embodiments, the binding affinity is less than about any of 6500 nM, 6000 nM, 5500 nM, 5000 nM, 4000 nM, 3000 nM, 2000 nM, 1000 nM, 900 nM, 800 nM, 500 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, 0.5 nM, 0.1 nM, 0.05 nM, 0.01 nM or lower nM. In a certain embodiment, the antibody has a $K_D$ of about 80 to about 200 µM. In a particular embodiment, the antibody has a $K_D$ of about 10 nm to 2000 nm.

In one aspect, the invention provides an antibody, or a pharmaceutical composition for use in a method of modulating a T cell mediated immune response in a subject in need thereof. In specific embodiments, the invention provides an antibody, or a pharmaceutical composition for use in a method of inhibiting growth of tumor cells in a subject.

In another aspect, the invention provides an antibody, or a pharmaceutical composition for use in treating cancer, optionally wherein the cancer is selected from the group consisting of breast, ovarian, thyroid, prostate, cervical, lung, bladder, endometrial, head and neck, testicular, glioblastoma cancer and cancer of digestive system.

In yet another aspect, the invention provides an antibody, or a pharmaceutical composition for use in treating cancer wherein the T cell mediated immune response is modulated or wherein the growth of tumor cells is inhibited.

The present invention also provides nucleic acid molecules encoding CD3 antibodies or portions thereof. For example, the present invention provides nucleic acid molecules encoding any of the VH or VL amino acid sequences listed in Table 1, or a substantially similar sequence thereof having at least 90%, at least 95%, at least 98% or at least 99% sequence identity thereto.

The present invention also provides nucleic acid molecules encoding any of the VH CDR1, VH CDR2 or VH CDR3 amino acid sequences listed in Table 2, or a substantially similar sequence thereof having at least 90%, at least 95%, at least 98% or at least 99% sequence identity thereto.

The present invention also provides nucleic acid molecules encoding any of the VL CDR1, VL CDR2 or VL CDR3 amino acid sequences listed in Table 3, or a substantially similar sequence thereof having at least 90%, at least 95%, at least 98% or at least 99% sequence identity thereto.

The present invention also provides nucleic acid molecules encoding a HC VR, wherein the VH comprises a set of three CDRs (i.e., VH CDR1, VH CDR2 or VH CDR3), wherein the VH CDR1, VH CDR2 and VH CDR3 amino acid sequence set is as defined by any of the exemplary CD3 antibodies listed in Table 2.

The present invention also provides nucleic acid molecules encoding a LC VR, wherein the VL comprises a set of three CDRs (i.e., VL CDR1, VL CDR2 or VL CDR3), wherein the VL CDR1, VL CDR2 and VL CDR3 amino acid sequence set is as defined by any of the exemplary CD3 antibodies listed in Table 3.

The present invention also provides nucleic acid molecules encoding both a VH and a VL, wherein the VH comprises an amino acid sequence of any of the VH amino acid sequences listed in Table 1, and wherein the VL comprises an amino acid sequence of any of the VL amino acid sequences listed in Table 1.

The present invention also provides recombinant expression vectors capable of expressing a polypeptide comprising a heavy or light chain variable region of a CD3 antibody. For example, the present invention includes recombinant expression vectors comprising any of the nucleic acid molecules mentioned above, i.e., nucleic acid molecules encoding any of the VH and VL set forth in Table 1, and/or CDR sequences as set forth in Tables 2 or 3. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In certain embodiments, a polynucleotide comprises a sequence encoding the heavy chain and/or the light chain variable regions of antibody 2B5-0001 (2B5), 2B5-0002, 2B5-0006 (2B5v6), 2B5-0009, 2B5-0517, 2B5-0522, 2B5-0533, 2B5-0538, 2B5-0598, 2B5-0623, 2B5-0707, 2B5-0003, 2B5-1038, 2B5-1039, or 2B5-1040, as listed in Table 4.

The sequence encoding the antibody of interest may be maintained in a vector in a host cell and the host cell can then be expanded and frozen for future use. Vectors (including expression vectors) and host cells are further described herein.

Polynucleotides complementary to any such sequences are also encompassed by the present invention. In one aspect, the invention provides a method of making any of the polynucleotides described herein. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein CD3 or a CD3 domain (e.g., domains 1-4) is effected by an immunoassay or FACS. A cell overexpressing the antibody or protein of interest can be identified.

The invention also encompasses scFv of antibodies of this invention. Single chain variable region fragments are made by linking light and/or heavy chain variable regions by using a short linking peptide (Bird et al., Science 242:423-426, 1988). An example of a linking peptide comprises the sequence of SEQ ID NO: 65. In one embodiment, the linking peptide bridges approximately 3.5 nm between the carboxy terminus of one variable region and the amino terminus of the other variable region. Linkers of other sequences have been designed and used (Bird et al., Science 242:423-426, 1988). Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In one aspect, provided is a polynucleotide sequence encoding any one of partial light chain sequence and/or any one of partial heavy chain sequence disclosed herein. Exemplary CD3 polynucleotides encoding the VH regions and VL regions of the antibodies of the present invention are listed in Table 5.

TABLE 5

| Variant | Light Chain | Heavy Chain |
|---|---|---|
| 2B5-0001 (2B5) | GACATCCAGATGACCCAGTC CCCCTCTTCTCTGTCTGCCTC TGTGGGCGACAGAGTGACCA TCACCTGCACAAGCTCACAG TCACTGTTTAATGTCCGCAGC CGGAAAAACTATCTTGCGTG GTATCAGCAGAAGCCTGGCA AGGCTCCCAAGCTGCTGATC TACTGGGCCAGTACACGAGA ATCCGGCGTGCCTTCCAGAT TCTCCGGCTCTGGCTCTGGC ACCGATTTCACCCTGACCATC TCCTCCCTCCAGCCTGAGGA TTTCGCCACCTACTACTGCAA ACAGTCTTACGACCTTTTCAC TTTTGGCGGCGGAACAAAGG TGGAGATCAAG (SEQ ID NO: 68) | GAAGTGCAGCTTGTTGAATCTG GCGGCGGTTTGGTTCAGCCCG GTGGATCACTGCGACTCAGTT GCGCAGCTAGCGGCTTCACCT TTTCTGATTACTACATGACATG GGTACGACAGGCGCCAGGCAA GGGTTTGGAATGGGTAGCATT CATACGCAATAGGGCACGCGG GTACACTTCAGACCACAATCCC TCAGTAAAAGGAAGATTTACCA TCTCAAGAGACAATGCCAAAAA TTCACTCTACCTGCAAATGAAC TCACTTCGCGCCGAGGATACC GCCGTGTATTACTGTGCCAGA GACAGACCATCTTATTACGTGC TGGACTATTGGGGACAGGGCA CTACAGTCACCGTCAGCTCT (SEQ ID NO: 69) |

TABLE 5-continued

| Variant | Light Chain | Heavy Chain |
| --- | --- | --- |
| 2B5-0002 | GACATCCAGATGACCCAGTC CCCCTCTTCTCTGTCTGCCTC TGTGGGCGACAGAGTGACCA TCACCTGCACAAGCTCACAG TCACTGTTTAATGTCCGCAGC CAGAAAAACTATCTTGCGTG GTATCAGCAGAAGCCTGGCA AGGCTCCCAAGCTGCTGATC TACTGGGCCAGTACACGAGA ATCCGGCGTGCCTTCCAGAT TCTCCGGCTCTGGCTCTGGC ACCGATTTCACCCTGACCATC TCCTCCCTCCAGCCTGAGGA TTTCGCCACCTACTACTGCAA ACAGTCTTACGACCTTTTCAC TTTTGGCGGCGGAACAAAGG TGGAGATCAAG (SEQ ID NO: 70) | GAAGTGCAGCTTGTTGAATCTG GCGGCGGTTTGGTTCAGCCCG GTGGATCACTGCGACTCAGTT GCGCAGCTAGCGGCTTCACCT TTTCTGATTACTACATGACATG GGTACGACAGGCGCCAGGCAA GGGTTTGGAATGGGTAGCATT CATACGCAATAGGGCACGCGG GTACACTTCAGACCACAATCCC TCAGTAAAAGGAAGATTTACCA TCTCAAGAGACAATGCCAAAAA TTCACTCTACCTGCAAATGAAC TCACTTCGCGCCGAGGATACC GCCGTGTATTACTGTGCCAGA GACAGACCATCTTATTACGTGC TGGACTATTGGGGACAGGGCA CTACAGTCACCGTCAGCTCT (SEQ ID NO: 69) |
| 2B5-0006 (2B5v6) | GACATCCAGATGACCCAGTC CCCCTCTTCTCTGTCTGCCTC TGTGGGCGACAGAGTGACCA TCACCTGCACAAGCTCACAG TCACTGTTTAATGTCCGCAGC CAGAAAAACTATCTTGCGTG GTATCAGCAGAAGCCTGGCA AGGCTCCCAAGCTGCTGATC TACTGGGCCAGTACACGAGA ATCCGGCGTGCCTTCCAGAT TCTCCGGCTCTGGCTCTGGC ACCGATTTCACCCTGACCATC TCCTCCCTCCAGCCTGAGGA TTTCGCCACCTACTACTGCAA ACAGTCTTACGACCTTTTCAC TTTTGGCGGCGGAACAAAGG TGGAGATCAAG (SEQ ID NO: 70) | GAAGTGCAGCTTGTTGAATCTG GCGGCGGTTTGGTTCAGCCCG GTGGATCACTGCGACTCAGTT GCGCAGCTAGCGGCTTCACCT TTTCTGATTACTACATGACATG GGTACGACAGGCGCCAGGCAA GGGTTTGGAATGGGTAGCATT CATACGCAATCAGGCACGCGG GTACACTTCAGACCACAATCCC TCAGTAAAAGGAAGATTTACCA TCTCAAGAGACAATGCCAAAAA TTCACTCTACCTGCAAATGAAC TCACTTCGCGCCGAGGATACC GCCGTGTATTACTGTGCCAGA GACAGACCATCTTATTACGTGC TGGACTATTGGGGACAGGGCA CTACAGTCACCGTCAGCTCT (SEQ ID NO: 71) |
| 2B5-0009 | GACATCCAGATGACCCAGTC CCCCTCTTCTCTGTCTGCCTC TGTGGGCGACAGAGTGACCA TCACCTGCACAAGCTCACAG TCACTGTTTAATGTCCGCAGC CAGAAAAACTATCTTGCGTG GTATCAGCAGAAGCCTGGCA AGGCTCCCAAGCTGCTGATC TACTGGGCCAGTACACGAGA ATCCGGCGTGCCTTCCAGAT TCTCCGGCTCTGGCTCTGGC ACCGATTTCACCCTGACCATC TCCTCCCTCCAGCCTGAGGA TTTCGCCACCTACTACTGCAA ACAGTCTTACGACCTTTTCAC TTTTGGCGGCGGAACAAAGG TGGAGATCAAG (SEQ ID NO: 70) | GAAGTGCAGCTTGTTGAATCTG GCGGCGGTTTGGTTCAGCCCG GTGGATCACTGCGACTCAGTT GCGCAGCTAGCGGCTTCACCT TTTCTGATTACTACATGACATG GGTACGACAGGCGCCAGGCAA GGGTTTGGAATGGGTAGCATT CATACGCAATAGGGCACAGGG GTACACTTCAGACCACAATCCC TCAGTAAAAGGAAGATTTACCA TCTCAAGAGACAATGCCAAAAA TTCACTCTACCTGCAAATGAAC TCACTTCGCGCCGAGGATACC GCCGTGTATTACTGTGCCAGA GACAGACCATCTTATTACGTGC TGGACTATTGGGGACAGGGCA CTACAGTCACCGTCAGCTCT (SEQ ID NO: 72) |
| 2B5-0517 | GACATCCAGATGACCCAGTC CCCCTCTTCTCTGTCTGCCTC TGTGGGCGACAGAGTGACCA TCACCTGCACAAGCTCACAG TCACTGTTTAATGTCCGCAGC GGAAAAAACTATCTTGCGTG GTATCAGCAGAAGCCTGGCA AGGCTCCCAAGCTGCTGATC TACTGGGCCAGTACACGAGA ATCCGGCGTGCCTTCCAGAT TCTCCGGCTCTGGCTCTGGC ACCGATTTCACCCTGACCATC TCCTCCCTCCAGCCTGAGGA TTTCGCCACCTACTACTGCAA ACAGTCTTACGACCTTTTCAC TTTTGGCGGCGGAACAAAGG TGGAGATCAAG (SEQ ID NO: 83) | GAAGTGCAGCTTGTTGAATCTG GCGGCGGTTTGGTTCAGCCCG GTGGATCACTGCGACTCAGTT GCGCAGCTAGCGGCTTCACCT TTTCTGATTACTACATGACATG GGTACGACAGGCGCCAGGCAA GGGTTTGGAATGGGTAGCATT CATACGCAATCAGGCACGCGG GTACACTTCAGACCACCAGCC CTCAGTAAAAGGAAGATTTACC ATCTCAAGAGACAATGCCAAAA ATTCACTCTACCTGCAAATGAA CTCACTTCGCGCCGAGGATAC CGCCGTGTATTACTGTGCCAG AGACAGACCATCTTATTACGTG CTGGACTATTGGGGACAGGGC ACTACAGTCACCGTCAGCTCT (SEQ ID NO: 73) |

TABLE 5-continued

| Variant | Light Chain | Heavy Chain |
| --- | --- | --- |
| 2B5-0522 | GACATCCAGATGACCCAGTC<br>CCCCTCTTCTCTGTCTGCCTC<br>TGTGGGCGACAGAGTGACCA<br>TCACCTGCACAAGCTCACAG<br>TCACTGTTTAATGTCCGCAGC<br>CAGAAAAACTATCTTGCGTG<br>GTATCAGCAGAAGCCTGGCA<br>AGGCTCCCAAGCTGCTGATC<br>TACTGGGCCAGTGATCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGGAACAAAGG<br>TGGAGATCAAG<br>(SEQ ID NO: 74) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACCAGCC<br>CTCAGTAAAAGGAAGATTTACC<br>ATCTCAAGAGACAATGCCAAAA<br>ATTCACTCTACCTGCAAATGAA<br>CTCACTTCGCGCCGAGGATAC<br>CGCCGTGTATTACTGTGCCAG<br>AGACAGACCATCTTATTACGTG<br>CTGGACTATTGGGGACAGGGC<br>ACTACAGTCACCGTCAGCTCT<br>(SEQ ID NO: 73) |
| 2B5-0533 | GACATCCAGATGACCCAGTC<br>CCCCTCTTCTCTGTCTGCCTC<br>TGTGGGCGACAGAGTGACCA<br>TCACCTGCACAAGCTCACAG<br>TCACTGTTTAATGTCCGCAGC<br>GGAAAAAACTATCTTGCGTG<br>GTATCAGCAGAAGCCTGGCA<br>AGGCTCCCAAGCTGCTGATC<br>TACTGGGCCAGTACACGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGGAACAAAGG<br>TGGAGATCAAG<br>(SEQ ID NO: 83) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACAATCCC<br>TCAGTAAAAGGAAGATTTACCA<br>TCTCAAGAGACAATGCCAAAA<br>TTCACTCTACCTGCAAATGAAC<br>TCACTTCGCGCCGAGGATACC<br>GCCGTGTATTACTGTGCCAGA<br>GACAGACCATCTTATTACGTGC<br>TGGACTATTGGGGACAGGGCA<br>CTACAGTCACCGTCAGCTCT<br>(SEQ ID NO: 71) |
| 2B5-0538 | GACATCCAGATGACCCAGTC<br>CCCCTCTTCTCTGTCTGCCTC<br>TGTGGGCGACAGAGTGACCA<br>TCACCTGCACAAGCTCACAG<br>TCACTGTTTAATGTCCGCAGC<br>CAGAAAAACTATCTTGCGTG<br>GTATCAGCAGAAGCCTGGCA<br>AGGCTCCCAAGCTGCTGATC<br>TACTGGGCCAGTGATCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGGAACAAAGG<br>TGGAGATCAAG<br>(SEQ ID NO: 74) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACAATCCC<br>TCAGTAAAAGGAAGATTTACCA<br>TCTCAAGAGACAATGCCAAAA<br>TTCACTCTACCTGCAAATGAAC<br>TCACTTCGCGCCGAGGATACC<br>GCCGTGTATTACTGTGCCAGA<br>GACAGACCATCTTATTACGTGC<br>TGGACTATTGGGGACAGGGCA<br>CTACAGTCACCGTCAGCTCT<br>(SEQ ID NO: 71) |
| 2B5-0598 | GACATCCAGATGACCCAGTC<br>CCCCTCTTCTCTGTCTGCCTC<br>TGTGGGCGACAGAGTGACCA<br>TCACCTGCACAAGCGACCAG<br>TCACTGTTTAATGTCCGCAGC<br>GGCAAAAACTATCTTGCGTG<br>GTATCAGCAGAAGCCTGGCA<br>AGGCTCCCAAGCTGCTGATC<br>TACTGGGCCAGTGACCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGGAACAAAGG<br>TGGAGATCaag<br>(SEQ ID NO: 75) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGACCGCGG<br>GTACACTTCAGACCACCAGCC<br>CTCAGTAAAAGGAAGATTTACC<br>ATCTCAAGAGACAATGCCAAAA<br>ATTCACTCTACCTGCAAATGAA<br>CTCACTTCGCGCCGAGGATAC<br>CGCCGTGTATTACTGTGCCAG<br>AGACAGACCATCTTATTACGTG<br>CTGGACTATTGGGGACAGGGC<br>ACTACAGTCACCGTCAGCtct<br>(SEQ ID NO: 76) |

TABLE 5-continued

| Variant | Light Chain | Heavy Chain |
|---|---|---|
| 2B5-0623 | GACATCCAGATGACCCAGTCCCCCTCTTCTCTGTCTGCCTCTGTGGGCGACAGAGTGACCATCACCTGCACAAGCGACCAGTCACTGTTTAATGTCCGCAGCGGCAAAAACTATCTTGCGTGGTATCAGCAGAAGCCTGGCAAGGCTCCCAAGCTGCTGATCTACTGGGCCAGTGACCGAGAATCCGGCGTGCCTTCCAGATTCTCCGGCTCTGGCTCTGGCACCGATTTCACCCTGACCATCTCCTCCCTCCAGCCTGAGGATTTCGCCACCTACTACTGCAAACAGTCTTACGACCTTTTCACTTTTGGCGGCGGAACAAAGGTGGAGATCaag (SEQ ID NO: 75) | GAAGTGCAGCTTGTTGAATCTGGCGGCGGTTTGGTTCAGCCCGGTGGATCACTGCGACTCAGTGCGCAGCTAGCGGCTTCACCTTTTCTGATTACTACATGACATGGGTACGACAGGCGCCAGGCAAGGGTTTGGAATGGGTAGCATTCATACGCAATCAGGCACGCGGGTACACTTCAGACCACCAGCCCTCAGTAAAAGGAAGATTTACCATCTCAAGAGACAATGCCAAAAATTCACTCTACCTGCAAATGAACTCACTTCGCGCCGAGGATACCGCCGTGTATTACTGTGCCAGAGACAGACCATCTTATTACGTGCTGGACTATTGGGGACAGGGCACTACAGTCACCGTCAGCTCT (SEQ ID NO: 73) |
| 2B5-0707 | GACATCCAGATGACCCAGTCCCCCTCTTCTCTGTCTGCCTCTGTGGGCGACAGAGTGACCATCACCTGCACAAGCTCACAGTCACTGTTTAATGTCCGCAGCCAGAAAAACTATCTTGCGTGGTATCAGCAGAAGCCTGGCAAGGCTCCCAAGCTGCTGATCTACTGGGCCAGTACACGAGAATCCGGCGTGCCTTCCAGATTCTCCGGCTCTGGCTCTGGCACCGATTTCACCCTGACCATCTCCTCCCTCCAGCCTGAGGATTTCGCCACCTACTACTGCAAACAGTCTTACTACCTTTTCACTTTTGGCGGCGGAACAAAGGTGGAGATCAAG (SEQ ID NO: 77) | GAAGTGCAGCTTGTTGAATCTGGCGGCGGTTTGGTTCAGCCCGGTGGATCACTGCGACTCAGTGCGCAGCTAGCGGCTTCACCTTTTCTGATTACTACATGACATGGGTACGACAGGCGCCAGGCAAGGGTTTGGAATGGGTAGCATTCATACGCAATCAGGCACGCGGGTACACTTCAGACCACAATCCCTCAGTAAAAGGAAGATTTACCATCTCAAGAGACAATGCCAAAATTCACTCTACCTGCAAATGAACTCACTTCGCGCCGAGGATACCGCCGTGTATTACTGTGCCAGAGACAGACACTCTTATTACGTGCTGGACTATTGGGGACAGGGCACTACAGTCACCGTCAGCTCT (SEQ ID NO: 84) |
| 2B5-0003 | GACATCCAGATGACCCAGTCCCCCTCTTCTCTGTCTGCCTCTGTGGGCGACAGAGTGACCATCACCTGCACAAGCTCACAGTCACTGTTTAATGTCCGCAGCCGGAAAAACTATCTTGCGTGGTATCAGCAGAAGCCTGGCAAGGCTCCCAAGCTGCTGATCTACTGGGCCAGTACACGAGAATCCGGCGTGCCTTCCAGATTCTCCGGCTCTGGCTCTGGCACCGATTTCACCCTGACCATCTCCTCCCTCCAGCCTGAGGATTTCGCCACCTACTACTGCAAACAGTCTTACGACCTTTTCACTTTTGGCGGCGGAACAAAGGTGGAGATCAAG (SEQ ID NO: 68) | GAAGTGCAGCTTGTTGAATCTGGCGGCGGTTTGGTTCAGCCCGGTGGATCACTGCGACTCAGTGCGCAGCTAGCGGCTTCACCTTTTCTGATTACTACATGACATGGGTACGACAGGCGCCAGGCAAGGGTTTGGAATGGGTAGCATTCATACGCAATCAGGCACGCGGGTACACTTCAGACCACAATCCCTCAGTAAAAGGAAGATTTACCATCTCAAGAGACAATGCCAAAAATTCACTCTACCTGCAAATGAACTCACTTCGCGCCGAGGATACCGCCGTGTATTACTGTGCCAGAGACAGACCATCTTATTACGTGCTGGACTATTGGGGACAGGGCACTACAGTCACCGTCAGCTCT (SEQ ID NO: 71) |
| H2B4 | GACATCGTGATGACCCAGAGCCCCGATAGCCTGGCCGTGTCTCTGGGAGAGAGAGCCACCATCAACTGCAAGAGCAGCCAGAGCCTGTTCAACGTGAGAAGCCGGAAGAACTACCTGGCCTGGTATCAGCAGAAACCCGGCCAGCCCCCCAAGCTGCTGATCAGCTGGGCCAGCACCAGAGAAAGCGGCGTGCCCGATAGATTCAGCGGCAGCGGAAGCGGCACCGACTTCACCCTGACAATCAGCTCCCTGCAGGCCGAGGACGTGGCCGTGTACTACTGCAAGCAGAGCTACGACCTGTTCACCTTCGGCAGCGGCACCAAGCTGGAAATCAAA (SEQ ID NO: 86) | GAAGTGCAGCTTGTTGAATCTGGCGGCGGTTTGGTTCAGCCCGGTGGATCACTGCGACTCAGTGCGCAGCTAGCGGCTTCACCTTTTCTGATTACTACATGACATGGGTACGACAGGCGCCAGGCAAGGGTTTGGAATGGGTAGCATTCATACGCAATAGGGCACGCGGGTACACTTCAGACCACAATCCCTCAGTAAAAGGAAGATTTACCATCTCAAGAGACAATGCCAAAAATTCACTCTACCTGCAAATGAACTCACTTCGCGCCGAGGATACCGCCGTGTATTACTGTGCCAGAGACAGACCATCTTATTACGTGCTGGACTATTGGGGACAGGGCACTACAGTCACCGTCAGCTCT (SEQ ID NO: 69) |

TABLE 5-continued

| Variant | Light Chain | Heavy Chain |
| --- | --- | --- |
| 2B5-1038 | GACATCCAGATGACCCAGTC<br>CCCCTCTTCTCTGTCTGCCTC<br>TGTGGGCGACAGAGTGACCA<br>TCACCTGCACAAGCGACCAG<br>TCACTGTTTAATGTCCGCAGC<br>GGCAAAAACTATCTTGCGTG<br>GTATCAGCAGAAGCCTGGCA<br>AGGCTCCCAAGCTGCTGATC<br>TACTGGGCCAGTGACCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGAACAAAGG<br>TGGAGATCaag<br>(SEQ ID NO: 75) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACAATCCC<br>TCAGTAAAAGGAAGATTTACCA<br>TCTCAAGAGACAATGCCAAAAA<br>TTCACTCTACCTGCAAATGAAC<br>TCACTTCGCGCCGAGGATACC<br>GCCGTGTATTACTGTGCCAGA<br>GACAGACCATCTTATTACGTGC<br>TGGACTATTGGGGACAGGGCA<br>CTACAGTCACCGTCAGCTCT<br>(SEQ ID NO: 71) |
| 2B5-1039 | GACATCCAGATGACCCAGTC<br>CCCCTCTTCTCTGTCTGCCTC<br>TGTGGGCGACAGAGTGACCA<br>TCACCTGCACAAGCTCAGAG<br>TCACTGTTTAATGTCCGCAGC<br>GGCAAAAACTATCTTGCGTG<br>GTATCAGCAGAAGCCTGGCA<br>AGGCTCCCAAGCTGCTGATC<br>TACTGGGCCAGTGACCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGAACAAAGG<br>TGGAGATCAAG<br>(SEQ ID NO: 88) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACAATCCC<br>TCAGTAAAAGGAAGATTTACCA<br>TCTCAAGAGACAATGCCAAAAA<br>TTCACTCTACCTGCAAATGAAC<br>TCACTTCGCGCCGAGGATACC<br>GCCGTGTATTACTGTGCCAGA<br>GACAGACCATCTTATTACGTGC<br>TGGACTATTGGGGACAGGGCA<br>CTACAGTCACCGTCAGCTCT<br>(SEQ ID NO: 71) |
| 2B5-1040 | GACATCCAGATGACCCAGTC<br>CCCCTCTTCTCTGTCTGCCTC<br>TGTGGGCGACAGAGTGACCA<br>TCACCTGCACAAGCTCACAG<br>TCACTGTTTAATGTCCGCAGC<br>GGCAAAAACTATCTTGCGTG<br>GTATCAGCAGAAGCCTGGCA<br>AGGCTCCCAAGCTGCTGATC<br>TACTGGGCCAGTGACCGAGA<br>ATCCGGCGTGCCTTCCAGAT<br>TCTCCGGCTCTGGCTCTGGC<br>ACCGATTTCACCCTGACCATC<br>TCCTCCCTCCAGCCTGAGGA<br>TTTCGCCACCTACTACTGCAA<br>ACAGTCTTACGACCTTTTCAC<br>TTTTGGCGGCGAACAAAGG<br>TGGAGATCAAG<br>(SEQ ID NO: 90) | GAAGTGCAGCTTGTTGAATCTG<br>GCGGCGGTTTGGTTCAGCCCG<br>GTGGATCACTGCGACTCAGTT<br>GCGCAGCTAGCGGCTTCACCT<br>TTTCTGATTACTACATGACATG<br>GGTACGACAGGCGCCAGGCAA<br>GGGTTTGGAATGGGTAGCATT<br>CATACGCAATCAGGCACGCGG<br>GTACACTTCAGACCACAATCCC<br>TCAGTAAAAGGAAGATTTACCA<br>TCTCAAGAGACAATGCCAAAAA<br>TTCACTCTACCTGCAAATGAAC<br>TCACTTCGCGCCGAGGATACC<br>GCCGTGTATTACTGTGCCAGA<br>GACAGACCATCTTATTACGTGC<br>TGGACTATTGGGGACAGGGCA<br>CTACAGTCACCGTCAGCTCT<br>(SEQ ID NO: 71) |

In one aspect, the invention provides compositions (such as a pharmaceutical composition) comprising any of the polynucleotides of the invention. In some embodiments, the composition may comprise any of one the polynucleotides shown in Table 5. In specific embodiments, the composition comprises an expression vector comprising a polynucleotide encoding any of the antibodies described herein, e.g., any of one polynucleotides shown in Table 5.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include mature and immature mRNAs, such as precursor mRNAs (pre-mRNA) or heterogeneous nuclear mRNAs (hnRNA) and mature mRNAs. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In one aspect, the invention provides a method of making any of the polynucleotides described herein. For example, the polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art (e.g., Sambrook et al., 1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody, or protein CD3, or a CD3 domain (e.g., domains 1-4) is effected by an immunoassay or FACS. A cell overexpressing the antibody or protein of interest can be identified.

In one aspect, a CD3 antibody molecule will have an affinity for CD3, e.g., as measured by direct binding or competition binding assays in the picomolar to micromolar affinity range, preferably in the picomolar to low nanomolar range.

Bispecific antibodies can be prepared using the sequences disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983).

In another embodiment, the antibody as described herein, comprises a full-length human antibody, wherein an antibody variable region of the heterodimeric protein is capable of recruiting the activity of a human immune effector cell by specifically binding to an effector antigen (e.g., CD3 antigen) located on the human immune effector cell, and wherein a second antibody variable region of the heterodimeric protein is capable of specifically binding to a target antigen. In some embodiments, the human antibody has an IgG1, IgG2, IgG3, or IgG4 isotype. In some embodiments, the heterodimeric protein comprises an immunologically inert Fc chain.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric antibody or a bispecific antibody) include, but are not limited to, human CD3, CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a *plasmodium*, or a bacterium). In a foreign target cell, the cell is an invading pathogen, such as a bacterium, a *plasmodium*, or a virus.

In some embodiments, the antibody useful in the present invention is a Fab, a Fab fragment, a F(ab)$_2$ fragment, an Fv fragment, a single chain Fv fragment, a disulfide stabilized Fv fragment, a single-chain antibody, a monoclonal antibody, a chimeric antibody, a bispecific antibody, a trispecific antibody, a multispecific antibody, a bispecific so heterodimeric diabody, a bispecific heterodimeric IgG, a polyclonal antibody, a labeled antibody, a humanized antibody, a human antibody, or fragments thereof.

In some embodiments, a CD3 antibody as described herein is a monoclonal antibody. For example, the CD3 antibody is a humanized monoclonal antibody or a chimeric monoclonal antibody.

The present invention encompasses an antibody comprising an Fc chain or domain, or portions thereof. In some embodiments, the Fc chain, or portion(s) thereof, comprises one or more constant domain(s) of the Fc chain of IgG1, IgG2, IgG3 or IgG4 (e.g., a CH2 or CH3 domain). In another embodiment, the invention encompasses molecules comprising an Fc chain or portion thereof, wherein the Fc chain or portion thereof comprises at least one amino acid modification (e.g. substitution) relative to a comparable wild-type Fc chain or portion thereof. Variant Fc regions are well known in the art, and are primarily used to alter the phenotype of the antibody comprising the variant Fc region as assayed in any of the binding activity or effector function assays well known in the art, e.g., ELISA, SPR analysis, or ADCC. Such variant Fc chains, or portions thereof, may extend the plasma half-life and stability exhibited by a bispecific antibody of the invention comprising an Fc chain or portion thereof. In another embodiment, the invention encompasses the use of any Fc variant known in the art.

In one embodiment, one or more modifications are made to the amino acids of the Fc chain to reduce the affinity and avidity of the Fc chain and, thus, the bispecific antibody of the invention, for one or more FcγR receptors. In a specific embodiment, the invention encompasses bispecific antibodies comprising a variant Fc chain, or portion thereof, wherein the variant Fc chain comprises at least one amino acid modification relative to a wild-type Fc chain which variant Fc region only binds one FcγR, wherein the FcγR is FcγRIIIA. In another specific embodiment, the invention encompasses bispecific antibodies comprising a variant Fc chain, or portion thereof, wherein the variant Fc chain comprises at least one amino acid modification relative to a wild type (WT) Fc chain which variant Fc region only binds one FcγR, wherein the FcγR is FcγRIIA. In another specific embodiment, the invention encompasses bispecific antibodies comprising a variant Fc chain or portion thereof, wherein the variant Fc chain comprises at least one amino acid modification relative to a wild-type Fc chain, which variant Fc chain only binds one FcγR, wherein the FcγR is FcγRIIB. In another embodiment, the invention encompasses molecules comprising a variant Fc chain wherein the variant confers or mediates decreased ADCC activity (or other effector function) and/or an increased binding to FcγRIIB (CD32B), relative to a molecule comprising no Fc chain or comprising a wild-type Fc chain, as measured using methods known to one skilled in the art and described herein.

The invention also encompasses the use of an Fc region comprising domains or regions from two or more IgG isotypes. As known in the art, amino acid modification of the Fc region may profoundly affect Fc-mediated effector function and/or binding activity. However, these alterations in functional characteristics may be further refined and/or manipulated when implemented in the context of selected IgG isotypes. Similarly, the native characteristics of the isotype Fc may be manipulated by one or more amino acid modifications. The multiple IgG isotypes (i.e., IgG1, IgG2, IgG3 and IgG4) exhibit differing physical and functional properties including serum half-life, complement fixation, FcγR binding affinities and effector function activities (e.g., ADCC, CDC) due to differences in the amino acid sequences of their hinge and/or Fc regions.

In one embodiment, the amino acid modification and IgG Fc region are independently selected based on their respective, separate binding and/or effector function activities in order to engineer a bispecific antibody with desired characteristics. In a particular embodiment, the amino acid modifications and IgG hinge/Fc regions have been separately assayed for binding and/or effector function activity as described herein or known in the art in the context of an IgG1. In one embodiment, the amino acid modification and IgG hinge/Fc region display similar functionality, e.g., decreased ADCC activity (or other effector function) and/or an increased binding to FcγRIIB in the context of the bispecific antibody or other Fc-containing molecule (e.g., and immunoglobulin). In another embodiment, the invention encompasses variant Fc regions comprising combinations of amino acid modifications known in the art and selected IgG regions that exhibit novel properties, which properties were not detectable when the modifications and/or regions were independently assayed as described herein.

One way of determining binding affinity of antibodies to CD3 is by measuring binding affinity of monofunctional Fab fragments of the antibody. To obtain monofunctional Fab fragments, an antibody (for example, IgG) can be cleaved with papain or expressed recombinantly. The affinity of a CD3 Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) or anti-mouse Fc or anti-human Fc using HBS-EP running buffer (0.01M HEPES, pH 7.4, 0.15 M NaCl, 3 mM EDTA, 0.005% v/v Surfactant P20). Biotinylated or Fc fusion human CD3 can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of CD3 on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_m$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any CD3, including human CD3, CD3 of another mammal (such as mouse CD3, rat CD3, or primate CD3), as well as different forms of CD3 (e.g., glycosylated CD3). Binding affinity of an antibody is generally measured at 25° C., but can also be measured at 37° C.

The antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for CD3, or portions thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human CD3, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antibody of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g., Tiller et al., J. Immunol. Methods, 329, 112, 2008; U.S. Pat. No. 7,314,622.

In an alternative, the polynucleotide sequence may be used for genetic manipulation to humanize the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to CD3 and greater therapeutic efficacy.

In some embodiments, the antibody has a modified constant region that removes or reduces Fc gamma receptor binding. For example, the Fc can be human IgG2 containing the mutation D265, in which the amino acid residues are numbered with reference to the wild type IgG2 sequence. Accordingly, in some embodiments, the constant region has a modified constant region having the sequence shown in SEQ ID NO: 80. In some embodiments, the antibody has a modified constant region having the sequence shown in SEQ ID NO: 81.

There are four general steps to humanize a monoclonal antibody. These are: (1) determining the nucleotide and predicted amino acid sequence of the starting antibody light and heavy variable regions (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of humanized antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239: 1534-1536, 1988, and Jones et al. Nature 321:522-525, 1986. Another reference describes rodent CDRs supported by recombinantly engineered rodent framework regions. See, for example, European Publication No. EP0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g., PCT Application No. PCT/GB99/01441; UK Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054, 297; 5,997,867; 5,866,692; 6,210,671; and 6,350,861; and in PCT Publication No. WO01/27160.

The general principles related to humanized antibodies discussed above are also applicable to customizing antibodies for use, for example, in other mammals (e.g., human, non-human primate, murine, donkey, sheep, rabbit, goat, guinea pig, camel, horse, or chicken). Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for CD3 or antigens of interest.

The antibodies as described herein can be bound to many different solid phase supports or carriers. Such supports can be active and/or inert. Well-known supports include polypropylene, polystyrene, polyethylene, dextran, nylon, amylases, glass, natural and modified celluloses, polyacrylamides, agaroses, and magnetite. The nature of the support can be either soluble or insoluble for purposes of the invention. Those skilled in the art will know of other suitable supports for binding antibodies, or will be able to ascertain such, using routine experimentation. In some embodiments, the support comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO87/04462), which are then transfected into host cells such as E. coli cells, simian COS cells, CHO cells, or myeloma cells that do not otherwise produce immunoglobulin protein, to obtain the synthesis of monoclonal antibodies in the recombinant host cells. See, e.g., PCT Publication No. WO87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

The CD3 or other antigen antibodies as described herein can be identified or characterized using methods known in the art, whereby antigen expression levels are detected and/or measured. In some embodiments, a CD3 antibody is identified by incubating a candidate agent with CD3 and monitoring binding and/or attendant reduction of CD3 expression levels. The binding assay may be performed with purified CD3 polypeptide(s), or with cells naturally expressing, or transfected to express, CD3 polypeptide(s). In one embodiment, the binding assay is a competitive binding assay, where the ability of a candidate antibody to compete with a known CD3 antibody for CD3 binding is evaluated. The assay may be performed in various formats, including the ELISA format.

Following initial identification, the activity of a candidate CD3 or other antigen antibody can be further confirmed and refined by bioassays, known to test the targeted biological activities. Alternatively, bioassays can be used to screen candidates directly. Some of the methods for identifying and characterizing antibodies are described in detail in the Examples.

CD3 or other antigen antibodies may be characterized using methods well known in the art. For example, one method is to identify the epitope to which it binds, or epitope mapping. There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a CD3 or other antigen antibody. In another example, the epitope to which the CD3 or other antigen antibody binds can be determined in a systematic screening by using overlapping peptides derived from the CD3 or other antigen sequence and determining binding by the CD3 or other antigen antibody. According to the gene fragment expression assays, the open reading frame encoding CD3 or other antigen is fragmented either randomly or by specific genetic constructions and the reactivity of the expressed fragments of CD3 or other antigen with the antibody to be tested is determined. The gene fragments may, for example, be produced by PCR and then transcribed and translated into protein in vitro, in the presence of radioactive amino acids. The binding of the antibody to the radioactively labeled CD3, or other antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant CD3 or other antigen in which various fragments of the CD3 or other antigen protein have been replaced (swapped) with sequences from an antigen from another species (e.g., mouse), or a closely related, but antigenically distinct protein (e.g., Trop-1). By assessing binding of the antibody to the mutant CD3 or other antigen, the importance of the particular CD3 or other antigen fragment to antibody binding can be assessed.

Yet another method which can be used to characterize a CD3 or other antigen antibody is using competition assays with other antibodies known to bind to the same antigen, i.e., various fragments on CD3 or other antigen, to determine if the CD3 or other antigen antibody binds to the same epitope as other antibodies, respectively. Competition assays are well known to those of skill in the art.

An expression vector can be used to direct expression of a CD3 or other antigen antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 11:202, 1993; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1:185, 1995; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO90/07936; WO94/03622; WO93/25698; WO93/25234; WO93/11230; WO93/10218; WO91/02805; U.S. Pat. Nos. 5,219,740 and 4,777,127; GB Pat. No. 2,200,651; and EP Pat. No. EPO 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO94/12649, WO93/03769; WO93/19191; WO94/28938; WO95/11984 and WO95/00655). Administration of DNA linked to killed adenovirus as described in Curiel, Hum. Gene Ther., 3:147, 1992 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO95/07994; WO96/17072; WO95/30763; and WO97/42338) and nucleic charge neutralization or fusion with cell membranes. Naked DNA can also be employed. Exemplary naked DNA introduction methods are described in PCT Publication No. WO90/11092 and U.S. Pat. No. 5,580,859. Liposomes that can act as gene delivery vehicles are described in U.S. Pat. No. 5,422,120; PCT Publication Nos. WO95/13796; WO94/23697; WO91/14445; and European Publication EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions comprising antibodies of the invention as described herein or made by the methods and having the characteristics described herein. As used herein, pharmaceutical compositions may comprise one or more antibodies that bind to a tumor antigen, one or more bispecific antibodies that bind to CD3 and a tumor antigen, and/or one or more polynucleotides comprising sequences encoding one or more these antibodies. These compositions may further comprise suitable excipients, such as pharmaceutically acceptable excipients including buffers, which are well known in the art.

In one embodiment, the present invention features a composition which is a combination of a CD3 antibody and a second therapeutic agent. In one embodiment, the second therapeutic agent is any agent that is advantageously combined with a CD3 antibody. Exemplary agents that may be advantageously combined with a CD3 antibody include, without limitation, other agents that bind and/or activate CD3 signaling (including other antibodies or antigen-binding fragments thereof, etc.) and/or agents which do not directly bind CD3 but nonetheless activate or stimulate immune cell activation. The present invention further includes additional combination therapies and co-formulations involving the CD3 antibodies of the present invention. The invention also provides methods of making any of these antibodies. The antibodies of this invention can be made by procedures known in the art including de novo protein synthesis and recombinant expression of nucleic acids encoding the binding proteins. The desired nucleic acid sequences may be produced by recombinant methods (e.g., PCR mutagenesis of an earlier prepared variant of the desired polynucleotide) or by solid-phase DNA synthesis. Usually recombinant expression methods are used. In one aspect, the invention provides a polynucleotide that comprises a sequence encoding a CD3 VH and/or VL. Because of the degeneracy of the genetic code, a variety of nucleic acid sequences encode each immunoglobulin amino acid sequence, and the present invention includes all nucleic acids encoding the binding proteins described herein.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in PCT Publication WO99/58572. For example, the constant region may be engineered to more resemble human constant regions to avoid immune response if the antibody is used in clinical trials and treatments in humans. See, for example, U.S. Pat. Nos. 5,997,867 and 5,866,692.

The CD3 antibodies as disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In some embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In some further embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes CD3 antibodies comprising variants of any of the HC VR, LC VR, and/or CDR amino acid sequences disclosed herein having one or more conservative substitutions. For example, the present invention includes CD3 antibodies having HC VR, LC VR, and/or CDR amino acid sequences with, e.g., 10 or fewer, 8 or fewer, 6 or fewer, 4 or fewer, etc. conservative amino acid substitutions relative to any of the HC VR, LC VR, and/or CDR amino acid sequences, as disclosed herein.

Accordingly, the invention encompasses modifications to the antibodies and polypeptides of the invention variants as described herein, including functionally equivalent antibodies which do not significantly affect their properties and variants which have enhanced or decreased activity and/or affinity. For example, the amino acid sequence may be mutated to obtain an antibody with the desired binding affinity to a tumor antigen and/or CD3. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 6 under the heading of "conservative substitutions." If such substitutions result in a change in biological activity, then more substantial changes, denominated "exemplary substitutions" in Table 6, or as further described below in reference to amino acid classes, may be introduced and the products screened.

TABLE 6

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |

TABLE 6-continued

| Original Residue (naturally occurring amino acid) | Conservative Substitutions | Exemplary Substitutions |
|---|---|---|
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:
 (1) Non-polar: Norleucine, Met, Ala, Val, Leu, Ile;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In some embodiments, no more than one to three conservative amino acid substitutions are made within a CDR domain. In still other embodiments, the CDR domain is VH CDR3 and/or VL CDR3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate macrophages; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 29:2613-2624, 1999; PCT Application No. PCT/GB99/01441, and/or UK Application No. 9809951.8. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using BIACORE™ surface plasmon resonance analysis, which detects differences in binding affinity of about 2-fold or greater. BIACORE™ is particularly useful when the starting antibody already binds with a relatively high affinity, for example a $K_D$ of about 10 nM or lower. Screening using BIACORE™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using BIACORE™ surface plasmon resonance analysis, and selection using any method known in the art for selection, including phage display, yeast display, and ribosome display.

Techniques for isolating antibodies and preparing antibodies follow. However, it will be appreciated that the antibodies can be formed from, or incorporate, other polypeptides using techniques which are known in the art. For example, nucleic acid encoding a polypeptide of interest (e.g., a ligand, receptor or enzyme) can be isolated from a cDNA library prepared from tissue believed to possess the polypeptide mRNA and to express it at a detectable level. Libraries are screened with probes (such as antibodies or oligonucleotides of about 20-80 bases) designed to identify the gene of interest or the protein encoded by it. Screening the cDNA or genomic library with the selected probe may be conducted using standard procedures as described in chapters 10-12 of Sambrook et al., Molecular Cloning: A Laboratory Manual (New York: Cold Spring Harbor Laboratory Press, 1989).

CD3 Antibodies for Treating an Autoimmune Disorder

In one aspect, provided is a method of treating an autoimmune disorder in a subject, comprising administering to the subject in need thereof an effective amount of a composition comprising the antibodies as described herein.

As used herein, autoimmune disorders include, but are not limited to, inflammatory bowel disease, systemic lupus erythematosus, rheumatoid arthritis, diabetes (Type I), multiple sclerosis, Addison's disease, celiac disease, dermatomyositis, Graves' disease, hashimoto's thyroiditis, hashimoto's encephalopathy, Myasthenia gravis, reactive arthritis, Sjögren syndrome, atopic allergy, atopic dermatitis, autoimmune enteropathy, autoimmune hepatitis, autoimmune lymphoproliferative syndrome, autoimmune peripheral neuropathy, autoimmune pancreatitis, autoimmune polyendorcrine syndrome, autoimmune progesterone dermatitis, autoimmune urticarial, autoimmune uveitis, Bechet's disease, Castleman's disease, cold agglutinin disease, Crohn's disease, dermatomyositis, eosinophilic fasciitis, gastrointestinal pemphigoid, Goodpasture's syndrome, Guillain-Barré syndrome, hidradenitis suppurativa, narcolepsy, pemphigus vulgaris, polymyositis, relapsing polychrondritis, rheumatic fever, transverse myelitis, ulcerative colitis, undifferentiated connective tissue disease, vasculitis, and Wegener's granulomatosis.

Multispecific Antibodies and Uses Thereof

The CD3 antibodies of the present invention may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The CD3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce multispecific antibodies with a second binding specificity.

In one aspect, the antibody of the present invention is a multispecific antibody. In a particular embodiment, the CD3 antibody is a bispecific antibody that specifically binds human CD3. In some such embodiments, the bispecific antibody further specifically binds to a tumor antigen. In another such embodiment, the bispecific antibodies of the present invention simultaneously target T cells (CD3) and tumor cells and successfully direct and activate T cell cytotoxicity to tumor cells expressing a tumor antigen.

In further embodiments of each of the foregoing, the bispecific antibody that binds to CD3 is characterized by any one or more of the following characteristics: (a) treating, preventing, ameliorating one or more symptoms of a condition associated with malignant cells expressing a specific tumor antigen in a subject (e.g., B-cell related cancer such as multiple myeloma); (b) inhibiting tumor growth or progression in a subject (who has a malignant tumor expressing a specific tumor antigen); (c) inhibiting metastasis of cancer (malignant) cells expressing a specific tumor antigen in a subject (who has one or more malignant cells expressing a tumor antigen); (d) inducing regression (e.g., long-term regression) of a tumor expressing a tumor antigen; (e) exerting cytotoxic activity in malignant cells expressing a tumor antigen; (f) increasing the progression-free survival of a subject with a tumor associated disorder; (g) increasing the overall survival of a subject with a tumor associated disorder; (h) reducing use of additional chemotherapeutic or cytotoxic agents in a subject with a tumor associated disorder; (i) reducing the tumor burden in a subject with a tumor associated disorder; or (j) blocking tumor antigen interaction with other yet to be identified factors.

As used herein, the bispecific antibody of the present invention refers to a complex of two or more polypeptide chains, each comprising at least one antibody VL region and one antibody VH region or fragment thereof, wherein the VL and VH regions in each polypeptide chain are from different antibodies. In specific aspects, bispecific antibody includes dimers or tetramers of polypeptide chains containing both a VL and VH region. The individual polypeptide chains comprising the multimeric proteins may be covalently joined to at least one other peptide of the multimer by interchain disulfide bonds.

Figure 1:
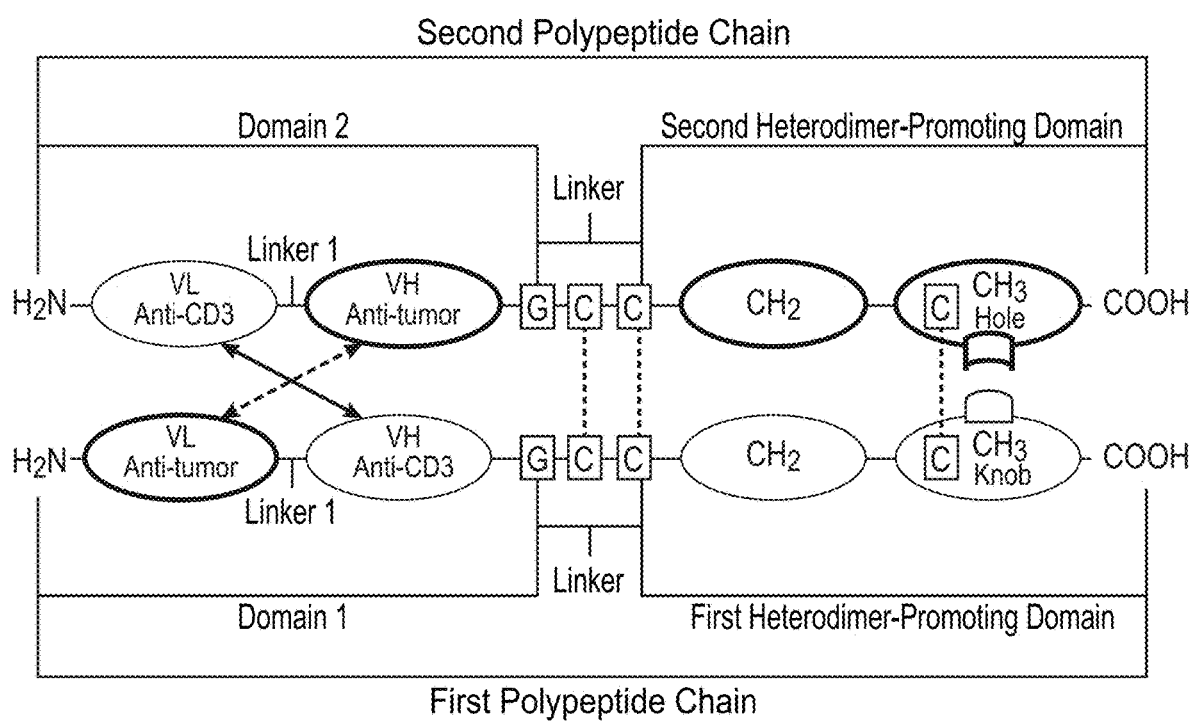

In some such embodiments, the bispecific antibodies of the present invention comprise a first heterodimer-promoting domain on the first polypeptide chain and a second heterodimer-promoting domain on the second polypeptide chain (FIG. 1). Taken together, the first and second heterodimer-promoting domains drive heterodimerization and/or stabilize the bispecific antibody (e.g., by interaction of a knob and hole on complementary heterodimer-promoting domains) and/or serve to stabilize the bispecific antibody. In some embodiments, the first heterodimer-promoting domain and the second heterodimer-promoting domain each comprise a CH2 domain and a CH3 domain, wherein the amino acid sequence of each of the CH2 domains and/or each of the CH3 domains is modified to drive heterodimerization and/or stabilize the bispecific antibody.

In some embodiments, the first heterodimer-promoting domain may comprise an Fc chain having a CH2 and/or CH3 domain modified to comprise either a knob (protuberance) or a hole (cavity). In some such embodiments, the amino acid sequence of the CH2 domain and/or the CH3 domain comprises at least one amino acid modification, wherein: (a) the CH3 domain of the first heterodimer-promoting domain forms a knob; and (b) the CH3 domain of the second heterodimer-promoting domain forms a hole. In another such embodiment, the CH3 domain of the first heterodimer-promoting domain comprises mutations Y349C and/or T366W; and the CH3 domain of the second heterodimer-promoting domain comprises mutations S354C, T366S, L368A, and/or Y407V, (numbering according to the EU index).

In one embodiment, the first heterodimer-promoting domain may comprise a CH2 and/or CH3 domain modified to comprise a knob (protuberance) comprising a sequence of SEQ ID NO: 78, if the second heterodimer-promoting domain comprise a CH2 and/or CH3 domain modified to comprise a hole (cavity). In another embodiment, the first heterodimer-promoting domain may comprise a hole (cavity) comprising a sequence of SEQ ID NO: 79, if the second heterodimer-promoting domain comprise a CH2 and/or CH3 domain modified to comprise a knob (protuberance).

Each polypeptide chain of the bispecific antibody comprises a VL region and a VH region, which may be covalently linked by a glycine-serine linker comprising glycine and serine residues (Linker 1 or Linker 2) such that the antibody binding domains are constrained from self-assembly. In addition, each polypeptide chain comprises a heterodimerization domain, which promotes heterodimerization and/or stabilization of the multiple polypeptide chains and reduces the probability of homodimerization of the different polypeptide chains. The heterodimerization domain may be located at the N-terminal of the polypeptide chain or the C-terminal. The heterodimerization domain may comprise a cysteine linker (Linker 3) that is 1, 2, 3, 4, 5, 6, or more amino acid residues in length. Interaction of two of the polypeptide chains may produce two VL/VH pairings, forming two epitope binding domains, i.e., a bivalent molecule. Neither the VH or VL region is constrained to any position within the polypeptide chain, i.e., restricted to the amino terminal or the carboxy terminal, nor are the regions restricted in their relative positions to one another, i.e., the VL region may be N-terminal to the VH region and vice versa. The only restriction is that a complimentary polypeptide chain be available in order to form a functional bispecific antibody. Where the VL and VH regions are derived from antibodies specific for different antigens, formation of a functional bispecific antibody requires the interaction of two different polypeptide chains, i.e., formation of a heterodimer. In contrast, where two differing polypeptide chains are free to interact, e.g., in a recombinant expression system, one comprising a VLA and a VHB (A, being a first epitope and B, being a second epitope) and the other comprising a VLB and a VHA, two differing binding sites may form: VLA-VHA and VLB-VHB. For all bispecific antibody polypeptide chain pairs, misalignment or misbinding of the two chains is a possibility, e.g., interaction of VL-VL or VH-VH regions. However, purification of functional bispecific antibodies is easily managed based on the immunospecificity of the properly dimerized binding site using any affinity based method known in the art or exemplified herein, e.g., affinity chromatography.

In one embodiment, the polypeptide chains of the bispecific antibody may comprise various linkers and peptides. The linkers and peptides may be 0, 1, 2, 3, 4, 5, 6, 7, 8, 9 or more amino acids.

In some embodiments, Domain 1 is covalently bound to the first heterodimer-promoting domain via a cysteine linker and Domain 2 is covalently bound to the second heterodimer-promoting domain via a cysteine linker. The cysteine linkers each include at least one cysteine residue to permit intramolecular disulfide bonding. In further embodiments of each of the foregoing, the cysteine linker (Linker 3) comprises at least five amino acids.

In some embodiments, the first polypeptide chain is covalently bound to the second polypeptide chain by at least one disulfide bond. In some such embodiments, at least one disulfide bond forms between Linker 3 of the first polypeptide chain and Linker 3 of the second polypeptide chain. In another such embodiment, at least one disulfide bond is formed between the first heterodimer-promoting domain and the second heterodimer-promoting domain. In specific embodiments, each disulfide bond is formed by linking two cysteine residues. In an aspect of the present invention, a bispecific antibody, as shown in FIG. 1, comprises a first polypeptide chain and a second polypeptide chain. In some such embodiments, Linker 3 may comprise a truncated human IgG1 lower hinge region having the sequence of SEQ ID NO: 64 with at least one glycine residue preceding the lower hinge region.

The bispecific antibodies of the invention may simultaneously bind two separate and distinct epitopes. In certain embodiments, at least one epitope binding site is specific for the CD3 determinant expressed on an immune effector cell e.g., expressed on T lymphocytes. In one embodiment, the bispecific antibody molecule binds to the effector cell determinant and also activates the effector cell.

In one aspect, the invention provides for a first polypeptide chain and a second polypeptide chain. In one embodiment the first polypeptide chain comprises an amino acid sequence as set forth as SEQ ID NO: 36. In another embodiment, the second polypeptide chain comprises an amino acid sequence as set forth as one or more of the SEQ ID NO: 37 or 38 (Table 7). In a preferred embodiment, the first polypeptide chain comprises an amino acid sequence as set forth as SEQ ID NO: 36; and the second polypeptide chain comprises an amino acid sequence as set forth as SEQ ID NO: 37 or 38. In one embodiment, the second polypeptide chain is any polypeptide which is to be associated with the first polypeptide chain via an interface. Table 7 shows sequences of first polypeptide chain and second polypeptide chain for GUCY2c-H2B4 and GUCY2c-2B5 bispecific antibodies.

TABLE 7

| Bispecific Antibody | First polypeptide chain | Second polypeptide chain |
|---|---|---|
| GUCY2c-H2B4 | DIQLTQSPSSLSASVGDRVTITC RASESVDYYGTSLMQWYQQKP GKPPKLLIYAASNVESGVPSRFS GSGSGTDFTLTISSLQPEDFATY | DIVMTQSPDSLAVSLGERATINC KSSQSLFNVRSRKNYLAWYQQK PGQPPKLLISWASTRESGVPDR FSGSGSGTDFTLTISSLQAEDVA |

TABLE 7-continued

| Bispecific Antibody | First polypeptide chain | Second polypeptide chain |
|---|---|---|
|  | YCQQTRKVYTFGQGTKLEIKGG GSGGGGEVQLVESGGGLVQPG GSLRLSCAASGFTFSDYYMTWV RQAPGKGLEWVAFIRNRARGYT SDHNPSVKGRFTISRDNAKNSLY LQMNSLRAEDTAVYYCARDRPS YYVLDYWGQGTTVTVSSGCPPC PAPEAAGAPSVFLFPPKPKDTLM ISRTPEVTCVVVDVSHEDPEVKF NWYVDGVEVHNAKTKPREEQY NSTYRVVSVLTVLHQDWLNGKE YKCKVSNKALPAPIEKTISKAKG QPREPQVCTLPPSREEMTKNQV SLWCLVKGFYPSDIAVEWESNG QPENNYKTTPPVLDSDGSFFLY SKLTVDKSRWQQGNVFSCSVM HEALHNHYTQKSLSLSPG (SEQ IN NO: 36) | VYYCKQSYDLFTFGSGTKLEIKG GGSGGGGEVQLVESGGGLVQP GGSLRLSCAASGYTFTSYWMH WVRQAPGKGLEWIGEIKPSNGL TNYIEKFKNRFTISVDKAKNSAYL QMNSLRAEDTAVYYCTRTITTTE GYWFFDVWGQGTLVTVSSGCP PCPAPEAAGAPSVFLFPPKPKDT LMISRTPEVTCVVVDVSHEDPEV KFNWYVDGVEVHNAKTKPREE QYNSTYRVVSVLTVLHQDWLNG KEYKCKVSNKALPAPIEKTISKAK GQPREPQVYTLPPCREEMTKNQ VSLSCAVKGFYPSDIAVEWESN GQPENNYKTTPPVLDSDGSFFL VSKLTVDKSRWQQGNVFSCSV MHEALHNHYTQKSLSLSPG (SEQ IN NO: 37) |
| GUCY2c-2B5 | DIQLTQSPSSLSASVGDRVTITC RASESVDYYGTSLMQWYQQKP GKPPKLLIYAASNVESGVPSRFS GSGSGTDFTLTISSLQPEDFATY YCQQTRKVYTFGQGTKLEIKGG GSGGGGEVQLVESGGGLVQPG GSLRLSCAASGFTFSDYYMTWV RQAPGKGLEWVAFIRNRARGYT SDHNPSVKGRFTISRDNAKNSLY LQMNSLRAEDTAVYYCARDRPS YYVLDYWGQGTTVTVSSGCPPC PAPEAAGAPSVFLFPPKPKDTLM ISRTPEVTCVVVDVSHEDPEVKF NWYVDGVEVHNAKTKPREEQY NSTYRVVSVLTVLHQDWLNGKE YKCKVSNKALPAPIEKTISKAKG QPREPQVCTLPPSREEMTKNQV SLWCLVKGFYPSDIAVEWESNG QPENNYKTTPPVLDSDGSFFLY SKLTVDKSRWQQGNVFSCSVM HEALHNHYTQKSLSLSPG (SEQ ID NO: 36) | DIQMTQSPSSLSASVGDRVTITC TSSQSLFNVRSRKNYLAWYQQK PGKAPKLLIYWASTRESGVPSRF SGSGSGTDFTLTISSLQPEDFAT YYCKQSYDLFTFGGGTKVEIKG GGSGGGGEVQLVESGGGLVQP GGSLRLSCAASGYTFTSYWMH WVRQAPGKGLEWIGEIKPSNGL TNYIEKFKNRFTISVDKAKNSAYL QMNSLRAEDTAVYYCTRTITTTE GYWFFDVWGQGTLVTVSSGCP PCPAPEAAGAPSVFLFPPKPKDT LMISRTPEVTCVVVDVSHEDPEV KFNWYVDGVEVHNAKTKPREE QYNSTYRVVSVLTVLHQDWLNG KEYKCKVSNKALPAPIEKTISKAK GQPREPQVYTLPPCREEMTKNQ VSLSCAVKGFYPSDIAVEWESN GQPENNYKTTPPVLDSDGSFFL VSKLTVDKSRWQQGNVFSCSV MHEALHNHYTQKSLSLSPG (SEQ ID NO: 38) |

In particular embodiments, the bispecific antibody of the present invention (a) binds to the extracellular domain of human tumor antigen; (b) demonstrates an extended serum and tumor half-life of between 30 min to 100 days; and/or (c) demonstrates a lower $EC_{50}$ value of between 0.0001 nM and 100 nM in the presence of increased tumor expression levels or increased receptor density levels.

In one embodiment, the epitope-binding domain is capable of binding the a tumor-associated antigen that is associated with breast, ovarian, thyroid, prostate, cervical, lung (including but not limited to non-small cell lung cancer and small cell lunch cancer), bladder, endometrial, head and neck, testicular, glioblastoma and digestive system cancers. Cancer of the digestive system includes but is not limited to cancers of the esophagus, stomach, small intestine, colon, rectum, anus, liver, gall bladder, appendix, bile ducts and pancreas. In specific embodiments, the therapy activates a cytolytic T cell response.

Effector Null Mutations in Human IgG1 CH2-CH3

The Fc chain of human IgG1 was modified to introduce mutations L234A, L235A and G237A (SEQ ID NO: 82, numbering according to the EU index) using standard primer-directed PCR mutagenesis to oblate effector function due to binding to FcγRIII providing for an effector function null phenotype (Canfield et al., J. Exp. Med (1991) 173: 1483-1491; Shields et al., J. Biol. Chem. (2001) 276:6591-604).

Knobs-in-Holes Mutations in Human IgG1 CH2-CH3

Knobs-in-holes is an effective design strategy known in the art for engineering antibody heavy chain homodimers for heterodimerization. In this approach a 'knob' variant was obtained by replacement of a small amino acid with a larger one in one chain of the Fc chain of IgG1, e.g., Y349C and T366W (numbering according to the EU index). The 'knob' was designed to insert into a 'hole' in the CH3 domain of the complimentary chain of the Fc chain created by replacement of a large residue with a smaller one e.g., S354C, T366S, L368A and Y407V (numbering according to the EU index).

In some embodiment, complimentary mutations were introduced to derive heterodimerization of the resultant Fc chains, such that each Fc chain would carry one set of mutations, Y349C and T366W for the knob (or protuberance) Fc chain (SEQ ID NO: 78), or S354C, T366S, L368A and Y407V for the hole (or cavity) Fc chain (SEQ ID NO: 79), as provided in Table 8. When co-transfected into a suitable mammalian host the DNA encoding the amino acid sequences for example of SEQ ID NOs: 78 and 79 produce an Fc domain that is predominantly bispecific antibody possessing one knob (or protuberance) Fc chain associated with one hole (or cavity) Fc chain.

TABLE 8

| | |
|---|---|
| Knob Fc chain Mutations (SEQ ID NO: 78) | APEAAGAPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVCTLPPSREEMTKNQV SLWCLVKGFYPSDIAVEWESNGQPENNYKTTPPVLDSDGSFFLY SKLTVDKSRWQQGNVFSCSVMHEALHNHYTQKSLSLSPG |
| Hole Fc chain Mutations (SEQ ID NO: 79) | APEAAGAPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPCREEMTKNQV SLSCAVKGFYPSDIAVEWESNGQPENNYKTTPPVLDSDGSFFLV SKLTVDKSRWQQGNVFSCSVMHEALHNHYTQKSLSLSPG |

The CD3-tumor antigen bispecific antibodies of the present invention are stable against aggregation in thermal stability studies and, potent bispecific antibody-Fc fusions targeting both human CD3 and a tumor antigen. The knob-in-hole Fc domain allows for improved expression in CHO cells and improved purification resulting in high purity of desired heterodimer. The mutations engineered within the Fc domain abrogate FcγR binding thus potentially avoiding ADCC mediated T cell depletion. Further, the incorporation of the Fc domain to a bispecific antibody enhances stability of the molecule as shown by Differential Scanning calorimetry (DSC).

If the bispecific antibody may be engineered to comprise at least one cysteine residue that may interact with a counterpart cysteine residue on another polypeptide chain of the invention to form an inter-chain disulfide bond. The inter-chain disulfide bonds may serve to stabilize the bispecific antibody, improving expression and recovery in recombinant systems, resulting in a stable and consistent formulation, as well as, improving the stability of the isolated and/or purified product in vivo. The cysteine residue or residues may be introduced as a single amino acid or as part of larger amino-acid sequence, e.g., hinge region, in any portion of the polypeptide chain. In a specific aspect, at least one cysteine residue is engineered to occur at the C-terminus of the polypeptide chain.

The invention encompasses methods and compositions for treatment, prevention or management of cancer in a subject, comprising administering to the subject a therapeutically effective amount of an antibody engineered in accordance with the invention, which molecule further binds a cancer antigen. Antibodies of the present invention may be particularly useful for the prevention, inhibition, reduction of growth and/or regression of primary tumors and metastasis of cancer cells. Although not intending to be bound by a particular mechanism of action, antibodies of the invention may mediate effector function which may result in tumor clearance, tumor reduction or a combination thereof.

In one aspect, the present invention provides therapeutic treatment methods for stimulating T cell activation using a CD3 antibody of an antibody of the invention, wherein the therapeutic methods comprise administering a therapeutically effective amount of a pharmaceutical composition comprising an antibody of the invention to a subject in need thereof. The disorder treated is any disease or condition which is improved, ameliorated, inhibited or prevented by stimulation of CD3 activity or signaling. In specific embodiments, the present invention provides bispecific antigen-binding molecules, e.g., bispecific antibodies that bind CD3 and a target antigen.

In one aspect, the invention provides methods of inhibiting growth of a tumor, comprising contacting the tumor with an effective amount of an antibody that binds CD3, including each of those antibodies described herein.

In another aspect, the invention provides a method of inhibiting the growth of a tumor in a subject, comprising administering to the subject a therapeutically effective amount of an antibody that binds CD3, including each of those antibodies described herein.

In another aspect, the invention provides a method of modulating angiogenesis in a subject, comprising administering to the subject a therapeutically effective amount of an antibody that binds CD3, including each of those antibodies described herein.

In another aspect, the invention provides a method of reducing the tumorigenicity of a tumor in a subject, comprising administering to the subject a therapeutically effective amount of an antibody that binds CD3, including each of those antibodies described herein.

In one aspect, the invention provides a method for treating a condition associated with tumor antigen expression in a subject. Accordingly, a tumor antigen by engineering the bispecific antibody to immunospecifically recognizes the tumor antigen and a CD3 antigen on T cells. The bispecific antibodies that have been engineered according to the invention are useful for prevention or treatment of cancer, since they have a cytotoxic activity by CD3 antibody induced activated killer T cells.

In a particular embodiment, the present invention provides a method of treating cancer. In specific embodiments, the cancer is breast, ovarian, thyroid, prostate, cervical, lung (including but not limited to non-small cell lung cancer and small cell lunch cancer), bladder, endometrial, head and neck, testicular, glioblastoma cancer, or a cancer of digestive system. In certain embodiments, the cancer of digestive system is selected from the group consisting of esophagus, stomach, small intestine, colon, rectum, anus, liver, gall bladder, appendix, bile ducts, and pancreas.

In one aspect, the present invention provides an antibody, a bispecific antibody, or a pharmaceutical composition as disclosed herein for use in therapy. In a particular embodiment, the invention also provides a CD3 bispecific antibody for use in the method of treating cancer defined herein. In specific embodiments, the therapy activates a cytolytic T cell response.

The present invention further provides an antibody, or a bispecific antibody as disclosed herein for use in the manufacture of a medicament for use in therapy. In some embodiments, the therapy is a treatment of a cancer. In some embodiments, the cancer is selected from the group consisting of breast, ovarian, thyroid, prostate, cervical, lung (including but not limited to non-small cell lung cancer and small cell lunch cancer), bladder, endometrial, head and neck, testicular, glioblastoma cancer, and a cancer of digestive system. In certain embodiments, the cancer of digestive system is selected from the group consisting of esophagus, stomach, small intestine, colon, rectum, anus, liver, gall bladder, appendix, bile ducts, and pancreas.

In one aspect, the present invention provides a polynucleotide that encodes an antibody or a bispecific antibody as disclosed herein. In another embodiment, the invention provides a vector comprising polynucleotides as disclosed herein. In yet another embodiment, the invention provides a host cell comprising the vectors as disclosed herein. In some such embodiments, the host cell recombinantly produces the antibody or the bispecific antibody as disclosed herein. In specific embodiments, the host cell is selected from the group consisting of bacterial cell lines, mammalian cell lines, insect cell lines, yeast cell lines and in vitro cell free protein synthesis systems. In a particular embodiment, the mammalian cell line is a CHO cell line.

In one aspect, provided is a method of treating a cancer in a subject in need thereof comprising a) providing the bispecific antibody as described herein, and b) administering said bispecific antibody to said subject.

In some embodiments, provided is a method of inhibiting tumor growth or progression in a subject who has malignant cells expressing a tumor antigen, comprising administering to the subject in need thereof an effective amount of a composition comprising the antibodies, as described herein. In some embodiments, provided is a method of inhibiting metastasis cells expressing a tumor antigen in a subject, comprising administering to the subject in need thereof an effective amount of a composition comprising the antibodies as described herein. In some embodiments, provided is a method of inducing tumor regression in malignant cells in a subject, comprising administering to the subject in need thereof an effective amount of a composition comprising the antibodies as described herein.

In a specific aspect, antibodies of the invention inhibit or reduce the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of the antibody or a bispecific antibody of the invention.

In a specific aspect, antibodies kill cells or inhibits or reduces the growth of cancer cells at least 5%, at least 10%, at least 20%, at least 25%, at least 30%, at least 35%, at least 40%, at least 45%, at least 50%, at least 60%, at least 70%, at least 75%, at least 80%, at least 85%, at least 90%, at least 95%, or at least 100% better than in the absence of the antibody or a bispecific antibodies of the invention.

In one aspect, the invention provides an effective amount of a composition (e.g., pharmaceutical composition) comprising a bispecific antibody as described herein for treating a condition (e.g., cancer) associated with a tumor antigen expression in a subject in need thereof.

In another aspect, the invention provides the antibodies as described herein for use in treating a condition (e.g., cancer) associated with a tumor antigen expression in a subject in need thereof. In some embodiments, provided is the antibodies as described herein for inhibiting tumor growth or progression in a subject who has malignant cells expressing a tumor antigen. In some embodiments, provided is the antibodies as described herein for inhibiting metastasis of malignant cells expressing a tumor antigen in a subject in need thereof. In some embodiments, provided is the antibodies as described herein for inducing tumor regression in a subject who has malignant cells expressing a tumor antigen.

In another aspect, the invention provides a use of the antibodies as described herein in the manufacture of a medicament for treating a condition (e.g., cancer) associated with a tumor antigen expression. In some embodiments, provided is a use of the antibodies as described herein in the manufacture of a medicament for inhibiting tumor growth or progression. In some embodiments, provided is a use of the antibodies as described herein in the manufacture of a medicament for inhibiting metastasis of malignant cells expressing a tumor antigen. In some embodiments, provided is a use of the antibodies as described herein in the manufacture of a medicament for inducing tumor regression.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

The invention further encompasses administering the molecules of the invention in combination with other therapies known to those skilled in the art for the treatment or prevention of cancer including but not limited to, current standard and experimental chemotherapies, biological therapies, immunotherapies, radiation therapies, or surgery. In some aspects, the molecules of the invention may be administered in combination with a therapeutically or prophylactically effective amount of one or more agents, therapeutic antibodies or other agents known to those skilled in the art for the treatment and/or prevention of cancer.

Accordingly, methods for treating cancer include administering to a subject in need thereof an effective amount of multispecific antibody (e.g., bispecific antibody) of the present invention in combination with a chemotherapeutic agent. Such combination treatment may be administered separately, sequentially, or simultaneously.

The dosage amounts and frequencies of administration provided herein are encompassed by the terms therapeutically effective and prophylactically effective. The dosage and frequency further may vary according to factors specific for each subject depending on the specific therapeutic or prophylactic agents administered, the severity and type of cancer, the route of administration, as well as age, body weight, response, and the past medical history of the subject. Suitable regimens may be selected by one skilled in the art by considering such factors and by following, for example, dosages reported in the literature and recommended in the Physician's Desk Reference ($56^{th}$ ed., 2002).

Accordingly, in addition to redirecting T cells to tumor-specific antigens, the bispecific T cell engaging molecules can also be used to carry other diagnostic or therapeutic compounds to cells expressing a tumor on their surface. Thus, a bispecific T cell engaging molecule may be attached directly or indirectly, e.g., via a linker, to a drug so that it will be delivered directly to cells bearing a tumor. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Pharmaceutical Compositions

The present invention further provides a composition comprising a therapeutically effective amount of an antibody disclosed herein, and a pharmaceutically acceptable carrier.

The antibodies of the present invention may be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., 18$^{th}$ ed., 1995, provides a compendium of formulation techniques as are generally known to practitioners.

These pharmaceutical compositions may be administered by any means known in the art that achieve the generally intended purpose to treat cancer. The route of administration may be parenteral, defined herein as referring to modes of administration that include but not limited to intravenous, intramuscular, intraperitoneal, subcutaneous, and intraarticular injection and infusion. The manner of administration and dosing of the of the molecules according to the invention (e.g., antibodies, pharmaceutical composition) depend on the type of disease to be combated, where appropriate the stage thereof, the antigen to be controlled, the kind of concurrent treatment, if any, frequency of treatment, the nature of the effect desired, and also the body weight, the age, the health the diet and the sex of the subject. Thus, the dosage regimen actually employed can vary widely and therefore can deviate from the dosage regimens set forth herein.

Various formulations of the antibodies of the present antibodies may be used for administration. In some embodiments, the antibodies may be administered neat. In some embodiments, the antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 21st Ed. Mack Publishing, 2005.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

The antibodies as described herein can be administered using any suitable method, including by injection (e.g., intraperitoneally, intravenously, subcutaneously, intramuscularly, etc.). The antibody, e.g., monoclonal antibody or bispecific antibody, also be administered via inhalation, as described herein. Generally, for administration of the antibody of the present invention, the dosage depends upon the host treated and the particular mode of administration. In one embodiment, the dose range of the antibody of the present invention will be about 0.001 µg/kg body weight to about 20,000 µg/kg body weight. The term "body weight" is applicable when a patient is being treated. When isolated cells are being treated, "body weight" as used herein refers to a "total cell body weight". The term "total body weight" may be used to apply to both isolated cell and patient treatment. All concentrations and treatment levels are expressed as "body weight" or simply "kg" in this application and are also considered to cover the analogous "total cell body weight" and "total body weight" concentrations. However, those of ordinary skill in the art will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 µg/kg, 5 µg/kg, 10 µg/kg, 12 µg/kg, 15 mg/kg, 20 mg/kg, and/or 30 mg/kg. All of these dosages are exemplary, and any dosage in-between these points is also expected to be of use in the invention. Any of the above dosage ranges or dosage levels may be employed for an antibody of the present invention. For repeated administrations over several days or longer, depending on the condition, the treatment is sustained until a desired suppression of symptoms occurs or until sufficient therapeutic levels are achieved, for example, to inhibit or delay tumor growth/progression or metastasis of cancer cells.

Other dosage regimens may also be useful, depending on the pattern of pharmacokinetic decay that the practitioner wishes to achieve. In one embodiment, the antibody of the present invention is administered in an initial priming dose followed by a higher and/or continuous, substantially constant dosage. In some embodiments, dosing from one to four times a week is contemplated. In some embodiments, dosing once a month or once every other month or every three months is contemplated. The progress of this therapy is easily monitored by conventional techniques and assays. The dosing regimen can vary over time.

For the purpose of the present invention, the appropriate dosage of an antibody will depend on the antibody or compositions thereof employed, the type and severity of symptoms to be treated, whether the agent is administered for therapeutic purposes, previous therapy, the patient's clinical history and response to the agent, the patient's clearance rate for the administered agent, and the discretion of the attending physician. Typically the clinician will administer an antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of antibodies may be appropriate. Various formulations and devices for achieving sustained release are known in the art.

In one embodiment, dosages for an antibody may be determined empirically in individuals who have been given one or more administration(s) of the antibody. Individuals are given incremental dosages of an antibody. To assess efficacy, an indicator of the disease can be followed.

In certain embodiments, the administration of an antibody leads to at least one effect selected from the group consisting of inhibition of tumor growth, tumor regression, reduction in the size of a tumor, reduction in tumor cell number, delay in tumor growth, abscopal effect, inhibition of tumor metastasis, reduction in metastatic lesions over time, reduced use of chemotherapeutic or cytotoxic agents, reduction in tumor burden, increase in progression-free survival, increase in overall survival, complete response, partial response, and stable disease.

Administration of an antibody in accordance with the method in the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced doses.

In some embodiments, more than one antibody may be present. At least one, at least two, at least three, at least four, at least five different or more antibodies can be present. Generally, those antibodies may have complementary activities that do not adversely affect each other. For example, one or more of the following antibody may be used: a first CD3 antibody directed to one epitope on CD3 and a second CD3 antibody directed to a different epitope on CD3.

In some embodiments, the antibodies of this disclosure are particularly useful for parenteral administration, such as intravenous administration or administration into a body cavity or lumen of an organ.

Therapeutic formulations of the antibody used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing the antibody are prepared by methods known in the art, such as described in Epstein, et al., Proc. Natl. Acad. Sci. USA 82:3688, 1985; Hwang, et al., Proc. Natl Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The formulations to be used for in vivo administration must be sterile. This is readily accomplished by, for example, filtration through sterile filtration membranes. Therapeutic antibody (e.g., CD3 antibody) compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Compositions within the scope of the invention include all compositions wherein an antibody is present in an amount that is effective to achieve the desired medical effect for treating cancer. While individual needs may vary from one patient to another, the determination of the optimal ranges of effective amounts of all of the components is within the ability of the clinician of ordinary skill.

Examples of such compositions, as well as how to formulate, are also described in an earlier section and below. In some embodiments, the composition comprises one or more antibodies. In some embodiments, the antibody is a human antibody, a humanized antibody, or a chimeric antibody. In some embodiments, the antibody comprises a constant region that is capable of triggering a desired immune response, such as antibody-mediated lysis or ADCC. In some embodiments, the antibody comprises a constant region that does not trigger an unwanted or undesirable immune response, such as antibody-mediated lysis or ADCC.

It is understood that the compositions can comprise more than one antibody, such as a mixture of CD3 antibodies that recognize different epitopes of CD3 or CD3 and a tumor antigen). Other exemplary compositions comprise more than one antibody, that recognize the same epitope(s), or different species of antibodies, or that bind to different epitopes of CD3 and a tumor antigen (e.g., human CD3).

In some embodiments, the antibody may be administered in combination with the administration of one or more additional therapeutic agents. These include, but are not limited to, the administration of a biotherapeutic agent and/or a chemotherapeutic agent, such as but not limited to, a vaccine, a CAR-T cell-based therapy, radiotherapy, a cytokine therapy, a CD3 bispecific antibody, an inhibitor of other immunosuppressive pathways, an inhibitor of angiogenesis, a T cell activator, an inhibitor of a metabolic pathway, an mTOR inhibitor, an inhibitor of an adenosine pathway, a tyrosine kinase inhibitor including but not limited to Inlyta, ALK inhibitors and sunitinib, a BRAF inhibitor, an epigenetic modifier, an 001 inhibitor, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD40, CD-40L, CTLA-4, OX-40, 4-1BB, TIGIT, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of biotherapeutic agents include therapeutic antibodies, immune modulating agents, and therapeutic immune cells.

Therapeutic antibodies may have specificity against a variety of different of antigens. For example, therapeutic antibodies may be directed to a tumor associated-antigen, such that binding of the antibody to the antigen promotes death of the cell expressing the antigen. In other example, therapeutic antibodies may be directed to an antigen (e.g. PD-1) on an immune cell, such that binding of the antibody prevents downregulation of the activity of the cell expressing the antigen (and thereby promotes activity of the cell expressing the antigen). In some situations, a therapeutic antibody may function through multiple different mechanisms (for example, it may both i) promote death of the cell expressing the antigen, and ii) prevent the antigen from causing down-regulation of the activity of immune cells in contact with the cell expressing the antigen).

Therapeutic antibodies may be directed to, for example, the antigens listed as follows. For some antigens, exemplary antibodies directed to the antigen are also included below (in brackets/parenthesis after the antigen). The antigens as follow may also be referred to as "target antigens" or the like herein. Target antigens for therapeutic antibodies herein include, for example: 4-1BB (e.g. utomilumab); 5T4; A33; alpha-folate receptor 1 (e.g. mirvetuximab soravtansine); Alk-1, BCMA [e.g. PF-06863135 (see U.S. Pat. No. 9,969, 809)]; BTN1A1 (e.g. see WO2018222689); CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), PF-06671008 (CD3/P-cadherin bispecific), PF-06863135 (CD3/BCMA bispecific), PF-07062119 (CD3/GUCY2c bispecific)] CD19 (e.g. blinatumomab, MOR208), CD20 (e.g. ibritumomab tiuxetan, obinutuzumab, ofatumumab, rituximab, ublituximab); CD22 (inotuzumab ozogamicin, moxetumomab pasudotox); CD25, CD28, CD30 (e.g. brentuximab vedotin); CD33 (e.g. gemtuzumab ozogamicin); CD38 (e.g. daratumumab, isatuximab), CD40, CD-401_, CD44v6; CD47, CD52 (e.g. alemtuzumab); CD63, CD79 (e.g. polatuzumab vedotin); CD80, CD123, CD276/B7-H3 (e.g. omburtamab); CDH17, CEA; ClhCG, CTLA-4 (e.g. ipilimumab, tremelimumab), CXCR4; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIll, Endosialin; EpCAM (e.g. oportuzumab monatox); FAP; Fetal Acetyl-choline Receptor; FLT3 (e.g. see WO2018/220584); GD2 (e.g. dinutuximab, 3F8); GD3; GITR; GloboH; GM1; GM2; GUCY2C (e.g. PF-07062119), HER2/neu [e.g. margetuximab, pertuzumab, trastuzumab; ado-trastuzumab emtansine, trastuzumab duocarmazine, PF-06804103 (see U.S. Pat. No. 8,828,401)]; HER3; HER4; ICOS; IL-10, ITG-AvB6; LAG-3 (e.g. relatlimab); Lewis-Y; LG; Ly-6; M-CSF [e.g. PD-0360324 (see U.S. Pat. No. 7,326,414)]; MCSP; mesothelin; MUC1; MUC2; MUC3; MUC4; MUC5AC; MUC5B, MUC7; MUC16, Notcht Notch3; Nectin-4 (e.g. enfortumab vedotin); OX40 [e.g. PF-04518600 (see U.S. Pat. No. 7,960,515)]; P-Cadherein [e.g. PF-06671008 (see WO2016/001810)]; PCDHB2; PD-1 [e.g. BCD-100, camrelizumab, cemiplimab, genolimzumab (CBT-501), MEDI0680, nivolumab, pembrolizumab, RN888 (see WO2016/092419), sintilimab, spartalizumab, STI-A1110, tislelizumab, TSR-042]; PD-L1 (e.g. atezolizumab, durvalumab, BMS-936559 (MDX-1105), or LY3300054); PDGFRA (e.g. olaratumab); Plasma Cell Antigen; PolySA; PSCA; PSMA; PTK7 [e.g. PF-06647020 (see U.S. Pat. No. 9,409,995)]; Ror1; SAS; SCRx6; SLAMF7 (e.g. elotuzumab); SHH; SIRPa (e.g. ED9, Effi-DEM); STEAP; TGF-beta; TIGIT; TIM-3; TMPRSS3; TNF-alpha precursor; TROP-2 (e.g sacituzumab govitecan); TSPAN8; VEGF (e.g. bevacizumab, brolucizumab); VEGFR1 (e.g. ranibizumab); VEGFR2 (e.g. ramucirumab, ranibizumab); Wue-1.

Therapeutic antibodies may have any suitable format. For example, therapeutic antibodies may have any format as described elsewhere herein. In some embodiments, a therapeutic antibody may be a naked antibody. In some embodiments, a therapeutic antibody may be linked to a drug/agent (also known as an "antibody-drug conjugate" (ADC)). In some embodiments, a therapeutic antibody against a particular antigen may incorporated into a multi-specific antibody (e.g. a bispecific antibody).

In some embodiments, an antibody directed to an antigen may be conjugated to a drug/agent. Linked antibody-drug molecules are also referred to as "antibody-drug conjugates" (ADCs). Drugs/agents can be linked to an antibody either directly or indirectly via a linker. Most commonly, toxic drugs are linked to an antibody, such that binding of the ADC to the respective antigen promotes the killing of cells that express the antigen. For example, ADCs that are linked to toxic drugs are particularly useful for targeting tumor associated antigens, in order to promote the killing of tumor cells that express the tumor associated antigens. In other embodiments, agents that may be linked to an antibody may be, for example, an immunomodulating agent (e.g. to modulate the activity of immune cells in the vicinity of the ADC), an imaging agent (e.g. to facilitate the imaging of the ADC in a subject or a biological sample from the subject), or an agent to increase the antibody serum half-life or bioactivity.

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015015448. In some embodiments, an ADC may have any of the features or characteristics of the ADCs provided in WO2016166629, which is hereby incorporated by reference for all purposes. Drugs/agents that can be linked to an antibody in the ADC format can include, for example, cytotoxic agents, immunomodulating agents, imaging agents, therapeutic proteins, biopolymers, or oligonucleotides.

Exemplary cytotoxic agents that may be incorporated in an ADC include an anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof.

Exemplary immunomodulating agents that may be incorporated in an ADC include gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-.alpha., -.beta. and -.gamma.), the stem cell growth factor designated "S 1 factor," erythropoietin and thrombopoietin, or a combination thereof.

Exemplary imaging agents that may be included in an ADC include fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraaza-cyclododecane-N,N',N'',N'''-tetraacetic acid (DOTA), 1,4,7-triazacyclononane-1,4,7-triacetic acid (NOTA), 1,4,7-triaza-cyclononane, 1-glutaric acid-4,7-acetic acid (deferoxamine), diethylenetriaminepentaacetic acid (DTPA), and 1,2-bis(o-aminophenoxy)ethane-N, N, N',N'-tetraacetic acid) (BAPTA).

Exemplary therapeutic proteins that may be included in an ADC include a toxin, a hormone, an enzyme, and a growth factor.

Exemplary biocompatible polymers that may be incorporated in an ADC include water-soluble polymers, such as polyethylene glycol (PEG) or its derivatives thereof and zwitterion-containing biocompatible polymers (e.g., a phosphorylcholine containing polymer).

Exemplary biocompatible polymers that may be incorporated in an ADC include anti-sense oligonucleotides.

In some embodiments, an antibody directed to an antigen provided herein may be incorporated into a bispecific antibody molecule. Bispecific antibodies are monoclonal antibodies that have binding specificity for at least two different antigens.

In some embodiments, a bispecific antibody comprises a first antibody variable domain and a second antibody variable domain, wherein the first antibody variable domain is capable of recruiting the activity of a human immune effector cell by specifically binding to CD3 as provided herein, and wherein the second antibody variable domain is capable of specifically binding to a target antigen. In some embodiments, the antibody has an IgG1, IgG2, IgG3, or IgG4 isotype. In some embodiments, the antibody comprises an immunologically inert Fc region. In some embodiments the antibody is a human antibody or humanized antibody.

The target antigen is typically expressed on a target cell in a diseased condition (e.g. a cancer cell). Examples of the target antigens of particular interest in bispecific antibodies include, but are not limited to, BCMA, EpCAM (Epithelial Cell Adhesion Molecule), CCR5 (Chemokine Receptor type 5), CD19, HER (Human Epidermal Growth Factor Receptor)-2/neu, HER-3, HER-4, EGFR (Epidermal Growth Factor Receptor), PSMA, CEA, MUC-1 (Mucin), MUC2, MUC3, MUC4, MUC5AC, MUC5B, MUC7, ClhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Shh (Sonic Hedgehog), Wue-1, Plasma Cell Antigen, (membrane-bound) IgE, MCSP (Melanoma Chondroitin Sulfate Proteoglycan), CCR8, TNF-alpha precursor, STEAP, mesothelin, A33 Antigen, PSCA (Prostate Stem Cell Antigen), Ly-6; desmoglein 4, E-cadherin neoepitope, Fetal Acetylcholine Receptor, CD25, CA19-9 marker, CA-125 marker and MIS (Muellerian Inhibitory Substance) Receptor type II, sTn (sialylated Tn antigen; TAG-72), FAP (fibroblast activation antigen), endosialin, EGFRvlll, LG, SAS, PD-L1, CD47, SIRPa, and CD63.

In some embodiments, a bispecific antibody comprises a full-length human antibody, wherein a first antibody variable domain of the bispecific antibody is capable of recruiting the activity of a human immune effector cell by specifically binding to CD3, and wherein a second antibody variable domain of the heterodimeric protein is capable of specifically binding to a target antigen (e.g., CD20, EpCAM, or P-cadherin).

Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983).

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second immunoglobulin-like Fc region (e.g., a hinge region and/or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In another approach, the bispecific antibodies can be generated using a glutamine-containing peptide tag engineered to the antibody directed to an epitope (e.g., BCMA) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/162011/054899 (WO2012/059882).

In some embodiments, the first and second antibody variable domains of the bispecific antibody comprise amino acid modifications at positions wherein the first and second antibody variable domain of the bispecific antibody comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2.

In some embodiments, the first and second antibody variable domains of the bispecific antibody comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1.

In some embodiments, the first and second antibody variable domains of the bispecific antibody comprise amino acid modifications at positions 228 (e.g., (P228E or P228R)) in the hinge region and at position 409 or 368 (e.g., R409 or L368E (EU numbering scheme)) in the CH3 region of human IgG4.

In some embodiments, a bispecific may have any of the features or characteristics of any of the bispecific antibodies provided in WO2016166629, which is hereby incorporated by reference for all purposes.

Immune modulating agents include a variety of different molecule types which may stimulate an immune response in a subject, such as pattern recognition receptor (PRR) agonists, immunostimulatory cytokines, and cancer vaccines.

Pattern recognition receptors (PRRs) are receptors that are expressed by cells of the immune system and that recognize a variety of molecules associated with pathogens and/or cell damage or death. PRRs are involved in both the innate immune response and the adaptive immune immune response. PRR agonists may be used to stimulate the immune response in a subject. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein.

The terms "TLR" and "toll-like receptor" refer to any toll-like receptor. Toll-like receptors are receptors involved in activating immune responses. TLRs recognize, for example, pathogen-associated molecular patterns (PAMPs) expressed in microbes, as well as endogenous damage-associated molecular patterns (DAMPs), which are released from dead or dying cells.

Molecules which activate TLRs (and thereby activate immune responses) are referred to herein as "TLR agonists". TLR agonists can include, for example, small molecules (e.g. organic molecule having a molecular weight under about 1000 Daltons), as well as large molecules (e.g. oligonucleotides and proteins). Some TLR agonists are specific for a single type of TLR (e.g. TLR3 or TLR9), while some TLR agonists activate two or more types of TLR (e.g. both TLR7 and TLR8).

Exemplary TLR agonists provided herein include agonists of TLR2, TLR3, TLR4, TLR5, TLR6, TLR7, TLR8, and TLR9.

Exemplary small molecule TLR agonists include those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091,214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852.

Additional examples of small molecule TLR agonists include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-.beta.-D-ribofuranosylthiazolo[4,5-d]pyrimidine derivatives (such as those described in U.S. Publication No. 2003/0199461), and certain small molecule immuno-potentiator compounds such as those described, for example, in U.S. Patent Publication No. 2005/0136065.

Exemplary large molecule TLR agonists include as oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529, Mar. 5, 2004.

Other TLR agonists include biological molecules such as aminoalkyl glucosaminide phosphates (AGPs) and are described, for example, in U.S. Pat. Nos. 6,113,918; 6,303,347; 6,525,028; and 6,649,172.

TLR agonists also include inactivated pathogens or fractions thereof, which may activate multiple different types of TLR receptor. Exemplary pathogen-derived TLR agonists include BCG, *Mycobacterium obuense* extract, Talimogene laherparepvec (T-Vec) (derived from HSV-1), and Pexa-Vec (derived from vaccina virus).

In some embodiments, a TLR agonist may be an agonist antibody that binds specifically to the TLR.

Provided below are brief descriptions of various TLRs, as well as TLR agonists. The listing of a TLR agonist below for particular TLR should not be construed to indicate that a given TLR agonist necessarily only activates that TLR (e.g. certain molecules can activate multiple types of TLR, or even multiple classes of PRR). For example, some molecules provided below as an exemplary TLR4 agonist may also be a TLRS agonist.

The terms "TLR1" and "toll-like receptor 1" refer to any form of the TLR1 receptor, as well as variants, isoforms, and species homologs that retain at least a part of the activity of TLR1. Unless indicated differently, such as by specific reference to human TLR1, TLR1 includes all mammaila species of native sequence TLR1, e.g. human, monkey, and mouse. One exemplary human TLR1 is provided under UniProt Entry No. Q15399.

"TLR1 agonist" as used herein means, any molecule, which upon binding to TLR1, (1) stimulates or activates TLR1, (2) enhances, increases, promotes, induces, or prolongs an activity, function, or presence of TLR1, or (3) enhances, increases, promotes, or induces the expression of TLR1. TLR1 agonists useful in the any of the treatment methods, medicaments and uses of the present invention include, for example, bacterial lipoproteins and derivatives thereof which bind TLR1.

Examples of TLR1 agonists that are useful in the treatment methods, medicaments, and uses of the present invention include, for example, bacterial lipoproteins and derivatives thereof such as SPM-105 (derived from autoclaved mycobacteria), OM-174 (lipid A derivative), OmpS1 (porin from *Salmonella typhi*), OmpS1 (porin from *Salmonella typhi*), OspA (from *Borrelia burgdorferi*), MALP-2 (mycoplasmal macrophage-activating lipopeptide-2 kD), STF (soluble tuberculosis factor), CU-T12-9, Diprovocim, and lipopeptides derived from cell-wall components such as PAM2CSK4, PAM3CSK4, and PAM3Cys.

TLR1 can form a heterodimer with TLR2, and accordingly, many TLR1 agonists are also TLR2 agonists.

The terms "TLR2" and "toll-like receptor 2" refer to any form of the TLR2 receptor, as well as variants, isoforms, and species homologs that retain at least a part of the activity of TLR2. Unless indicated differently, such as by specific reference to human TLR2, TLR2 includes all mammilla species of native sequence TLR2, e.g. human, monkey, and mouse. One exemplary human TLR2 is provided under UniProt Entry No. 060603.

"TLR2 agonist" as used herein means, any molecule, which upon binding to TLR2, (1) stimulates or activates TLR2, (2) enhances, increases, promotes, induces, or prolongs an activity, function, or presence of TLR2, or (3) enhances, increases, promotes, or induces the expression of TLR2. TLR2 agonists useful in the any of the treatment methods, medicaments and uses of the present invention include, for example, bacterial lipoproteins and derivatives thereof which bind TLR2.

Examples of TLR2 agonists that are useful in the treatment methods, medicaments, and uses of the present invention include, for example, bacterial lipoproteins (e.g. diacylated lipoproteins) and derivatives thereof such as SPM-105 (derived from autoclaved mycobacteria), OM-174 (lipid A derivative), OmpS1 (porin from *Salmonella typhi*), OmpS1 (porin from *Salmonella typhi*), OspA (from *Borrelia burgdorferi*), MALP-2 (mycoplasmal macrophage-activating lipopeptide-2 kD), STF (soluble tuberculosis factor), CU-T12-9, Diprovocim, Amplivant, and lipopeptides derived from cell-wall components such as PAM2CSK4, PAM3CSK4, and PAM3Cys.

TLR2 can form a heterodimer with TLR1 or TLR6, and accordingly, many TLR2 agonists are also TLR1 or TLR6 agonists.

The terms "TLR3" and "toll-like receptor 3" refer to any form of the TLR3 receptor, as well as variants, isoforms, and species homologs that retain at least a part of the activity of TLR3. Unless indicated differently, such as by specific reference to human TLR3, TLR3 includes all mammaila species of native sequence TLR3, e.g. human, monkey, and mouse. One exemplary human TLR3 is provided under UniProt Entry No. 015455.

"TLR3 agonist" as used herein means, any molecule, which upon binding to TLR3, (1) stimulates or activates TLR3, (2) enhances, increases, promotes, induces, or prolongs an activity, function, or presence of TLR3, or (3) enhances, increases, promotes, or induces the expression of TLR3. TLR3 agonists useful in the any of the treatment method, medicaments and uses of the present invention include, for example, nucleic acid ligands which bind TLR3.

Examples of TLR3 agonists that are useful in the treatment methods, medicaments, and uses of the present invention include TLR3 ligands such as synthetic dsRNA, polyinosinic-polycytidylic acid ["poly(I:C)"] (available from, e.g. InvivoGen in high molecular weight (HMW) and low molecular weight (LMW) preparations), polyadenylic-polyuridylic acid ["poly(A:U)"] (available from, e.g. InvivoGen), polyICLC (see Levy et al., Journal of Infectious Diseases, vol. 132, no. 4, pp. 434-439, 1975), Ampligen (see Jasani et al., Vaccine, vol. 27, no. 25-26, pp. 3401-3404, 2009), Hiltonol, Rintatolimod, and RGC100 (see Naumann et al., Clinical and Developmental Immunology, vol. 2013, article ID 283649).

The terms "TLR4" and "toll-like receptor 4" refer to any form of the TLR4 receptor, as well as variants, isoforms, and species homologs that retain at least a part of the activity of TLR4. Unless indicated differently, such as by specific reference to human TLR4, TLR4 includes all mammilla species of native sequence TLR4, e.g. human, monkey, and mouse. One exemplary human TLR4 is provided under UniProt Entry No. O00206.

"TLR4 agonist" as used herein means, any molecule, which upon binding to TLR4, (1) stimulates or activates TLR4, (2) enhances, increases, promotes, induces, or prolongs an activity, function, or presence of TLR4, or (3) enhances, increases, promotes, or induces the expression of TLR4. TLR4 agonists useful in the any of the treatment methods, medicaments and uses of the present invention include, for example, bacterial lipopolysaccharides (LPS) and derivatives thereof which bind TLR4.

Examples of TLR4 agonists that are useful in the treatment methods, medicaments, and uses of the present invention include, for example, bacterial lipopolysaccharides (LPS) and derivatives thereof such as B:0111 (Sigma), monophosphoryl lipid A (MPLA), 3DMPL (3-O-deacylated MPL), GLA-AQ, G100, AS15, ASO2, GSK1572932A (GlaxoSmithKline, UK).

The terms "TLR5" and "toll-like receptor 5" refer to any form of the TLR5 receptor, as well as variants, isoforms, and species homologs that retain at least a part of the activity of TLR5. Unless indicated differently, such as by specific reference to human TLR5, TLR5 includes all mammaila species of native sequence TLR5, e.g. human, monkey, and mouse. One exemplary human TLR5 is provided under UniProt Entry No. O60602.

"TLR5 agonist" as used herein means, any molecule, which upon binding to TLR5, (1) stimulates or activates TLR5, (2) enhances, increases, promotes, induces, or prolongs an activity, function, or presence of TLR5, or (3) enhances, increases, promotes, or induces the expression of TLR5. TLR5 agonists useful in the any of the treatment methods, medicaments and uses of the present invention include, for example, bacterial flagellins and derivatives thereof which bind TLR5.

Examples of TLR5 agonists that are useful in the treatment methods, medicaments, and uses of the present invention include, for example, bacterial flagellin purified from *B. subtilis*, flagellin purified from *P. aeruginosa*, flagellin purified from *S. typhimurium*, and recombinant flagellin (all available from InvivoGen), entolimod (CBLB502, a pharmacologically optimized flagellin derivative).

The terms "TLR6" and "toll-like receptor 6" refer to any form of the TLR6 receptor, as well as variants, isoforms, and species homologs that retain at least a part of the activity of TLR6. Unless indicated differently, such as by specific reference to human TLR6, TLR6 includes all mammilla species of native sequence TLR6, e.g. human, monkey, and mouse. One exemplary human TLR6 is provided under UniProt Entry No. Q9Y2C9.

"TLR6 agonist" as used herein means, any molecule, which upon binding to TLR6, (1) stimulates or activates TLR6, (2) enhances, increases, promotes, induces, or prolongs an activity, function, or presence of TLR6, or (3) enhances, increases, promotes, or induces the expression of TLR6. TLR6 agonists useful in the any of the treatment methods, medicaments and uses of the present invention include, for example, bacterial lipopeptides and derivatives thereof which bind TLR6.

Examples of TLR6 agonists that are useful in the treatment methods, medicaments, and uses of the present invention include, for example, many of the TLR2 agonists provided above, as TLR2 and TLR6 can form a heterodimer. TLR6 can also form a heterodimer with TLR4, and TLR6 agonists can include various TLR4 agonists provided above.

The terms "TLR7" and "toll-like receptor 7" refer to any form of the TLR7 receptor, as well as variants, isoforms, and species homologs that retain at least a part of the activity of TLR7. Unless indicated differently, such as by specific reference to human TLR7, TLR7 includes all mammilla species of native sequence TLR7, e.g. human, monkey, and mouse. One exemplary human TLR7 is provided under UniProt Entry No. Q9NYK1.

"TLR7 agonist" as used herein means, any molecule, which upon binding to TLR7, (1) stimulates or activates TLR7, (2) enhances, increases, promotes, induces, or prolongs an activity, function, or presence of TLR7, or (3) enhances, increases, promotes, or induces the expression of TLR7. TLR7 agonists useful in the any of the treatment method, medicaments and uses of the present invention include, for example, nucleic acid ligands which bind TLR7.

Examples of TLR7 agonists that are useful in the treatment methods, medicaments, and uses of the present invention include recombinant single-stranded ("ss")RNA, imidazoquinoline compounds such as imiquimod (R837), gardiquimod, and resiquimod (R848); Loxoribine (7-allyl-7,8-dihydro-8-oxo-guanosine) and related compounds; 7-Thia-8-oxoguanosine, 7-deazaguanosine, and related guanosine analogs; ANA975 (Anadys Pharmaceuticals) and related compounds; SM-360320 (Sumimoto); 3M-01, 3M-03, 3M-852, and 3M-S-34240 (3M Pharmaceuticals); GSK2245035 (GlaxoSmithKline; an 8-oxoadenine molecule), AZD8848 (AstraZeneca; an 8-oxoadenine molecule), MEDI9197 (Medimmune; formerly 3M-052), ssRNA40, and adenosine analogs such as UC-1V150 (Jin et al., Bioorganic Medicinal Chem Lett (2006) 16:4559-4563, compound 4). Many TLR7 agonists are also TLR8 agonists.

The terms "TLR8" and "toll-like receptor 8" refer to any form of the TLR8 receptor, as well as variants, isoforms, and species homologs that retain at least a part of the activity of TLR8. Unless indicated differently, such as by specific reference to human TLR8, TLR8 includes all mammilla species of native sequence TLR8, e.g. human, monkey, and mouse. One exemplary human TLR8 is provided under UniProt Entry No. Q9NR97.

"TLR8 agonist" as used herein means, any molecule, which upon binding to TLR8, (1) stimulates or activates TLR8, (2) enhances, increases, promotes, induces, or prolongs an activity, function, or presence of TLR8, or (3) enhances, increases, promotes, or induces the expression of TLR8. TLR8 agonists useful in the any of the treatment method, medicaments and uses of the present invention include, for example, nucleic acid ligands which bind TLR8.

Examples of TLR8 agonists that are useful in the treatment methods, medicaments, and uses of the present invention include recombinant single-stranded ssRNA, imiquimod (R837), gardiquimod, resiquimod (R848), 3M-01, 3M-03, 3M-852, and 3M-S-34240 (3M Pharmaceuticals); GSK2245035 (GlaxoSmithKline; an 8-oxoadenine molecule), AZD8848 (AstraZeneca; an 8-oxoadenine molecule), MEDI9197 (Medimmune; formerly 3M-052), Poly-G10, Motolimod, and various TLR7 agonists provided above (as previously noted, many TLR7 agonists are also TLR8 agonists).

The terms "TLR9" and "toll-like receptor 9" refer to any form of the TLR9 receptor, as well as variants, isoforms, and species homologs that retain at least a part of the activity of TLR9. Unless indicated differently, such as by specific reference to human TLR9, TLR9 includes all mammilla species of native sequence TLR9, e.g. human, monkey, and mouse. One exemplary human TLR9 is provided under UniProt Entry No. Q9NR96.

"TLR9 agonist" as used herein means, any molecule, which upon binding to TLR9, (1) stimulates or activates TLR9, (2) enhances, increases, promotes, induces, or prolongs an activity, function, or presence of TLR9, or (3) enhances, increases, promotes, or induces the expression of TLR9. TLR9 agonists useful in the any of the treatment method, medicaments and uses of the present invention include, for example, nucleic acid ligands which bind TLR9.

Examples of TLR9 agonists that are useful in the treatment methods, medicaments, and uses of the present invention include unmethylated CpG-containing DNA, immunostimulatory oligodeoxynucleotides (ODN), such as CpG-containing ODN such as CpG24555, CpG10103, CpG7909 (PF-3512676/agatolimod), CpG1018, AZD1419, ODN2216, MGN1703, SD-101, 1018ISS, and CMP-001. TLR9 agonists also include nucleotide sequences containing a synthetic cytosine-phosphate-2'-deoxy-7-deazaguanosine dinucleotide (CpR) (Hybridon, Inc.), dSLIM-30L1, and immunoglobulin-DNA complexes. Exemplary TLR9 agonists are disclosed in WO2003/015711, WO2004/016805, WO2009/022215, PCT/US95/01570, PCT/US97/19791, and U.S. Pat. Nos. 8,552,165, 6,194,388 and 6,239,116, which are each hereby incorporated by reference for all purposes.

RLRs include various cytosolic PRRs that detect, e.g. dsRNAs. Examples of RLRs include, for example, retinoic acid-inducible gene I (RIG-I), melanoma differentiation-associated gene 5 (MDA-5), and Laboratory of Genetics and Physiology 2 (LGP2).

"RLR agonist" as used herein means, any molecule, which upon binding to an RLR, (1) stimulates or activates the RLR, (2) enhances, increases, promotes, induces, or prolongs an activity, function, or presence of the RLR, or (3) enhances, increases, promotes, or induces the expression of RLR. RLR agonists useful in the any of the treatment methods, medicaments and uses of the present invention include, for example, nucleic acids and derivatives thereof which bind RLRs and agonistic monoclonal antibodies (mAb) which specifically binds to RLRs.

Examples of RLRs agonists that are useful in the treatment methods, medicaments, and uses of the present invention include, for example, short double-stranded RNA with uncapped 5' triphosphate (RIG-I agonist); poly I:C (MDA-5 agonist), and BO-112 (MDA-A agonist).

NLRs include various PRRs that detect, e.g. damage-associated molecular pattern (DAMP) molecules. NLRs include the subfamilies NLRA-A, NLRB-B, NLRC-C, and NLRP-P. Examples of NLRs include, for example, NOD1, NOD2, NAIP, NLRC4, and NLRP3.

"NLR agonist" as used herein means, any molecule, which upon binding to an NLR, (1) stimulates or activates the NLR, (2) enhances, increases, promotes, induces, or prolongs an activity, function, or presence of the NLR, or (3) enhances, increases, promotes, or induces the expression of NLR. NLR agonists useful in the any of the treatment methods, medicaments and uses of the present invention include, for example, DAMPs and derivatives thereof which bind NLRs and agonistic monoclonal antibodies (mAb) which specifically binds to NLRs.

Examples of NLR agonists that are useful in the treatment methods, medicaments, and uses of the present invention include, for example, liposomal muramyl tripeptide/mifamurtide (NOD2 agonist).

CLRs include various PRRs that detect, e.g. carbohydrates and glycoproteins. CLRs include both transmembrane CLRs and secreted CLRs. Examples of CLRs include, for example, DEC-205/CD205, macrophage mannose receptor (MMR), Dectin-1, Dectin-2, mincle, DC-SIGN, DNGR-1, and mannose-binding lectin (MBL).

"CLR agonist" as used herein means, any molecule, which upon binding to a CLR, (1) stimulates or activates the CLR, (2) enhances, increases, promotes, induces, or prolongs an activity, function, or presence of the CLR, or (3) enhances, increases, promotes, or induces the expression of CLR. CLR agonists useful in the any of the treatment methods, medicaments and uses of the present invention include, for example, carbohydrates and derivatives thereof which bind CLRs and agonistic monoclonal antibodies (mAb) which specifically binds to CLRs.

Examples of CLR agonists that are useful in the treatment methods, medicaments, and uses of the present invention include, for example, MD-fraction (a purified soluble betaglucan extract from *Grifola frondosa*) and imprime PGG (a beta 1,3/1,6-glucan PAMP derived from yeast).

The STING protein functions as both a cytosolic DNA sensor and an adaptor protein in Type 1 interferon signaling. The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammilla species of native sequence STING, e.g. human, monkey, and mouse. One exemplary human TLR9 is provided under UniProt Entry No. Q86WV6. STING is also known as TMEM173.

"STING agonist" as used herein means, any molecule, which upon binding to TLR9, (1) stimulates or activates STING, (2) enhances, increases, promotes, induces, or prolongs an activity, function, or presence of STING, or (3) enhances, increases, promotes, or induces the expression of STING. STING agonists useful in the any of the treatment method, medicaments and uses of the present invention include, for example, nucleic acid ligands which bind STING.

Examples of STING agonists that are useful in the treatment methods, medicaments, and uses of the present invention include various immunostimulatory nucleic acids, such as synthetic double stranded DNA, cyclic di-GMP, cyclic-GMP-AMP (cGAMP), synthetic cyclic dinucleotides (CDN) such as MK-1454 and ADU-S100 (MIW815), and small molecules such as P0-424.

Other PRRs include, for example, DNA-dependent Activator of IFN-regulatory factors (DAI) and Absent in Melanoma 2 (AIM2).

Immunostimulatory cytokines include various signaling proteins that stimulate immune response, such as interferons, interleukins, and hematopoietic growth factors.

Exemplary immunostimulatory cytokines include GM-CSF, G-CSF, IFN-alpha, IFN-gamma; IL-2 (e.g. denileukin difitox), IL-6, IL-7, IL-11, IL-12, IL-15, IL-18, IL-21, and TNF-alpha.

Immunostimulatory cytokines may have any suitable format. In some embodiments, an immunostimulatory cytokine may be a recombinant version of a wild-type cytokine. In some embodiments, an immunostimulatory cytokine may be a mutein that has one or more amino acid changes as compared to the corresponding wild-type cytokine. In some embodiments, an immunostimulatory cytokine may be incorporated into a chimeric protein containing the cytokine and at least one other functional protein (e.g. an antibody). In some embodiments, an immunostimulatory cytokine may covalently linked to a drug/agent (e.g. any drug/agent as described elsewhere herein as a possible ADC component).

Cancer vaccines include various compositions that contain tumor associated antigens (or which can be used to generate the tumor associated antigen in the subject) and thus can be used to provoke an immune response in a subject that will be directed to tumor cells that contain the tumor associated antigen.

Example materials that may be included in a cancer vaccine include, attenuated cancerous cells, tumor antigens, antigen presenting cells such as dendritic cells pulsed with tumor derived antigen or nucleic acids encoding tumor associated antigens. In some embodiments, a cancer vaccine may be prepared with a patient's own cancer cells. In some embodiments, a cancer vaccine may be prepare with biological material that is not from a patient's own cancer cells.

Cancer vaccines include, for example, sipuleucel-T and talimogene laherparepvec (T-VEC).

Immune cell therapy involves treating a patient with immune cells that are capable of targeting cancer cells. Immune cell therapy includes, for example, tumor-infiltrating lymphocytes (TILs) and chimeric antigen receptor T cells (CAR-T cells).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g., calicheamicin, especially calicheamicin gamma1I and calicheamicin phill, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"), cyclophosphamide; thiotepa;

taxoids, e.g., paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; KRAS inhibitors; MCT4 inhibitors; MAT2a inhibitors; tyrosine kinase inhibitors such as sunitinib, axitinib, alk/c-Met/ROS inhibitors such as crizotinib, lorlatinib; mTOR inhibitors such as temsirolimus, gedatolisib; src/abl inhibitors such as bosutinib; cyclin-dependent kinase (CDK) inhibitors such as palbociclib, PF-06873600; erb inhibitors such as dacomitinib; PARP inhibitors such as talazoparib; SMO inhibitors such as glasdegib, PF-5274857; EGFR T790M inhibitors such as PF-06747775; EZH2 inhibitors such as PF-06821497; PRMT5 inhibitors such as PF-06939999; TGFRβr1 inhibitors such as PF-06952229; and pharmaceutically acceptable salts, acids or derivatives of any of the above. In specific embodiments, such additional therapeutic agent is bevacizumab, cetuximab, sirolimus, panitumumab, 5-fluorouracil (5-FU), capecitabine, tivozanib, irinotecan, oxaliplatin, cisplatin, trifluridine, tipiracil, leucovorin, gemcitabine, regorafinib or erlotinib hydrochloride.

In some embodiments, an antibody is used in conjunction with one or more other therapeutic agents targeting an immune checkpoint modulator or costimulatory agent, such as, for example without limitation, an agent targeting CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITR, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CXCR4, CCR4, CCR8, CCR5, CSF-1, or an innate immune response modulator.

In some embodiments, an antibody is used in conjunction with, for example, an anti-CTLA-4 antagonist antibody such as for example ipilimumab; an anti-LAG-3 antagonist antibody such as BMS-986016 and IMP701, an anti-TIM-3 antagonist antibody; an anti-B7-H3 antagonist antibody such as for example MGA271; an-anti-VISTA antagonist antibody; an anti-TIGIT antagonist antibody; antibody; an anti-CD80 antibody; an anti-CD86 antibody; an-anti-B7-H4 antagonist antibody; an anti-ICOS agonist antibody; an anti-CD28 agonist antibody; an innate immune response modulator (e.g., TLRs, KIR, NKG2A), and an IDO inhibitor.

In some embodiments, an antibody is used in conjunction with an OX40 agonist such as, for example, an anti-OX-40 agonist antibody. In some embodiments, an antibody is used in conjunction with a GITR agonist such as, for example, an-anti-GITR agonist antibody such as, for example without limitation, TRX518. In some embodiments, an antibody is used in conjunction with an IDO inhibitor. In some embodiments, an antibody is used in conjunction with a cytokine therapy such as, for example without limitation, IL-15, CSF-1, MCSF-1, etc.

In some embodiments, an antibody is used in conjunction with one or more other therapeutic antibodies, such as, for example without limitation, an antibody targeting CD19, CD22, CD40, CD52, or CCR4.

In certain embodiments, an antibody composition comprises at least one additional agent such as bevacizumab, cetuximb, sirolimus, panitumumab, 5-fluorouracil (5-FU), capecitabine, tivozanib, irinotecan, oxaliplatin, cisplatin, trifluridine, tipiracil, leucovorin, gemcitabine and erlotinib hydrochloride.

In some embodiments, the antibody therapy may be co-administered with, or be sequentially administered before or after the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an antibody of the present invention is combined with a treatment regimen further comprising a traditional therapy selected from the group consisting of: surgery, radiation therapy, chemotherapy, targeted therapy, immunotherapy, hormonal therapy, angiogenesis inhibition and palliative care.

The composition used in the present invention can further comprise pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

In one aspect, the present invention provides a method of producing an antibody as disclosed herein, comprising culturing a host cell, under conditions that results in production of an antibody as disclosed herein, and purifying the antibody or the bispecific antibody from the culture.

In another aspect, the present invention provides a use of an antibody, a pharmaceutical composition, a polynucleotide, a vector, ora host cell as disclosed herein, in the manufacture of a medicament for detecting, diagnosing, and/or treating a tumor antigen associated disorder.

Diagnostic Use

In one aspect, the CD3 antibodies of the present invention may be used to detect and/or measure CD3, or CD3-expressing cells in a sample, e.g., for diagnostic purposes. For example, the CD3 antibody may be used to diagnose a condition or disease characterized by aberrant expression (e.g., over-expression, under-expression, lack of expression, etc.) of CD3. Exemplary diagnostic assays for CD3 may comprise, e.g., contacting a sample, obtained from a subject, with CD3 antibody of the invention, wherein the CD3 antibody is labeled with a detectable label or reporter molecule. Alternatively, an unlabeled CD3 antibody can be used in diagnostic applications in combination with a secondary antibody which is itself detectably labeled. The detectable label or reporter molecule can be a radioisotope, such as $^{14}C$, $^{3}H$, $^{125}I$, $^{32}P$, or $^{35}S$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure CD3 in a sample includes, but is not limited to enzyme-linked immunosorbent assay (ELISA), radioimmunoassay (RIA), fluorescence-activated cell sorting (FACS), and the like. Samples that can be used in CD3 diagnostic assays according to the present invention include any tissue or fluid sample obtainable from a patient which contains detectable quantities of CD3 protein, or fragments thereof, under normal or pathological conditions. Generally, levels of CD3 in a particular sample obtained from a healthy patient (e.g., a patient not afflicted with a disease or condition associated with abnormal CD3 levels or activity) will be measured to initially establish a baseline, or standard, level of CD3. This baseline level of CD3 can then be compared against the levels of CD3 measured in samples obtained from individuals suspected of having a CD3 related disease or condition.

In another aspect, provided is a method of detecting, diagnosing, and/or monitoring a condition associated with a tumor antigen expression. For example, the multispecific antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

Kits

A further aspect of the invention is a kit comprising an antibody as disclosed hereinabove and instructions for use in accordance with any of the methods of the invention described herein. Generally, these instructions comprise a description of administration of the antibody for the above described therapeutic treatments. This kit comprises any pharmaceutical composition disclosed herein. The pharmaceutical compositions and other reagents may be present in the kits in any convenient form, such as, e.g., in a solution or in a powder form.

In another aspect, a kit further comprises one or more other prophylactic or therapeutic agents useful for the treatment of cancer, in one or more containers. In one embodiment, the other prophylactic or therapeutic agent is a chemotherapeutic. In other aspects, the prophylactic or therapeutic agent is a biological or hormonal therapeutic.

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans.

Toxicity and efficacy of the prophylactic and/or therapeutic protocols of the instant invention maybe determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Prophylactic and/or therapeutic agents that exhibit large therapeutic indices are preferred.

Further, any assays known to those skilled in the art may be used to evaluate the prophylactic and/or therapeutic utility of the therapies or combinatorial therapies disclosed herein for treatment or prevention of cancer.

The instructions relating to the use of the bispecific antibody as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, ampules, tubes, bottles, jars, flexible packaging (e.g., sealed Mylar or plastic bags), and the like for each pharmaceutical composition and other included reagents, e.g., buffers, balanced salt solutions, etc., for use in administering the pharmaceutical compositions to subjects. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody. The container may further comprise a second pharmaceutically active agent.

Normally, the kit comprises a container and a label or package insert(s) on or associated with the container.

Biological Deposits

Representative materials of the present invention were deposited in the American Type Culture Collection (ATCC), 10801 University Boulevard, Manassas, Va. 20110-2209, USA, on 13, February 2018. Vector GUCY2C-1608 Chain A (VH-Hole SEQ ID NO: 94) having ATCC Accession No. PTA-124943 comprises a DNA insert encoding the VH-Hole chain of bispecific antibody GUCY2C-1608, which comprises a polynucleotide (SEQ ID NO: 70) encoding a CD3 antibody light chain variable region (SEQ ID NO: 3); and vector GUCY2C-1608 Chain B (VL-Knob SEQ ID NO: 93) having ATCC Accession No. PTA-124944 comprises a DNA insert encoding the VL-Knob chain of bispecific antibody GUCY2C-1608, which comprises a polynucleotide (SEQ ID NO: 71) encoding a CD3 antibody heavy chain variable region (SEQ ID NO: 4).

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions; the materials will be promptly replaced on notification with another of the same. Availability of the deposited material is not to be construed as a license to practice the invention in contravention of the rights granted under the authority of any government in accordance with its patent laws.

The following examples of specific aspects for carrying out the present invention are offered for illustrative purposes only, and are not intended to limit the scope of the present invention in any way.

Example 1

Generation of Soluble CD3ed

Protein by name CD3ed representing extracellular domains of CD3 epsilon and delta subunits fused in tandem via a short linker (SEQ ID NO: 39) was generated using standard molecular biology, protein expression and purification techniques. The plasmid bearing gene that codes for the amino acid shown in Table 9 (SEQ ID NO: 40) was transiently transfected in HEK293 cells in 20 L culture volume using PEI as transfection agent. Following incubation for 7 days at 37C, 20 L of harvest was batch bound to 50 ml of His60 resin (equilibrated with PBS) overnight. Then the bound resin was washed with PBS followed by 10 mM imidazole containing PBS buffers (10-15 CV). After washing, the protein was eluted with 200 mM of imidazole containing Phosphate Buffer. The eluate fractions were then analyzed by SDS gel. The fractions containing pure protein were pooled together and concentrated using 3 kDa Amicon ultra centricons. 5% Glycerol was maintained in the sample at the time of concentration to keep the protein stable. The His60 pool is further loaded onto the size exclusion Superdex200 column. Fractions containing CD3 epsilon/delta heterodimer were analyzed by SDS-PAGE and relevant fractions were pooled and 0.22 µm filtered. Table 9 shows the sequence of the CD3 epsilon/delta subunits fused in tandem and used as antigen for all the optimization work.

TABLE 9

| SEQ ID NO: | Protein | Sequence |
| --- | --- | --- |
| 40 | CD3 epsilon/delta fusion protein | MQSGTHWRVLGLCLLSVGVWGQDGNEEMGG ITQTPYKVSISGTTVILTCPQYPGSEILWQHNDK NIGGDEDDKNIGSDEDHLSLKEFSELEQSGYY VCYPRGSKPEDANFYLYLRARGGGGSGGGG SGGGGSPIEELEDRVFVNCNTSITWVEGTVGT LLSDITRLDLGKRILDPRGIYRCNGTDIYKDKES TVQVHYRMCQSCVELDHHHHHH |

Example 2

Framework Optimization of CD3 Antibody H2B4

Lead CD3e (CD3 epsilon) antibody H2B4 exhibited lower thermal stability when used in bispecific diabody-Fc format. To improve the stability, the light chain framework was changed from VK4 to VK1 (DPK9) while leaving the heavy chain framework as VH3 (DP54). The VL CDR1 (SEQ ID NO: 26), VL CDR2 (SEQ ID NO: 27) and VL CDR3 (SEQ ID NO: 28) were grafted onto DPK9 framework and expressed in combination with the heavy chain bearing CDRs, VH CDR1 (SEQ ID NO: 13), VH CDR2 (SEQ ID NO: 16), and VH CDR3 (SEQ ID NO: 18). In addition to grafting CDRs into frame works, certain back mutations were also tested. The back mutations introduced in both heavy and light chain frameworks are shown in Table 10 with residue number at which back mutation was performed indicated.

The cDNAs containing human acceptor framework, VH3 for heavy chain and VK1 for light chain, with relevant CDR donor sequences were synthesized. Synthesized cDNA products were subcloned and fused in frame with human IgG1 constant region for the heavy chain, and human kappa for the light chain in mammalian expression vectors. To differentiate from H2B4 antibody, these variants are called 2B5 and all the optimized molecules will be referred to as 2B5 and its variants here after. All the 2B5 mutants were analyzed for competitive binding to Jurkat cells with endogenous expression of CD3e.

A competition FACS was performed to examine whether humanized 2B5 maintained its binding epitope on cell surface. Prior to the competition FACS experiment, chimeric cH2B4 was biotinylated. The EC50 of the binding of biotinylated cH2B4 to Jurkat cells was determined by direct binding using FACS and determined to be 0.8 nM. For the competition FACS, 3-fold serially diluted antibody variants were mixed with a constant amount of biotin-cH2B4 representing EC50 concentration and 1.0+E05 cell/well of Jurkat cells. The mixtures were incubated for 1 hour on ice followed by 3× washing with FACS buffer. The secondary antibody, PE (phycoerythrin) conjugated streptavidin (PE-SA) was added to the cells and incubated for 30 minutes on ice. Median fluorescence intensity (MFI) was then analyzed by FACS on a FACS CANTO™ (BD Biosciences). Y axis calculation: % binding to Max=[MFI (serial diluted Ab wells)−MFI (2nd PE-SA)]/[MFI max (Jurkat cells with biotin-cH2B4 only)-MFI (2nd PE-SA)]. Table 10 shows the result of $IC_{50}$ values of competition binding when mutations were introduced in CD3 antibody H2B4 to optimize the frameworks. Based on these results, H2B4 1.0/1.0T showed binding characteristics similar to H2B4 and is designated as CD3 antibody binding domain 2B5.

TABLE 10

| Antibody | Heavy Chain | Light Chain | $IC_{50}$ of competition binding |
|---|---|---|---|
| h264 1.0/1.0T (2B5) | CDR graft | CDR graft, R24T | 1.27 |
| h2B4 1.0/1.1 | vH1.0 | Q13V, R24T, Y49S, L78V | 1.68 |
| h2B4 1.0/1.2 | vH1.0 | Q13V, R24T, Y49S | Not tested |
| h2B4 1.0/1.3 | vH1.0 | R24T, Y49S | 1.309 |
| c2B4 (chimeric 2B4) | Mouse vH | Mouse vK | 0.752 |

Example 3

Generation and Characterization of a Bispecific Diabody-Fc Molecule Using H2B4 and 2B5 Sequences Bispecific diabody-Fc molecules were generated using CD3 antibodies 2B5 or H2B4 (Table 2 and 3) and GUCY2c antibody sequences in one of the configurations shown in FIG. 1 (schematic) using standard expression and purification techniques known in the art. The resulting bispecific antibodies (Table 7; SEQ.ID.NO.36-38) were tested for stability using differential scanning calorimetry.

Example 4

Stability Assessment of Bispecific Using Differential Scanning Calorimetry

Figure 2:
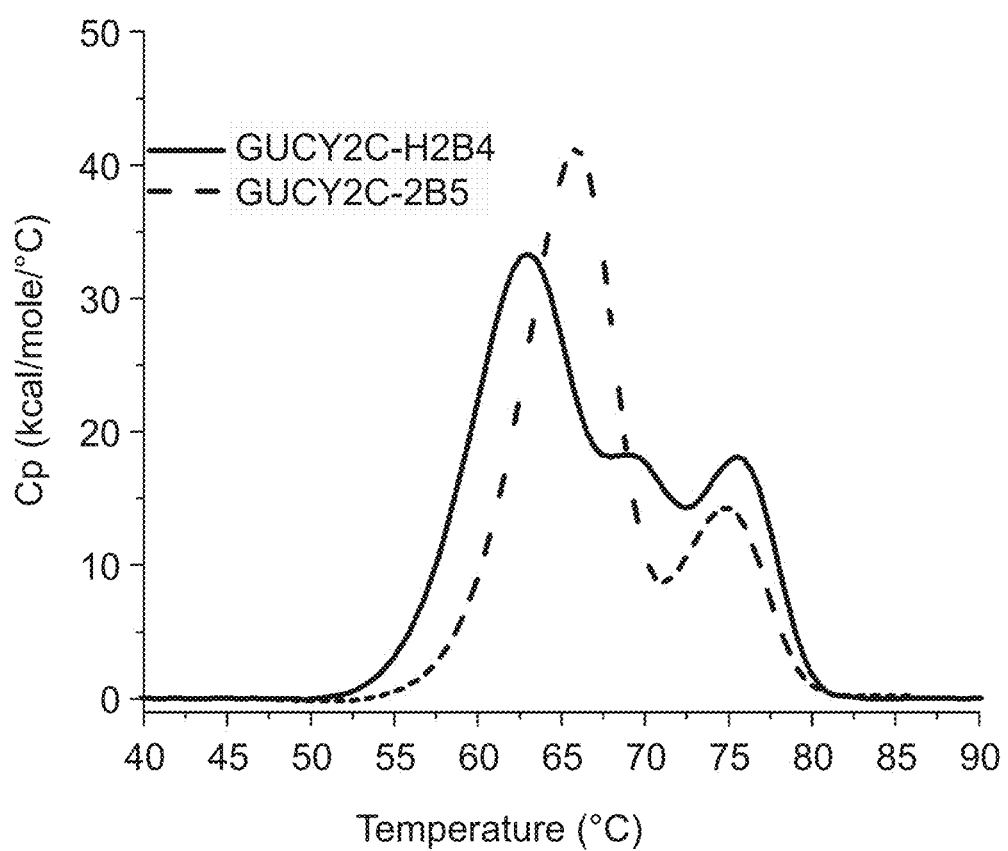
FIG. 2 depicts the results of differential scanning calorimetry thermograms showing heat capacity of GUCY2c-H2B4 and GUCY2c-2B5 bispecific antibodies as a function of temperature.

Proteins were diluted in a phosphate-buffered saline (PBS) solution to 0.6 mg/ml in a volume of 400 μl. PBS was used as a buffer blank in the reference cell. PBS contained 137 mM NaCl, 2.7 mM KCl, 8.1 mM Na2HPO4, and 1.47 mM KH2PO4, pH 7.2. Samples were dispensed into the sample tray of a MicroCal VP-Capillary DSC with Autosampler (Malvern Instruments Ltd, Malvern, UK). Samples were equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions. As illustrated in the FIG. 2, GUCY2c-2B5 bispecific showed 5° C. improved first melting transition compared to GUCY2c-H2B4 bispecific. This indicates that 2B5 containing bispecific antibodies exhibit better stability.

Figure 3:
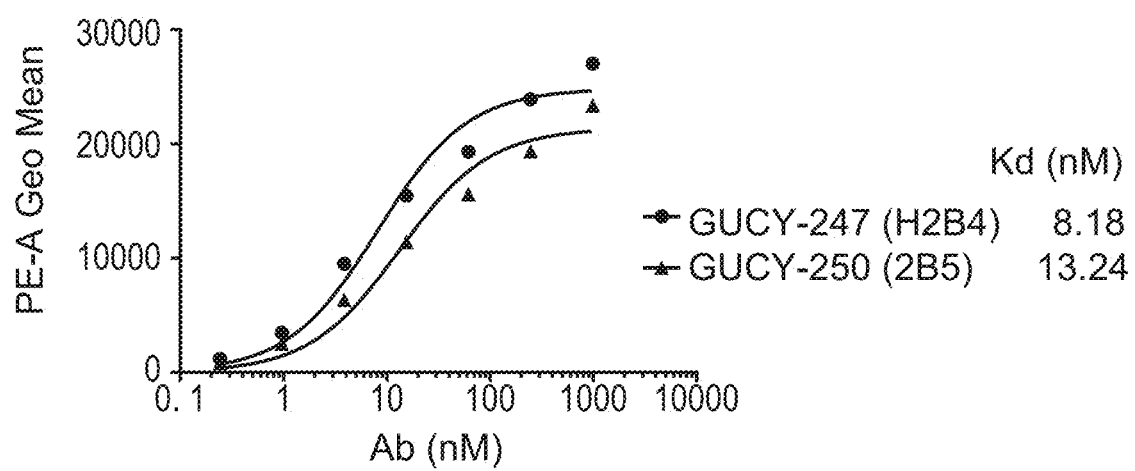
FIG. 3 depicts binding of GUCY2c-H2B4 (GUCY2c-0247) and GUCY2c-2B5 (GUCY2c-0250) bispecific antibodies to naïve human T cells using flow cytometry assay.

The two bispecific antibodies were checked for binding to T cells using FACS employing standard procedures known in the art and as shown in FIG. 3, both bispecific antibodies showed similar binding to T cells indicating that the binding is preserved upon conversion of H2B4 to 2B5.

Figure 4:
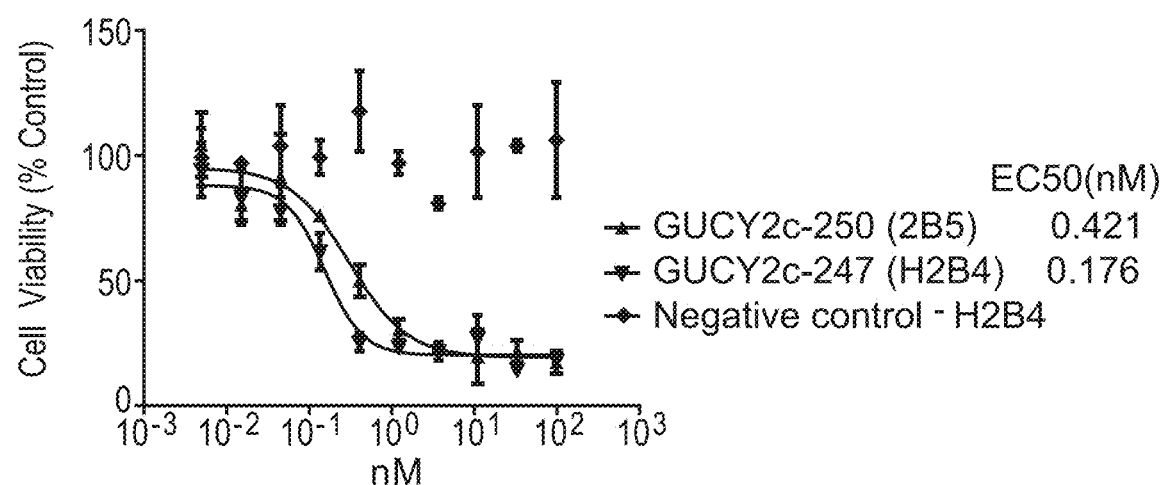
FIG. 4 depicts results of in vitro cytotoxicity mediated by GUCY2c-H2B4 (GUCY2c-0247) and GUCY2c-2B5 (GUCY2c-0250) bispecific antibodies using cell viability data.

Both H2B4 and 2B5 bispecific antibodies were also tested in cytotoxicity assay to assess T cell redirection activity. As shown in FIG. 4, both bispecific antibodies showed similar cytotoxicity indicating that 2B5 retained the same activity as H2B4.

Example 5

Structure-Based Rational Mutagenesis of 2B5

CD3 antibody H2B4 binding domain showed polyreactivity as assessed by binding to DNA and insulin, showed self-association propensity as indicated by high AC-SINS scores and has clipping propensity at R53 position in CDR-H2 when expressed in CHO host cells. To reduce polyreactivity, self-association propensity and clipping in CDRH2, Mutations in the CDRs of 2B5 were engineered to reduce these liabilities while maintaining the binding affinity and stability. For this effort, all the predictions were made using the CD3 antibody H2B4 x-ray crystal structure obtained in complex with the peptide representing the binding epitope and derived from N-terminus of CD3 epsilon subunit. It is well known in the field that excess positive charge and/or hydrophobicity could play a major role in the polyreactivity. The DelPhi Poisson Boltzmann calculator in Discovery Studio 4.0[1] was used to determine the electrostatic surface of the H2B4 Fv region from the crystal structure. In FIG. 5, excess positive charge patches that are not broken up by negative charges could be observed. This suggests correlation with high polyreactivity. Additionally, Spatial Aggregation Propensity (SAP) tool in Discovery Studio[1] was used to determine excessive hydrophobic patches (FIG. 6). As shown in the FIG. 6, the hydrophobic patch appears small and not substantial. Based upon this observation, the focus was shown on reduction of positive charges by either removing positive charges or adding negative charges to break up the patches.

To determine suitable positions for mutagenesis, computational prediction of mutations for both the changes in affinity and changes in stability were made using Discovery Studio and FoldX. Tolerated mutations are those that are not predicted to have a ΔΔG>1 kcal/mol for both the Discovery Studio and FoldX methods. From these predictions, a set of residues that would be predicted have the least impact on binding and stability while still breaking up the change patches were identified. In addition, we favored hydrophilic mutations where possible to not increase the hydrophobic surface. A list of possible CDR mutations introduced in CD3 antibody 2B5 to optimize the biophysical properties is shown in Table 11. This includes mutations that are predicted to be tolerated at each position and reduce polyreactivity and clipping.

TABLE 11

| Residue# relative to 2B5-0001 (kabat) | WT amino acid | Amino acids mutated to |
|---|---|---|
| Heavy chain | | |
| H52 | R | Q |
| H52B | R | Q |

TABLE 11-continued

| Residue# relative to 2B5-0001 (kabat) | WT amino acid | Amino acids mutated to | | |
|---|---|---|---|---|
| H53 | R | Q | L | E |
| H65 | K | Q | | |
| H96 | R | Q | | |
| Light chain | | | | |
| L27F | R | T | S | |
| L29 | R | Q | N | |
| L30 | K | Q | | |

In addition, a set of multiple mutations (in combination) was also designed for heavy chain and light chain. These include R52Q/R52bQ/R53Q, R52Q/R52bQ/R53Q/R96Q, R52bQ/R53Q/R96Q, and R52Q/R52bQ/R96Q for heavy chain and R29Q/K30Q/R54L/V27eE, R29Q_R54L_V27eE, R29Q_K30Q_R54L for light chain.

Example 6

Characterization of Mutants

All the mutants were generated as IgG molecules using standard expression and purification techniques well known in the art and tested for binding to CD3ed, polyreactivity (binding to DNA and insulin) and AC-SINS.

Binding Assays to Assess the Variants

An Octet assay was designed and run to examine both binding and dissociation rate at 10 ug/ml of soluble human CD3ed antigen (SEQ ID NO: 40). Anti-human IgG tips were used to capture the anti-CD3 antibodies at a concentration of 10 ug/ml for 120s, followed by a baseline in PBS for 30s, then dipped into the 10 ug/ml concentration of soluble human CD3ed antigen in for 120s, and finally dissociated in for 300s. Sensorgrams were examined to determine whether or not the antigen bound to the antibody and the Octet software was used to calculate the kd (1/s) and kd error. Twenty-six rational mutations retained binding to hCD3ed antigen. Kinetics of binding to soluble CD3 for the twenty-six CD3 antibody variants that still bound antigen were then examined by SPR, using Biacore analysis. The CD3 antibodies were captured on anti-human Fc and 0, 3.7, 11.1, 33.3 and 100 nM concentrations of soluble CD3 antigen was injected over the captured antibodies to determine the kinetics of binding. Twenty-three CD3 antibodies bound to soluble CD3 antigen with similar affinity as the CDR grafted parent antibody.

DNA and Insulin ELISA to Measure Polyreactivity 384-well ELISA plates (Nunc Maxisorp) were coated overnight at 4° C. with DNA (10 µg/ml) (Sigma-Aldrich, D1626) and insulin (5 µg/ml) (Sigma-Aldrich, 19278-5 mL) in PBS pH 7.5. The ELISA, adapted from assays described in Tiller et al (17), was carried out on a PerkinElmer Janus Automated Workstation liquid handling robot. Wells were washed with water, blocked with 50 µl of Polyreactivity ELISA Buffer (PEB; PBS containing 0.05% Tween-20, 1 mM EDTA) for 1 hour at room temperature, and rinsed three times with water. Serially-diluted mAbs in 25 ul were added in quadruplicate to the wells and incubated for 1 h at room temperature. Plates were washed three times with water, and 25 µl of 10 ng/ml goat anti-human IgG (Face fragment specific) conjugated to horseradish peroxidase (Jackson ImmunoResearch, 109-035-008) were added to each well. Plates were incubated for 1 h at room temperature, washed three times with 80 µl of water, and 25 µl of TMB substrate (Sigma-Aldrich, T-0440) added to each well. Reactions were stopped after approximately 7 minutes by adding 25 µl of 0.18 M ortho-phosphoric acid to each well and absorbance read at 450 nm. DNA- and insulin-binding scores were calculated as the ratio of the ELISA signal of the antibody at 10 µg/ml to the signal of a well containing buffer instead of the primary antibody. Scores of less than 8 were deemed ideal and represented low polyreactivity.

AC-SINS Assay to Measure Self-Association Propensity

AC-SINS (Affinity Capture Self-interaction Nanoparticle Spectroscopy) assay was standardized in a 384-well format on a Perkin-Elmer Janus liquid handling robot. 20 nm gold nanoparticles (Ted Pella, Inc., #15705) were coated with a mixture of 80% goat anti-human Fc (Jackson ImmunoResearch Laboratories, Inc. #109-005-098) and 20% non-specific goat polyclonal antibodies (Jackson ImmunoResearch Laboratories, Inc. #005-000-003) that were buffer exchanged into 20 mM sodium acetate pH 4.3 and diluted to 0.4 mg/ml. After one hour incubation at room temperature, sites unoccupied on the gold nanoparticles were blocked with thiolated polyethylene glycol (2 kD). The coated nanoparticles were then concentrated 10-fold using a syringe filter and 10 µl were added to 100 µl of mAb at 0.05 mg/ml in PBS pH 7.2. The coated nanoparticles were incubated with the antibody of interest for 2 hrs in a 96-well polypropylene plate and then transferred to a 384-well polystyrene plate and read on a Tecan M1000 spectrophotometer. The absorbance was read from 450-650 in 2 nm increments, and a Microsoft Excel macro was used to identify the max absorbance, smooth the data, and fit the data using a second-order polynomial. The smoothed max absorbance of the average blank (PBS buffer alone) was subtracted from the smoothed max absorbance of the antibody sample to determine the antibody AC-SINS score. Scores of less than 8 were deemed ideal and represented low degree of self-association.

Assessment of Lead CD3 Antibody 2B5 Variants in Diabody-Fc Bispecific Format

Comprehensive analysis of data from binding assays, AC-SINS and polyreactivity helped narrow down the binding variants to five which were reformatted to bispecific diabody-Fc molecules using an anti-tumor sequences and using standard cloning strategies well known in the art. These bispecific antibodies were transiently expressed and purified using the standard techniques well known in the art. The resulting bispecific antibodies were tested for binding to jurkat cells, in vitro cytotoxicity using T-cell retargeting assay, polyreactivity, thermal stability using DSC and AC-SINS. Of all the five bispecific antibodies, only one bispecific bearing the CD3 antibody 2B5 variant 2B5v6 showed potent binding and as a result showed potent cytotoxicity. This variant also showed reduced polyreactivity as assessed by DNA and insulin binding and AC-SINS score. The scores for 2B5v6 bispecific antibodies were less than 8 compared to greater than 8 for H2B4 bispecific antibodies. Based on these results, 2B5v6 was chosen as the lead optimized 2B5 variant for further analysis.

Example 7

Assessment of Clipping in CDR-H2

Clipping in VH CDR2 (SEQ ID NO: 16) at position R53 was observed in CD3 antibody (H2B4 and 2B5) when the bispecific is expressed in CHO cells but not in HEK293 cells. To derisk this liability and ensure better homogeneity in the product at a manufacturing scale, attention was paid to choose mutations in the clipping region along with other mutations to derisk other liabilities as described in the preceding examples. To assess the clipping, briefly diabody-Fc bispecific antibodies were generated using a negative control antibody variable domain sequence and CD3 antibody 2B5 or CD3 antibody H2B4 or CD3 antibody 2B5v6. All the bispecific diabody-Fc molecules were prepared using a similar schematic of expression and purification processes well known in the art. CHO SSI cell lines were generated using standard procedures. The two chains coding for bispecific antibody were cloned into the mammalian expression vector pRY19-GA-Q containing a dual promoter and recombination site for single-site integration (SSI) (Zhang, L. et al. Biotechnology Progress. 2015; 31: 1645-1656) into the CHO cell genome. The resulting plasmid was transfected into CHO-K1 SV 10e9 cells via electroporation with the pRY19 vector containing the gene of interest followed by positive and negative selection pressure using hygromycin-B and ganciclovir. These CHO pools went through a 3 week recovery phase. When observed viabilities were in excess of 90%, cell banks were generated for future work. The established CHO-pools were then subjected to a 12-day fed-batch platform expression process in CD-CHO media (ThermoFisher Scientific, Waltham, Mass.) at 1 L scale. Day 12 culture harvests were captured on a protein A column and eluted at low pH. The proA pool was immediately neutralized to pH 8.1. The resulting pure proteins were assessed using capillary gel electrophoresis (cGE) using standard protocols well known in the art. As shown in Table 12 and FIG. 7, 2B5 bispecific antibody showed much reduced clipping compared to H2B4, and 2B5v6 showed no clipping while H2B4 showed significantly increased clipping or fragmentation. Table 12 shows results of capillary gel electrophoresis showing fragmentation of CD3-GUCY2c bispecific antibodies. The % POI indicates peak-of-interest.

TABLE 12

| Reduced cGE sample | % POI | % Fragmentation |
| --- | --- | --- |
| Negative control-H264 | 88.8 | 11.2 |
| Negative control-2B5 | 98.9 | 1.1 |
| Negative control-2B5v6 | 99.6 | 0.4 |

Example 8

GUCY2c-2B5v6 Bispecific Antibodies: Expression and Purification of Chimeric CD3-GUCY2c Bispecific Antibodies Using CD3 Antibody 2B5v6

Complimentary construct pairs (12.5 µg of each chain) were co-transfected into 25 mL log phase cultures containing 1 million cells/ml HEK 293 cells using the ExpiFectamine™ 293 Transfection Kit (Life Technologies). Twenty four hours post-transfection, ExpiFectamine Transfection Enhancer was added and cells were allowed to grow an additional 4-5 days before harvesting. Spent cultures were then collected, centrifuged to remove cell debris then passed through a 20 µm filter.

Clarified conditioned media containing GUCY2c T cell bispecific antibodies were then purified using Protein A affinity chromatography. Samples were loaded onto 0.45 mL micro columns (Repligen) pre-packed with MabSelect SuRe protein A resin (GE Healthcare) using a liquid handler (Tecan). Bound protein was washed with PBS pH7.2, then eluted with 20 mM citric acid, 150 mM sodium chloride pH 3.5 and neutralized with 2M tris, pH 8.0. Samples were then de-salted into PBS pH7.2 using G25 Sephadex drip columns (GE Healthcare) according to the manufacturer's methods. Purified proteins were analyzed for purity using analytical size exclusion chromatography with a Mab HTP column (TOSOH) on an Agilent 1200 HPLC following the manufacturer's protocols. Concentrations were determined by measuring at OD280 nm using a micro spectrophotometer (Trinean).

Stability Assessment of Bispecific Antibody Using Differential Scanning calorimetry Proteins were diluted in a phosphate-buffered saline (PBS) solution to 0.6 mg/ml in a volume of 400 µl. PBS was used as a buffer blank in the reference cell. PBS contained 137 mM NaCl, 2.7 mM KCl, 8.1 mM Na2HPO4, and 1.47 mM KH2PO4, pH 7.2. Samples were dispensed into the sample tray of a MicroCal VP-Capillary DSC with Autosampler (Malvern Instruments Ltd, Malvern, UK). Samples were equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions. As shown in FIG. 8, the GUCY2c-2B5v6 bispecific antibody showed excellent thermal stability with $T_m1$ of 70° C.

Binding to Naïve T Cells

Purified CD3 bispecific antibodies were titrated for cell surface binding to human CD3 on naïve human T cells purified from fresh human peripheral blood mononuclear cells (PBMCs), using the standard flow cytometry methods known in the art using BD LSRII Fortessa analyzer. As shown in FIG. 9, the GUCY2c-2B5v6 bispecific bound very well to T cells with an EC50 of binding of 35.44 nM Bispecific Mediated T Cell Activity Assessment Human PBMCs were isolated from healthy donor blood using Histopaque-177 (Sigma). Naïve T cells were isolated from PBMCs using a T cell enrichment kit from Stem Cell Technologies (negative selection of T cells). GUCY2c expressing T84 human tumor cells transfected with a luciferase expression construct were treated with serial dilutions of GUCY2c bispecific antibodies or a negative control CD3 bispecific, together with T cells. The ratio of effector to target cells (E:T) was either 10:1 or 5:1. T cells and tumor cells were incubated at 37° C. for 48 hours, followed by measurement of luciferase signal using the neolite reagent (Perkin Elmer). EC50 values were calculated in Graphpad PRISM using four parameter non-linear regression analysis. Target negative HCT116 or HT29 cells did not show any GUCY2c bispecific-mediated cytotoxicity. As shown in FIG. 10, the GUCY2c-2B5v6 bispecific showed potent cytotoxicity in a T-cell retargeting assay.

T84 cells were treated with T cells (E:T ratio of 5:1) and GUCY2c-1608 (GUCY2c-2B5v6) at different doses. Supernatants were collected at different time points (24 h, 48 h, 96 h) and analyzed using a multiplex Luminnex assay according to the manufacturer's guidelines and read on a Luminex 200 with xPONENT software. The cytokines measured were human IFN-gamma, IL10, IL2, IL4, IL6, TNF-alpha. FIG. 11 shows upregulation of (11A) IFN-gamma, (11B) IL10, (11C) IL2, (11D) IL4, (11E) IL6, (11F) TNF-alpha cytokines following activation of T-cells by GUCY2c-1608.

In Vivo Evaluation of GUCY2c-2B5v6 Bispecific Mediated Activity

In vivo efficacy studies were performed using the adoptive transfer model. Tumor cell lines/patient derived xenograft fragments were implanted in NSG mice and staged to approximately 200 mm³. Mice were dosed with bispecific compounds intravenously (unless otherwise noted). Two million activated and expanded T cells (using the T cell expansion and activation kits from Miltenyi Biotec) were administered IV, 24 h after bispecific dosing. The bispecific antibodies were dosed on a weekly schedule. As shown in FIG. 12 and FIG. 13, GUCY2c-2B5v6 (GUCY2c-1608) bispecific antibody showed excellent durable tumor regressions in both PDX CRX-11201 and cell line LS1034 in vivo models representing colorectal cancer.

Example 9

FLT3-CD3 Bispecific Antibodies and Generation of FLT3-2B5v6 Bispecific IgGs Using Optimized CD3 Antibody (2B5v6) and Cytotoxicity Human FLT3 antibody (xFLT3) and human CD3 antibody (2B5v6) were expressed separately as human IgG2dA_D265A engineered with EEEE on one arm and RRRR on the other arm for bispecific exchange at positions 223, 225, and 228 (e.g., (C223E or C223R), (E225E or E225R), and (P228E or P228R)) in the hinge region and at position 409 or 368 (e.g., K409R or L368E (EU numbering scheme)) in the CH3 region of human IgG2. The antibodies also had the mutation from D to A at position 265 (EU numbering scheme).

Individual antibody arm was separately purified using Protein A resin. One mg/mL of purified xFLT3 antibody was then exchanged with 1 mg/mL of purified 2B5v6 antibody in the presence of 2 mM reduced glutathione. The exchange reaction was carried out at 37° C. for 16 hours. 2 mM of Oxidized glutathione was then added to the proteins and the mixture was incubated at 37° C. for 30 min. The mixture was then 1:5 diluted into 20 mM MES pH 5.4 buffer with no NaCl. The diluted sample was loaded onto the MonoS ion-exchange column and washed with 20 mM MES pH 5.4 25 mM NaCl buffer. The bispecific antibody xFLT3-2B5v6 was next eluted with a gradient of 0-500 mM NaCl in 20 mM MES pH 5.4 buffer. Finally, the bispecific antibody was dialyzed into phosphate-buffered saline (PBS) for cell based assay. For cytotoxicity assays, unstimulated human T cells and luciferase-expressing target cells (Eol-1 or MV411) were co-incubated at defined ratios in 96 well U-bottom plates in 200 µl of RPMI+10% FBS. xFLT3-2B5v6 bispecific antibodies were serially diluted in PBS and added to the wells. After 24 hours, 100 µl of the cell suspension was mixed with 100 µl One-GLO reagent in 96-well white-wall plates and luminescence was measured on an Envision luminometer. Cytotoxicity values were determined using the following formula:

% cytotoxicity=[1−(RLUsample)/RLUtarget cell only)]×100RLU: relative light units As shown in the FIG. 14A and FIG. 14B, xFLT3-2B5v6 bispecific antibody containing optimized the CD3 antibody (2B5v6) appears to be very potent in an alternative bispecific IgG format when tested on both cells expressing higher copies of FLT3 (EOL-1) and lower copies (MV4-11).

Table 13 shows sequences of light and heavy chain of FLT3 (EOL-1), and light and heavy chain of 2B5v6 bispecific antibodies.

TABLE 13

| mAb | Light Chain | Heavy Chain |
|---|---|---|
| xFLT3 | EIVLTQSPATLSLSPGERATLSCR ASQSVSSNLAWYQQKPGQAPRL LIYDTFTRATGIPARFSGSGSGTD FTLTISSLEPEDFAVYYCQQYGS SPPTFGQGTRLEIK (SEQ ID NO: 41) | EVQLLESGGGLVQPGGSLRLSCAA SGFTFSSYAMNWVRQAPGKGLEW VSAISGGGRSTYYADSVKGRFTISR DNSKNTLYLQMNSLRAEDTAVYYC ARDLSPSDVGWGYGFDIWGQGTLV TVSS (SEQ ID NO: 42) |
| 2B5v6 | EVQLVESGGGLVQPGGSLRLSC AASGFTFSDYYMTWVRQAPGKG LEWVAFIRNQARGYTSDHNPSV KGRFTISRDNAKNSLYLQMNSLR AEDTAVYYCARDRPSYYVLDYW GQGTTVTVSS (SEQ ID NO: 4) | DIQMTQSPSSLSASVGDRVTITCTS SQSLFNVRSQKNYLAWYQQKPGKA PKLLIYWASTRESGVPSRFSGSGSG TDFTLTISSLQPEDFATYYCKQSYDL FTFGGGTKVEIK (SEQ ID NO: 3) |

Example 10

T-Cell Epitope De-Risking of 2B5v6 Bispecific Antibody

The optimized clone 2B5v6 was analyzed for potential T-cell epitopes with a desire to de-risk the potential for immunogenicity. Epivax Tool for in silico prediction of potential T-cell Epitopes was used for this analysis. This tool predicts the number of 9-mer frame peptides to bind to any of 8 different HLA alleles. A hit is defined as those with Z-scores in the top 5% and a strong hit in the top 1%. Hits to 4 or more alleles or 1 strong hit are being considered as predicted t-cell epitopes. Based upon these criteria, 3 predicted non-germline T-cell epitopes in the CDRH2, 2 in the CDRL1 and 1 predicted germline epitope in the L2 were identified (Table 15). In addition to scores of individual peptides the overall risk for a sequence can be defined by the total number of hits or the T-regitope Adjusted Epivax Score, which has been optimized to correlate with prevalence of clinical ADA. Here for these predicted values, the lower the score the less expected risk of ADA. Here the VH domain has 70 hits and a score of −42.82, the VL domain has 60 hits and a score of −23.79.

To reduce the immunogenicity risk, mutations that would reduce the overall score of this clone, while removing hits and ideally the predicted t-cell epitopes were identified. All possible single mutant changes in the CDR-L1, CDR-L2 and CDR-H2 were considered to identify ones that would reduce hits, decrease the overall t-regitope adjusted EpiMatrix score and remove the T cell epitopes. Since these potential mutations could also affect binding and stability, care was taken to consider predicted stability and affinity data described above as well to identify mutations that were tolerated. Tables 14A, 14B, and 14C show mutations designed to reduce the immunogenicity risk of 2B5v6. In addition, mutations as shown in SEQ ID NOs 44-47, 51-57, 60 and 62 are predicted to reduce the number of T-cell epitopes.

TABLE 14A

| VH CDR2 residue # in 2B5v6 | | WT residue | Mutated to |
|---|---|---|---|
| Chothia | Kabat | | |
| H50 | H50 | F | H |
| H52A | H52A | N | D |
| H52B | H52B | Q | D |
| H52C | H52C | A | D |
| H55 | H55 | Y | E |
| H56 | H56 | T | P |
| H57 | H57 | S | D |
| H60 | H60 | N | Q |

TABLE 14B

| VL CDR1 residue # in 2B5v6 | | WT residue | Mutated to |
|---|---|---|---|
| Chothia | Kabat | WT | Mut |
| L26 | L26 | S | D |
| L27 | L27 | Q | E |
| L28 | L27A | S | D |
| L30B | L27E | V | E |
| L30D | L28 | S | T |
| L30E | L29 | Q | G |
| L30F | L30 | K | Q |
| L31 | L31 | N | E |
| L34 | L34 | A | N |

TABLE 14C

| VL CDR2 residue # in 2B5v6 | | WT residue | Mutated to |
|---|---|---|---|
| Chothia | Kabat | WT | Mut |
| L51 | L51 | A | T |
| L53 | L53 | T | D |
| L54 | L54 | R | D |
| L54 | L54 | R | Q |
| L56 | L56 | S | D |
| germline | germline | WASTRES (SEQ ID NO: 27) | AASSLQS (SEQ ID NO: 43) |

Table 15 shows the regions of CD3 antibody (2B5v6) variable domain with T-cell epitopes and posing potential immunogenicity risk.

TABLE 15

| VH/VL | Peptide | Hits | Strong Hits |
|---|---|---|---|
| VH | VQPGGSLRL (SEQ ID NO: 44) | 2 | 0 |
| VH | LRLSCAASG (SEQ ID NO: 45) | 7 | 4 |
| VH | WVRQAPGKG (SEQ ID NO: 46) | 4 | 3 |
| VH | VRQAPGKGL (SEQ ID NO: 47) | 3 | 0 |
| VH | WVAFIRNQA (SEQ ID NO: 48) | 2 | 1 |
| VH | FIRNQARGY (SEQ ID NO: 49) | 5 | 2 |
| VH | YTSDHNPSV (SEQ ID NO: 50) | 4 | 2 |
| VH | VKGRFTISR (SEQ ID NO: 51) | 2 | 0 |
| VH | FTISRDNAK (SEQ ID NO: 52) | 5 | 0 |
| VH | LYLQMNSLR (SEQ ID NO: 53) | 6 | 2 |
| VH | YLQMNSLRA (SEQ ID NO: 54) | 8 | 5 |
| VH | LQMNSLRAE (SEQ ID NO: 55) | 2 | 0 |
| VL | IQMTQSPSS (SEQ ID NO: 56) | 6 | 1 |
| VL | MTQSPSSLS (SEQ ID NO: 57) | 7 | 0 |
| VL | ITCTSSQSL (SEQ ID NO: 58) | 3 | 1 |
| VL | VRSQKNYLA (SEQ ID NO: 59) | 8 | 5 |
| VL | WYQQKPGKA (SEQ ID NO: 60) | 5 | 0 |
| VL | LLIYWASTR (SEQ ID NO: 61) | 2 | 1 |
| VL | FTLTISSLQ (SEQ ID NO: 62) | 7 | 5 |

All the mutants were generated as monovalent IgG antibodies using standard transient HEK293 expression followed by purification using Protein A column. The resulting clones were tested for binding to Jurkat cells expressing CD3 using FACS and self-association potential using AC-SINS as described above in Example 7. As shown in in Table 16, five molecules with improved epivax score and reduced T-cell epitopes and retained affinity to CD3 were chosen to move forward and test in diabody-Fc format. The 2B5v6 variants with improved epivax scores were compared to the parental 2B5v6. The results show comparable binding to Jurkat cells expressing CD3 and AC-SINS scores.

TABLE 16

| Variant | EC50 (nM) Jurkat cells | AC-SINS | Epivax Score |
|---|---|---|---|
| 2B5v6-0453 | 11.1 | 0 | −47.18 |
| 2B5v6-0517 | 9.9 | 1 | −42.92 |
| 2B5v6-0522 | 8.6 | 0 | −46.6 |
| 2B5v6-0533 | 6.1 | 1 | −38.8 |
| 2B5v6-0538 | 9.2 | 0 | −42.47 |
| 2B5v6 | 9.8 | 1 | −33.67 |

Among the mutants tested, several mutants exhibited lower binding to Jurkat cells compared to 2B5v6. Of these mutants, the ones with all the T-cell epitopes eliminated and improved epivax scores were taken forward to generate diabody-Fc bispecific molecules with GUCY2c antibody as other binding domain. Table 17 shows the epivax scores and FIG. 15 shows reduced binding for these mutants to jurkat cells. The low-affinity CD3 antibody 2B5v6 variants show improved epivax scores.

TABLE 17

| CD3 Antibody Variants | Epivax Score (tReg-Adjusted) |
|---|---|
| 2B5v6-0598 | −65.15 |
| 2B5v6-0623 | −56.74 |

Example 11

Three Anti-CD3 Variants Show Improved Affinity and Cytotoxicity in GUCY2C-CD3 Bispecific Antibodies Three anti-CD3 variants, 2B5-1038 (SEQ ID NOs: 4 and 9), 2B5-1039 (SEQ ID NOs: 4 and 87), and 2B5-1040 (SEQ ID NOs: 4 and 89) that are derived from 2B5v6, were reformatted into bispecific diabody-Fc molecules paired with anti-tumor GUCY2c antibody sequence in one of the configurations shown in FIG. 1 using standard cloning, expression and purification techniques described hereinabove. The resulting bispecific antibodies shown in Table 18 were tested for in vitro cytotoxicity using a T-cell retargeting assay, and binding affinity using surface plasmon resonance (SPR) assay and non-specificity by AC-SINs. The immunogenicity risk was evaluated by Epivax Tool for in silico prediction of potential T-cell epitopes. Intact mass spectroscopy data indicates that all bispecifics have correct pairing and are 100% heterodimers. Table 18 demonstrates that all three bispecifics (1) are around 2-fold more potent in an in vitro cytotoxicity assay as compared to control bispecific GUCY2C-1608 which is paired with anti-CD3 2B5v6 (FIG. 16); (2) have binding affinity to recombinant human CD3 by SPR that is consistent with cytotoxicity activity; (3) have immunogenicity scores that are improved over control; and (4) AC-SINs scores maintained the same as control bispecific GUCY2C-1608. These results demonstrate that anti-GUCY2c bispecific antibodies with different CD3 variants recruit naïve human T cells to induce cell killing in T84 tumor cells (FIG. 16). The three anti-CD3 variants derived from 2B5v6 demonstrated approximately 2-fold more potent activity compared to control bispecific GUCY2C-1608.

TABLE 18

| Bispecific | CD3 variant | Epivax Score (tReg-Adjusted) | MassSpec (intact) | AC-SINs score | In vitro Cytotoxicity (nM) | KD (nM, SPR) |
|---|---|---|---|---|---|---|
| GUCY2C-1608 | 2B5-0542 | −33.7 | 100% heterodimer | 3 | 0.772 | 127.88 ± 1.63 |
| GUCY2C-1678 | 2B5-1038 | −52.61 | 100% heterodimer | 2 | 0.247 | 63.55 ± 0.49 |
| GUCY2C-1679 | 2B5-1040 | −47.58 | 100% heterodimer | 3 | 0.194 | 72.02 ± 0.36 |
| GUCY2C-1680 | 2B5-1039 | −53.51 | 100% heterodimer | 3 | 0.385 | 78.57 ± 0.9 |

Sequences for the bispecific antibodies are set forth in Table 19.

TABLE 19

| Bispecific | First polypeptide chain | Second polypeptide chain |
|---|---|---|
| GUCY2C-1608 | DIQLTQSPSSLSASVGDRVTIT CRASESVDYYGSSLLQWYQQ KPGKAPKLLIYAASKLASGVPS RFSGSGSGTDFTLTISSLQPE DFATYYCQQTRKAYTFGQGT KLEIKGGGSGGGGEVQLVES GGGLVQPGGSLRLSCAASGF TFSDYYMTWVRQAPGKGLEW VAFIRNQARGYTSDHNPSVKG RFTISRDNAKNSLYLQMNSLR AEDTAVYYCARDRPSYVLDY WGQGTTVTVSSGCPPCPAPE AAGAPSVFLFPPKPKDTLMI SRTPEVTCVVVDVSHEDPEVK FNWYVDGVEVHNAKTKPREE QYNSTYRVVSVLTVLHQDWLN GKEYKCKVSNKALPAPIEKTIS KAKGQPREPQVCTLPPSREE MTKNQVSLWCLVKGFYPSDIA VEWESNGQPENNYKTTPPVL | DIQMTQSPSSLSASVGDRVTITC TSSQSLFNVRSQKNYLAWYQQK PGKAPKLLIYWASTRESGVPSRF SGSGSGTDFTLTISSLQPEDFAT YYCKQSYDLFTGGGTKVEIKGG GGSGGGGEVQLVESGGGLVQP GGSLRLSCAASGFTFSSYWMHW VRQAPGKGLEWIGEIKPSNELTN VHEKFKDRFTISVDKAKNSAYLQ MNSLRAEDTAVYYCTRTITTTEG YWFFDVWGQGTLVTVSSGCPPC PAPEAAGAPSVFLFPPKPKDTLMI SRTPEVTCVVVDVSHEDPEVKFN WYVDGVEVHNAKTKPREEQYNS TYRVVSVLTVLHQDWLNGKEYK CKVSNKALPAPIEKTISKAKGQPR EPQVYTLPPCREEMTKNQVSLS CAVKGFYPSDIAVEWESNGQPE NNYKTTPPVLDSDGSFFLVSKLT VDKSRWQQGNVFSCSVMHEAL |

TABLE 19-continued

| Bispecific | First polypeptide chain | Second polypeptide chain |
|---|---|---|
| | DSDGSFFLYSKLTVDKSRWQ<br>QGNVFSCSVMHEALHNHYTQ<br>KSLSLSPG<br>(SEQ ID NO: 93) | HNHYTQKSLSLSPG<br>(SEQ ID NO: 94) |
| GUCY2C-1678 | DIQLTQSPSSLSASVGDRVTIT<br>CRASESVDYYGSSLLQWYQQ<br>KPGKAPKLLIYAASKLASGVPS<br>RFSGSGSGTDFTLTISSLQPE<br>DFATYYCQQTRKAYTFGQGT<br>KLEIKGGGSGGGGEVQLVES<br>GGGLVQPGGSLRLSCAASGF<br>TFSDYYMTWVRQAPGKGLEW<br>VAFIRNQARGYTSDHNPSVKG<br>RFTISRDNAKNSLYLQMNSLR<br>AEDTAVYYCARDRPSYYVLDY<br>WGQGTTVTVSSGCPPCPAPE<br>AAGAPSVFLFPPKPKDTLMISR<br>TPEVTCVVVDVSHEDPEVKFN<br>WYVDGVEVHNAKTKPREEQY<br>NSTYRVVSVLTVLHQDWLNGK<br>EYKCKVSNKALPAPIEKTISKA<br>KGQPREPQVYTLPPCREEMTKNQVSLS<br>KGQPREPQVCTLPPSREEMT<br>CAVKGFYPSDIAVEWESNGQPE<br>KNQVSLWCLVKGFYPSDIAVE<br>WESNGQPENNYKTTPPVLDS<br>DGSFFLYSKLTVDKSRWQQG<br>NVFSCSVMHEALHNHYTQKSL<br>SLSPG<br>(SEQ ID NO: 95) | DIQMTQSPSSLSASVGDRVTITC<br>TSDQSLFNVRSGKNYLAVYQQK<br>PGKAPKLLIYWASDRESGVPSRF<br>SGSGSGTDFTLTISSLQPEDFAT<br>YYCKQSYDLFTFGGGTKVEIKGG<br>GGSGGGGEVQLVESGGGLVQP<br>GGSLRLSCAASGFTFSSYWMHW<br>VRQAPGKGLEWIGEIKPSNELTN<br>VHEKFKDRFTISVDKAKNSAYLQ<br>MNSLRAEDTAVYYCTRTITTTEG<br>YWFFDVWGQGTLVTVSSGCPPC<br>PAPEAAGAPSVFLFPPKPKDTLMI<br>SRTPEVTCVVVDVSHEDPEVKFN<br>WYVDGVEVHNAKTKPREEQYNS<br>TYRWSVLTVLHQDWLNGKEYK<br>CKVSNKALPAPIEKTISKAKGQPR<br>EPQVYTLPPCREEMTKNQVSLS<br>NNYKTTPPVLDSDGSFFLVSKLT<br>VDKSRWQQGNVFSCSVMHEAL<br>HNHYTQKSLSLSPG<br>(SEQ ID NO: 96) |
| GUCY2C-1679 | DIQLTQSPSSLSASVGDRVTIT<br>CRASESVDYYGSSLLQWYQQ<br>KPGKAPKLLIYAASKLASGVPS<br>RFSGSGSGTDFTLTISSLQPE<br>DFATYYCQQTRKAYTFGQGT<br>KLEIKGGGSGGGGEVQLVES<br>GGGLVQPGGSLRLSCAASGF<br>TFSDYYMTWVRQAPGKGLEW<br>VAFIRNQARGYTSDHNPSVKG<br>RFTISRDNAKNSLYLQMNSLR<br>AEDTAVYYCARDRPSYYVLDY<br>WGQGTTVTVSSGCPPCPAPE<br>AAGAPSVFLFPPKPKDTLMISR<br>TPEVTCVVVDVSHEDPEVKFN<br>WYVDGVEVHNAKTKPREEQY<br>NSTYRVVSVLTVLHQDWLNGK<br>EYKCKVSNKALPAPIEKTISKA<br>KGQPREPQVCTLPPSREEMT<br>KNQVSLWCLVKGFYPSDIAVE<br>WESNGQPENNYKTTPPVLDS<br>DGSFFLYSKLTVDKSRWQQG<br>NVFSCSVMHEALHNHYTQKSL<br>SLSPG<br>(SEQ ID NO: 97) | DIQMTQSPSSLSASVGDRVTITC<br>TSSQSLFNVRSGKNYLAWYQQK<br>PGKAPKLLIYWASDRESGVPSRF<br>SGSGSGTDFTLTISSLQPEDFAT<br>YYCKQSYDLFTFGGGTKVEIKGG<br>GGSGGGGEVQLVESGGGLVQP<br>GGSLRLSCAASGFTFSSYWMHW<br>VRQAPGKGLEWIGEIKPSNELTN<br>VHEKFKDRFTISVDKAKNSAYLQ<br>MNSLRAEDTAVYYCTRTITTTEG<br>YWFFDVWGQGTLVTVSSGCPPC<br>PAPEAAGAPSVFLFPPKPKDTLMI<br>SRTPEVTCVVVDVSHEDPEVKFN<br>WYVDGVEVHNAKTKPREEQYNS<br>TYRWSVLTVLHQDWLNGKEYK<br>CKVSNKALPAPIEKTISKAKGQPR<br>EPQVYTLPPCREEMTKNQVSLS<br>CAVKGFYPSDIAVEWESNGQPE<br>NNYKTTPPVLDSDGSFFLVSKLT<br>VDKSRWQQGNVFSCSVMHEAL<br>HNHYTQKSLSLSPG<br>(SEQ ID NO: 98) |
| GUCY2C-1680 | DIQLTQSPSSLSASVGDRVTIT<br>CRASESVDYYGSSLLQWYQQ<br>KPGKAPKLLIYAASKLASGVPS<br>RFSGSGSGTDFTLTISSLQPE<br>DFATYYCQQTRKAYTFGQGT<br>KLEIKGGGSGGGGEVQLVES<br>GGGLVQPGGSLRLSCAASGF<br>TFSDYYMTWVRQAPGKGLEW<br>VAFIRNQARGYTSDHNPSVKG<br>RFTISRDNAKNSLYLQMNSLR<br>AEDTAVYYCARDRPSYYVLDY<br>WGQGTTVTVSSGCPPCPAPE<br>AAGAPSVFLFPPKPKDTLMISR<br>TPEVTCVVVDVSHEDPEVKFN<br>WYVDGVEVHNAKTKPREEQY<br>NSTYRVVSVLTVLHQDWLNGK<br>EYKCKVSNKALPAPIEKTISKA<br>KGQPREPQVCTLPPSREEMT | DIQMTQSPSSLSASVGDRVTITC<br>TSSESLFNVRSGKNYLAWYQQK<br>PGKAPKLLIYWASDRESGVPSRF<br>SGSGSGTDFTLTISSLQPEDFAT<br>YYCKQSYDLFTFGGGTKVEIKGG<br>GGSGGGGEVQLVESGGGLVQP<br>GGSLRLSCAASGFTFSSYWMHW<br>VRQAPGKGLEWIGEIKPSNELTN<br>VHEKFKDRFTISVDKAKNSAYLQ<br>MNSLRAEDTAVYYCTRTITTTEG<br>YWFFDVWGQGTLVTVSSGCPPC<br>PAPEAAGAPSVFLFPPKPKDTLMI<br>SRTPEVTCVVVDVSHEDPEVKFN<br>WYVDGVEVHNAKTKPREEQYNS<br>TYRWSVLTVLHQDWLNGKEYK<br>CKVSNKALPAPIEKTISKAKGQPR<br>EPQVYTLPPCREEMTKNQVSLS<br>CAVKGFYPSDIAVEWESNGQPE |

TABLE 19-continued

| Bispecific | First polypeptide chain | Second polypeptide chain |
|---|---|---|
| | KNQVSLWCLVKGFYPSDIAVE WESNGQPENNYKTTPPVLDS DGSFFLYSKLTVDKSRWQQG NVFSCSVMHEALHNHYTQKSL SLSPG (SEQ ID NO: 99) | NNYKTTPPVLDSDGSFFLVSKLT VDKSRWQQGNVFSCSVMHEAL HNHYTQKSLSLSPG (SEQ ID NO: 100) |

What is claimed is:

1. An antibody which specifically binds to CD3, wherein the antibody comprises:

(a) a heavy chain variable (VH) region comprising a VH complementarity determining region one (VH CDR1), a VH complementarity determining region two (VH CDR2), and a VH complementarity determining region three (VH CDR3) of the VH sequence shown in SEQ ID NO: 2, and a light chain variable (VL) region comprising a VL complementarity determining region one (VL CDR1), a VL complementarity determining region two (VL CDR2), and a WL complementarity determining region three (VL CDR3) of the VL sequence shown in SEQ ID NO: 3;

(b) a VH CDR1, a VH CDR2 and a VH CDR3 of the VH sequence shown in SEQ ID NO: 4, and a VL CDR1, a VL CDR2 and a VL CDR of the VL sequence shown in SEQ ID NO:3;

(c) a VH CDR1, a VH CDR2 and a VH CDR3 of the VH sequence shown in SEQ ID NO: 5, and a VL CDR1, a VL CDR2 and a VL CDR3 of the VL sequence shown in SEQ ID NO:3;

(d) a VH CDR1, a VH CDR2 and a VH CDR3 of the VH sequence shown in SEQ ID NO: 7, and a VL CDR1, a VL CDR2 and a VL CDR3 of the VL sequence shown in SEQ ID NO:6;

(e) a VH CDR1, a VH CDR2 and a VH CDR3 of the VH sequence shown in SEQ ID NO: 7, and a VL CDR1, a VL CDR2 and a VL CDR3 of the VL sequence shown in SEQ ID NO:8;

(f) a VH CDR1, a VH CDR2 and a VH CDR3 of the VH sequence shown in SEQ ID NO: 4, and a VL CDR1, a VL CDR2 and a VL CDR of the VL sequence shown in SEQ ID NO 6;

(g) a VH CDR1, a VH CDR2 and a VH CDR3 of the VH sequence shown in SEQ ID NO: 4, and a VL CDR1, a VL CDR2 and a VL CDR3 of the VL sequence shown in SEQ ID NO:8;

(h) a VH CDR1, a VH CDR2 and a VH CDR3 of the VH sequence shown in SEQ ID NO: 10, and a VL CDR1, a VL CDR2 and a VL CDR3 of the VL sequence shown in SEQ ID NO:9;

(i) a VH CDR1, a VH CDR2 and a VH CDR3 of the VH sequence shown in SEQ ID NO: 7, and a VL CDR1, a VL CDR2 and a VL CDR3 of the VL sequence shown in SEQ ID NO:9;

(j) a VH CDR1, a VH CDR2 and a VH CDR3 of the VH sequence shown in SEQ ID NO: 12, and a VL CDR1, a VL CDR2 and a VL CDR3 of the VL sequence shown in SEQ ID NO:11; or (k) a VH CDR1, a VH CDR2 and a VH CDR3 of the VH sequence shown in SEQ ID NO: 35, and a VL CDR1, a VL CDR2 and a VL CDR3 of the VL sequence shown in SEQ ID NO:34.

2. The antibody of claim 1, wherein the antibody comprises:

a. a VH region comprising (i) a VH CDR1 comprising a sequence of SEQ ID NO: 13, 14, or 15; (ii) a VH CDR2 comprising a sequence of SEQ ID NO: 19 or 20; and iii) a VH CDR3 comprising a sequence of SEQ ID NO: 18; and b. a VL region comprising (i) a VL CDR1 comprising a sequence of SEQ ID NO: 29; (ii) a VL CDR2 comprising a sequence of SEQ ID NO: 27; and (iii) a VL CDR3 comprising a sequence of SEQ ID NO: 28.

3. The antibody of claim 1, wherein:

a. the VH region comprises a sequence of SEQ ID NO: 4; and b. the VL region comprises a sequence of SEQ ID NO: SEQ ID NO: 3.

4. The antibody of claim 3, wherein the antibody is selected from the group consisting of a Fab, a Fab fragment, a F(ab)₂ fragment, an Fv fragment, a single chain Fv fragment, a disulfide stabilized Fv fragment, a single-chain antibody, a monoclonal antibody, a chimeric antibody, a bispecific antibody, a trispecific antibody, a multispecific antibody, a bispecific heterodimeric diabody, a bispecific heterodimeric IgG, a polyclonal antibody, a labeled antibody, a humanized antibody, and fragments thereof.

5. The antibody of claim 4, wherein the antibody is a bispecific antibody.

6. The bispecific antibody of claim 5, that specifically binds to a tumor antigen.

7. The antibody of claim 6, further comprising a human or humanized VH framework and a human or humanized VL framework.

8. The antibody of claim 7, wherein the antibody is a humanized antibody.

9. A pharmaceutical composition comprising the antibody of claim 8, and a pharmaceutically acceptable carrier.

10. A method of modulating a T cell mediated immune response in a subject in need thereof, comprising administering to the subject the antibody of claim 1, or the pharmaceutical composition of claim 9 such that the immune response in the subject is modulated.

11. A method of inhibiting growth of tumor cells in a subject, comprising administering to the subject the antibody of claim 1, or the pharmaceutical composition of claim 9, in an amount effective to inhibit growth of the tumor cells.

12. The method of claim 11, wherein the tumor cells are of a cancer.

13. The method of claim 12, wherein the cancer is selected from the group consisting of breast, ovarian, thyroid, prostate, cervical, lung, bladder, endometrial, head and neck, testicular, glioblastoma cancer and cancer of digestive system.

14. The method of claim 13, wherein the cancer of digestive system is selected from the group consisting of esophagus, stomach, small intestine, colon, rectum, anus, liver, gall bladder, appendix, bile ducts, and pancreas.

15. A polynucleotide comprising a nucleotide sequence encoding the antibody of claim 1.

16. A vector comprising the polynucleotide of claim 15.

17. A host cell comprising the vector of claim 16.

18. The host cell of claim 17, wherein the host cell is selected from the group consisting of bacterial cell lines, mammalian cell lines, insect cell lines, and yeast cell lines.

19. The host cell of claim 18, wherein the mammalian cell line is a CHO cell line.

20. A method of producing an antibody comprising culturing the host cell of claim 17, under conditions that result in production of the antibody of claim 1, and purifying the antibody from the culture supernatant.

* * * * *